(12) United States Patent
Hatakeyama et al.

(10) Patent No.: US 11,357,970 B2
(45) Date of Patent: *Jun. 14, 2022

(54) BIOMEDICAL ELECTRODE COMPOSITION, BIOMEDICAL ELECTRODE AND METHOD FOR MANUFACTURING THE BIOMEDICAL ELECTRODE

(71) Applicant: SHIN-ETSU CHEMICAL CO., LTD., Tokyo (JP)

(72) Inventors: Jun Hatakeyama, Jyoetsu (JP); Takayuki Fujiwara, Jyoetsu (JP); Osamu Watanabe, Jyoetsu (JP); Motoaki Iwabuchi, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 1112 days.

This patent is subject to a terminal disclaimer.

(21) Appl. No.: 15/856,571

(22) Filed: Dec. 28, 2017

(65) Prior Publication Data

US 2018/0193632 A1 Jul. 12, 2018

(30) Foreign Application Priority Data

Jan. 6, 2017 (JP) .............................. JP2017-000896

(51) Int. Cl.
| | |
|---|---|
| *A61N 1/04* | (2006.01) |
| *C08L 33/10* | (2006.01) |
| *C08L 33/08* | (2006.01) |
| *C08K 3/04* | (2006.01) |
| *C08L 33/14* | (2006.01) |
| *C08L 33/16* | (2006.01) |
| *C08F 220/24* | (2006.01) |

(Continued)

(52) U.S. Cl.
CPC .............. *A61N 1/042* (2013.01); *A61B 5/259* (2021.01); *C08F 220/24* (2013.01); *C08F 220/387* (2020.02); *C08K 3/04* (2013.01); *C08L 25/18* (2013.01); *C08L 33/08* (2013.01); *C08L 33/10* (2013.01); *C08L 33/14* (2013.01); *C08L 33/16* (2013.01); *A61B 5/25* (2021.01); *A61B 2562/0215* (2017.08); *A61B 2562/125* (2013.01); *C08F 212/20* (2020.02); *C08F 212/30* (2020.02); *C08K 2201/001* (2013.01); *C08L 2203/02* (2013.01); *C08L 2203/20* (2013.01)

(58) Field of Classification Search
CPC ...... C08F 220/24; C08F 220/387; C08K 3/04; C08K 3/041; H01M 4/137; H01M 4/602–608; H01M 4/622–623; H01M 2300/0082; A61N 1/042; A61N 1/0436
See application file for complete search history.

(56) References Cited

U.S. PATENT DOCUMENTS 5,981,680 A 11/1999 Petroff et al.
10,734,132 B2 * 8/2020 Hatakeyama ......... C08F 220/38
(Continued)

FOREIGN PATENT DOCUMENTS

JP H05-095924 A 4/1993
JP H08-155040 A 6/1996
(Continued)

OTHER PUBLICATIONS

Li et al. Synthesis of Sodium Poly[4-styrenesulfonyl(trifluoromethylsulfonyl) imide]-co-ethylacrylate] Solid Polymer Electrolytes. Electrochimica Acta 2015, 175, 232-239. (Year: 2015).*

(Continued)

*Primary Examiner* — Stephen E Rieth
(74) *Attorney, Agent, or Firm* — Oliff PLC

(57) ABSTRACT

The present invention provides a biomedical electrode composition capable of forming a living body contact layer for a biomedical electrode that is excellent in conductivity and biocompatibility, is light-weight, can be manufactured at low cost, and can control significant reduction in conductivity even though the biomedical electrode is soaked in water or dried. The present invention was accomplished by a biomedical electrode composition including a polymer compound having both the ionic repeating unit "a" and the repeating unit "b" of (meth)acrylate, in which the ionic repeating unit "a" is a repeating unit of sodium salt, potassium salt, or ammonium salt including a partial structure represented by the following general formula (1), and the repeating unit "b" of (meth)acrylate is a repeating unit represented by the following general formula (2).

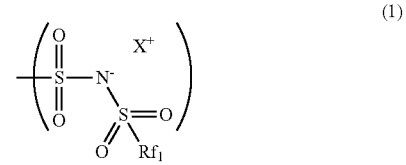

(1)

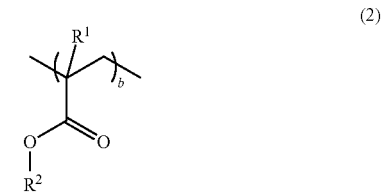

(2)

20 Claims, 2 Drawing Sheets

(51) Int. Cl.
  *C08F 220/38* (2006.01)
  *C08F 212/14* (2006.01)
  *A61B 5/259* (2021.01)
  *C08L 25/18* (2006.01)
  *A61B 5/25* (2021.01)

(56) References Cited

U.S. PATENT DOCUMENTS

| | | |
|---|---|---|
| 2002/0009650 A1 | 1/2002 | Michot et al. |
| 2002/0177039 A1 | 11/2002 | Lu et al. |
| 2002/0188069 A1 | 12/2002 | Sugo et al. |
| 2007/0247565 A1* | 10/2007 | Sasaki ............... C09B 67/0033 349/70 |
| 2008/0118860 A1 | 5/2008 | Harada et al. |
| 2009/0061358 A1 | 3/2009 | Ohashi et al. |
| 2014/0296418 A1 | 10/2014 | Sato et al. |
| 2014/0303470 A1 | 10/2014 | Tsukada et al. |
| 2015/0275060 A1 | 10/2015 | Kuroda et al. |
| 2016/0155530 A1 | 6/2016 | Someya et al. |
| 2016/0190641 A1 | 6/2016 | Lee et al. |
| 2016/0276057 A1* | 9/2016 | Navarro ............... C08K 3/04 |
| 2017/0149104 A1* | 5/2017 | Ma ............... H01M 10/0525 |

FOREIGN PATENT DOCUMENTS

| | | | |
|---|---|---|---|
| JP | 2002-332305 A | | 11/2002 |
| JP | 2002-356661 A | | 12/2002 |
| JP | 2003-064259 A | | 3/2003 |
| JP | 2003-225217 A | | 8/2003 |
| JP | 2004-033468 A | | 2/2004 |
| JP | 2004-527902 A | | 9/2004 |
| JP | 2005-320418 A | | 11/2005 |
| JP | 2008-111103 A | | 5/2008 |
| JP | 2009-080474 A | | 4/2009 |
| JP | 2011-079946 A | | 4/2011 |
| JP | 2011068768 A | * | 4/2011 |
| JP | 2013-185119 A | | 9/2013 |
| JP | 2015-019806 A | | 2/2015 |
| JP | 2015-100673 A | | 6/2015 |
| JP | 2015-193803 A | | 11/2015 |
| JP | 2016-011338 A | | 1/2016 |
| JP | 2016-065238 A | | 4/2016 |
| JP | 2016118619 A | * | 6/2016 |
| WO | 2013/039151 A1 | | 3/2013 |
| WO | 2013073673 A1 | | 5/2013 |

OTHER PUBLICATIONS

Li et al. Increased ion conduction in dual cation [sodium]-[tetraalkylammonium] poly-[4-styrenesulfonyl(trifluoromethylsulfonyl) imideco-ethylacrylate] ionomers. J. Mater. Chem. A., 2015, 3, 19989-19995. (Year: 2015).*
Machine Translation of JP2016-118619A. Jun. 30, 2016. (Year: 2016).*
Machine Translation of JP2011-068768A. Apr. 7, 2011 (Year: 2011).*
New Jersey Department of Health. Hazardous Substance Fact Sheet: Carbon Black. Nov. 2016. (Year: 2016).*
Jan. 5, 2021 Office Action issued in Japanese Patent Application No. 2017-235554.
Long et al. "Polymer electrolytes for lithium polymer batteries." Journal of Materials Chemistry A, May 25, 2016, vol. 4, pp. 10038-10069.
Jun. 18, 2018 Extended European Search Report in European Patent Application No. 18155190.4.
Database WPI Week 200375 Thomson Scientific, London, GB; AN 2003-792558 XP-002781560, 2017.
May 2, 2019 Office Action issued in U.S. Appl. No. 15/883,751.
Aug. 9, 2019 Office Action issued in Korean Patent Application No. 2018-0013976.
Oct. 8, 2019 Office Action issued in U.S. Appl. No. 15/883,751.
Mar. 11, 2020 Notice of Allowance Issued in U.S. Appl. No. 15/883,751.
Mar. 25, 2020 Office Action issued in European Patent Application No. 18155190.4.
Sahika Inal et al.; "Organic Electrochemical Transistors Based on PEDOT with Different Anionic Polyelectrolyte Dopants"; Journal of Polymer Science, Part B: Polymer Physics; 2016; vol. 54; pp. 147-151.

* cited by examiner (a)

(b)

BIOMEDICAL ELECTRODE COMPOSITION, BIOMEDICAL ELECTRODE AND METHOD FOR MANUFACTURING THE BIOMEDICAL ELECTRODE

TECHNICAL FIELD

The present invention relates to a biomedical electrode that is used in contact with the skin of a living body capable of detecting physical conditions such as heart rate by an electric signal transmitted from the skin, a method for manufacturing the biomedical electrode, and a biomedical electrode composition desirably used in a biomedical electrode.

BACKGROUND ART

A recent growing popularity of Internet of Things (IoT) has accelerated the development of such major wearable devices as watches and glasses that allow for Internet access. Even in the fields of medicine and sports, wearable devices for constantly monitoring the user's physical state are increasingly demanded, and such technological development is expected to be further encouraged.

One typical medical wearable device is designed to monitor the state of human organs by detecting extremely weak current, including an electrocardiogram for detecting an electric signal to find out the heartbeat, and has been examined. The electrocardiogram measurement is conducted by attaching an electrode coated with a conductive paste to a body, but this is merely a single (not continuous), short-time measurement. On the other hand, the medical wearable device is aimed at continuously monitoring physical conditions for a few weeks. Accordingly, a biomedical electrode used in medical wearable devices is required to make no changes in conductivity even in long-time use and cause no skin allergy. In addition to these advantages, such wearable devices need being light-weight and manufacturing at low cost.

Medical wearable devices are classified into two types: direct body attachment and clothing attachment. One typical body attachment device is a biomedical electrode formed of a hydrophilic gel containing water and electrolytes as ingredients of the above conductive paste (Patent Document 1). The hydrophilic gel, containing sodium, potassium, and calcium electrolytes in a hydrophilic polymer for containing water, detects changes in ion concentration from the skin to convert the data into electricity. Meanwhile, one typical clothing attachment device is characterized by a method for using a fabric including a conductive polymer, such as PEDOT-PSS (Poly-3,4-ethylenedioxythiophene-polystyrenesulfonate), and a silver paste incorporated into the fiber as an electrode (Patent Document 2).

However, the use of the hydrophilic gel containing water and electrolytes unfortunately brings about loss of conductivity due to water evaporation in drying process. Meanwhile, the use of a higher ionization tendency metal such as copper causes some users to suffer from skin allergy, and a conductive polymer such as PEDOT-PSS can also cause skin allergy due to its strong acidity.

By taking advantage of excellent conductivity, the use of electrode materials formed of metal nanowire, carbon black, or carbon nanotube has been examined (Patent Document 3, 4, and 5). With higher contact probability between wires, metal nanowires can conduct electricity in small quantities to be added. Nevertheless, metal nanowires, formed of a pointed thin material, may cause skin allergy. Likewise, carbon nanotubes can stimulate a living body. Although the carbon black is not as poisonous as carbon nanotube, it also stimulates the skin. Accordingly, even though these electrode materials themselves cause no allergic reaction, the biocompatibility can be degraded depending on the shape of a material and its inherent stimulation, thereby failing to satisfy both conductivity and biocompatibility.

Although metal films seem to function as an excellent biomedical electrode due to extremely high conductivity, this is not always the case. Upon heartbeat, the human skin releases a sodium ion, a potassium ion, or a calcium ion, instead of extremely weak current. It is thus necessary to convert changes in ion concentration into current, but less ionized precious metals unfortunately fail to do so efficiently. The resulting biomedical electrode including the precious metal is characterized by high impedance and high resistance to the skin during electrical conduction.

Meanwhile, the use of a battery containing an ionic liquid has been examined (Patent Document 6). Advantageously, the ionic liquid is thermally and chemically stable, and the conductivity is excellent, providing more various battery applications. However, an ionic liquid having smaller molecular weight shown in Patent Document 6 unfortunately dissolves into water. The use of a biomedical electrode containing such an ionic liquid allows the ionic liquid to be extracted from the electrode by sweating from the skin, which not only lowers the conductivity, but also causes rough skin by the liquid soaking into the skin.

In addition, biomedical electrodes fail to get biological information when it is apart from the skin. Even changes in contact area can vary quantities of electricity traveling through the electrode, thereby fluctuating the baseline of an electrocardiogram (electric signal). Accordingly, in order to stably detect electric signals from the body, the biomedical electrode is required to be in constant contact with the skin and make no changes in contact area. This requirement is preferably satisfied by use of adhesive biomedical electrodes. Additionally, elastic and flexible biomedical electrodes are needed to follow changes in skin expansion and flexion.

PRIOR ART DOCUMENTS

Patent Documents

Patent Document 1: WO2013/039151
Patent Document 2: JP-A-2015-100673
Patent Document 3: JP-A-5-095924
Patent Document 4: JP-A-2003-225217
Patent Document 5: JP-A-2015-019806
Patent Document 6: JP-A-2004-527902

SUMMARY OF INVENTION

Technical Problem

The present invention was made in view of the situation to solve the problems, and has an object to provide a biomedical electrode composition capable of forming a living body contact layer for a biomedical electrode that is excellent in conductivity and biocompatibility, is light-weight, can be manufactured at low cost, and can control significant reduction in conductivity even though the biomedical electrode is soaked in water or dried, a biomedical electrode including a living body contact layer formed of the biomedical electrode composition, and a method for manufacturing the biomedical electrode.

Solution to Problem

To solve these problems, the present invention provides a biomedical electrode composition including a polymer compound having both an ionic repeating unit "a" and a repeating unit "b" of (meth)acrylate, wherein the ionic repeating unit "a" is a repeating unit of a sodium salt, a potassium salt, or an ammonium salt including a partial structure represented by the following general formula (1), and the repeating unit "b" of (meth)acrylate is a repeating unit represented by the following general formula (2),

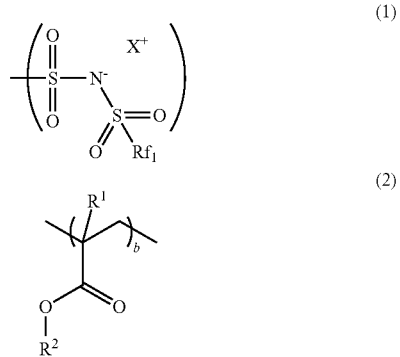

wherein, $Rf_1$ represents a linear, or a branched alkyl group having 1 to 4 carbon atoms, having at least one fluorine atom; $X^+$ represents any of a sodium ion, a potassium ion, or an ammonium ion; $R^1$ represents a hydrogen atom or a methyl group; $R^2$ represents any of a linear, a branched, or a cyclic alkyl group having 1 to 39 carbon atoms, a linear, a branched, or a cyclic alkenyl group having 2 to 30 carbon atoms, a linear, a branched, or a cyclic alkynyl group having 2 to 30 carbon atoms, a phenyl group, or a naphthyl group, and when $R^2$ represents any of an alkyl group, an alkenyl group, or an alkynyl group, the $R^2$ may include any of a hydroxy group, an ether group, an ester group, or an aromatic group; and each of "a" and "b" independently satisfies the equations $0 \leq a<1.0$, $0<b<1.0$, and $0<a+b\leq1.0$.

The biomedical electrode composition thus obtained can form a living body contact layer for a biomedical electrode that is excellent in conductivity and biocompatibility, is light-weight, can be manufactured at low cost, and can control significant reduction in conductivity even though the biomedical electrode is soaked in water or dried.

The repeating unit "a" is preferably a repeating unit "a1" represented by the following general formula (3),

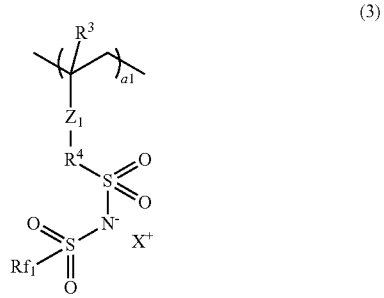

wherein, $R^3$ represents a hydrogen atom or a methyl group; $R^4$ represents any of a single bond, an ester group, or a linear, a branched, or a cyclic hydrocarbon group having 1 to 13 carbon atoms that may include an ether group; $Z_1$ represents any of a single bond, a phenylene group, a naphthylene group, an ether group, an ester group, or an amide group; "a1" satisfies the equation $0<a1<1.0$; and $Rf_1$ and $X^+$ represent the same meanings as before.

When the repeating unit "a" is the repeating unit "a1," the advantageous effects of the present invention can further be enhanced.

Preferably, the polymer compound is copolymerized polymer compound that not only has the repeating unit "a" and the repeating unit "b", but also includes a repeating unit "c" having a fluorine atom or a silicon atom and/or a repeating unit "d" having one or more groups selected from a hydroxy group, carboxyl group, oxirane group, and oxetane group.

The repeating unit "c" is provided with favorable water repellency, thereby preventing changes in conductivity by sweating or washing. The repeating unit "d" is provided with favorable crosslinking properties, thereby preventing peeling from a conductive substrate.

Preferably, the biomedical electrode composition further includes a carbon material, an ITO particle, or a particle coated with a metal selected from silver, gold, platinum, copper, and nickel.

The biomedical electrode composition thus obtained can form a living body contact layer more excellent in conductivity.

Preferably, the carbon material is carbon black and/or carbon nanotube.

Such a carbon material can particularly desirably be used in the biomedical electrode composition of the present invention.

The present invention provides a biomedical electrode including a conductive substrate and a living body contact layer formed on the conductive substrate, wherein the living body contact layer is a cured product of the biomedical electrode composition.

The biomedical electrode thus obtained may include a living body contact layer that is excellent in conductivity and biocompatibility, is light-weight, can be manufactured at low cost, and can control significant reduction in conductivity even though the biomedical electrode is soaked in water or dried.

Preferably, the conductive substrate contains one or more substances selected from gold, silver, silver chloride, platinum, aluminum, magnesium, tin, tungsten, iron, copper, nickel, stainless steel, chromium, titanium, and carbon.

Such a conductive substrate can particularly desirably be used in the biomedical electrode of the present invention.

The present invention provides a method for manufacturing a biomedical electrode including a conductive substrate and a living body contact layer formed on the conductive substrate, including: applying the biomedical electrode composition to the conductive substrate to be cured to form the living body contact layer.

The method for manufacturing a biomedical electrode thus obtained can readily manufacture at low cost a biomedical electrode including a living body contact layer that is excellent in conductivity and biocompatibility, is light-weight, and can control significant reduction in conductivity even though the biomedical electrode is soaked in water or dried.

Preferably, the conductive substrate contains one or more substances selected from gold, silver, silver chloride, platinum, aluminum, magnesium, tin, tungsten, iron, copper, nickel, stainless steel, chromium, titanium, and carbon.

Such a conductive substrate can particularly desirably be used in the method for manufacturing a biomedical electrode of the present invention.

Advantageous Effects of Invention

As described above, the biomedical electrode composition of the present invention can form a living body contact layer that is capable of efficiently transmitting electric signals from the skin to a device (or that is excellent in conductivity), generating no allergy despite its long-time attachment to the skin (or that is excellent in biocompatibility), is light-weight, can be manufactured at low cost, and can control significant reduction in conductivity even though the biomedical electrode is soaked in water or dried. Also, the addition of a carbon material, a metal-coated particle, or an ITO particle can further improve the conductivity, and a combined use of adhesive and elastic polymer compounds can manufacture particularly adhesive and elastic biomedical electrodes. Accordingly, a biomedical electrode including a living body contact layer using such a biomedical electrode composition of the present invention is particularly desirable as a biomedical electrode used in medical wearable devices. The method for manufacturing a biomedical electrode of the present invention can readily manufacture such a biomedical electrode at low cost.

DESCRIPTION OF EMBODIMENTS

Figure 1:
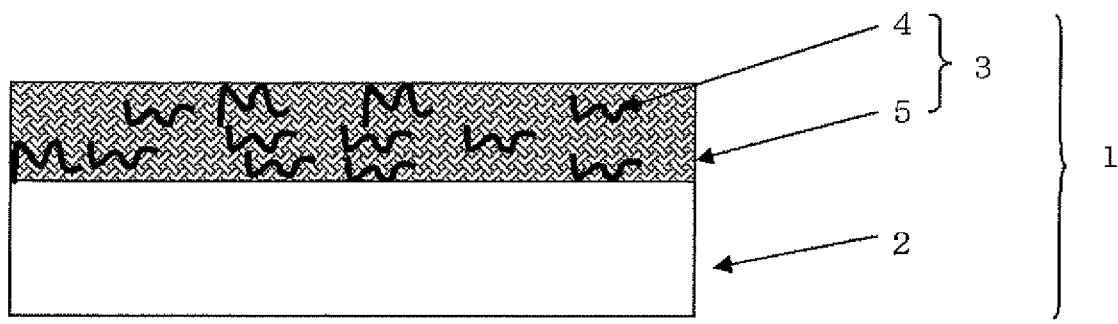
FIG. 1 is a schematic cross-sectional view showing one example of a biomedical electrode of the present invention.

As described above, the development of a biomedical electrode composition capable of forming a living body contact layer for a biomedical electrode that is excellent in conductivity and biocompatibility, is light-weight, can be manufactured at low cost, and can control significant reduction in conductivity even though the biomedical electrode is soaked in water or dried, a biomedical electrode including a living body contact layer formed of the biomedical electrode composition, and a method for manufacturing the biomedical electrode is demanded.

Inventors of the present invention have focused on an alkali-metal salt such as a sodium salt and a potassium salt and an ammonium salt of fluorosulfonic acid and bisfluorosulfonylimide acid, which are commonly known as an ionic liquid blended into a biomedical electrode composition for forming a living body contact layer for a biomedical electrode. However, since these salts are normally highly hydrophilic, a biomedical electrode for forming a living body contact layer from a biomedical electrode composition including these salts is unfortunately subjected to salt extraction by sweating or washing to lower the conductivity. The imide acid having a fluoroalkyl group on both sides of bissulfonylimide acid has higher acidity than afluorosulfonic acid, and even its neutralization by sodium or potassium can significantly stimulate the skin. Furthermore, an ionic liquid having small molecular weight can increasingly cause skin allergy by contact with the skin and subsequent immersion therein.

Meanwhile, since a polymer ionic compound doesn't immerse in the skin, skin allergy is less likely to occur. One known polymer fluorosulfonic acid is a copolymer of tetrafluoroethylene and perfluoro[2-(fluorosulfonylethoxy) propylvinylether] (Nafion as registered trademark). The copolymer having a high proton shift capability is being considered for fuel cell applications. However, since Nafion has extremely high acidity, even its neutralization by a sodium salt, a potassium salt, or an ammonium salt can significantly stimulate the skin. Also, Nafion, which is not adhesive, fails to provide biomedical electrode applications.

A patent document (JP-A-2012-92088) proposes an antibacterial agent composition, including a polymer obtained by copolymerizing methide acid. However, methide acid has acidity high enough to kill bacteria like Nafion, which is problematic for biomedical electrode applications. On the other hand, the use of a sodium salt of polymethacrylic acid as a biomedical electrode can unfortunately cause low conductivity. Accordingly, a neutralization salt of a high-acidity acid is needed to ensure high ion conductivity. As a result, the development of materials for satisfying both acidity and biocompatibility is demanded.

Inventors of the present invention have carried out an extended investigation and developed an acid having lower acidity than bissulfonylimide acid having fluoroalkyl groups on both sides, or a bissulfonylimide acid having a fluoroalkyl group on one side only. Subsequently, they tried to obtain a polymer of the bissulfonylimide acid in order to increase the molecular weight of the bissulfonylimide acid. A biomedical electrode, including a polymer of an alkali-metal salt or an ammonium salt of fluoroalkylated bissulfonylimide acid on either side has no solubility into water. Therefore, they believed that there is no decline in conductivity due to salt extraction by sweating or no rough skin. In fact, a monomer of an alkali-metal salt or an ammonium salt of fluoroalkylated bissulfonylimide acid on either side having a polymerizable double bond is synthesized, and the product is polymerized to obtain a polymer. It was found that a biomedical electrode obtained by using the polymer satisfies both conductivity and biocompatibility, and even though the biomedical electrode is soaked in water or dried, there are no changes in conductivity. Using a polymer obtained by copolymerizing a monomer for copolymers providing a repeating unit giving adhesive capability, in addition to the above monomer, a biomedical electrode constantly attached to the skin capable of stably obtaining electric signals for a long period of time can be obtained. Based on that information, the present invention was accomplished.

Specifically, the present invention provides a biomedical electrode composition including a polymer compound having both an ionic repeating unit "a" and a repeating unit "b" of (meth)acrylate, wherein the ionic repeating unit "a" is a repeating unit of a sodium salt, a potassium salt, or an ammonium salt including a partial structure represented by the following general formula (1), and the repeating unit "b" of (meth)acrylate is a repeating unit represented by the following general formula (2), (1)

$$\left(\begin{array}{c} O \\ \| \\ -S-N^- \\ \| \\ O \end{array} \begin{array}{c} X^+ \\ \\ S=O \\ \| \\ O \end{array} Rf_1 \right)$$

(2)

$$\left(\begin{array}{c} R^1 \\ | \\ \\ \\ O \end{array}\right)_b$$
$$\begin{array}{c} | \\ O \\ | \\ R^2 \end{array}$$

wherein, $Rf_1$ represents a linear, or a branched alkyl group having 1 to 4 carbon atoms, having at least one fluorine atom; $X^+$ represents any of a sodium ion, a potassium ion, or an ammonium ion; $R^1$ represents a hydrogen atom or a methyl group; $R^2$ represents any of a linear, a branched, or a cyclic alkyl group having 1 to 39 carbon atoms, a linear, a branched, or a cyclic alkenyl group having 2 to 30 carbon atoms, a linear, a branched, or a cyclic alkynyl group having 2 to 30 carbon atoms, a phenyl group, or a naphthyl group, and when $R^2$ represents any of an alkyl group, an alkenyl group, or an alkynyl group, the $R^2$ may include any of a hydroxy group, an ether group, an ester group, or an aromatic group; and each of "a" and "b" independently satisfies the equations $0<a<1.0$, $0<b<1.0$, and $0<a+b\leq1.0$.

The present invention will be described in detail, but the present invention is not restricted thereto.

Biomedical Electrode Composition

The biomedical electrode composition of the present invention includes, as an adhesive polymer ionic material, a polymer compound having both an ionic repeating unit "a" and a repeating unit "b" of (meth)acrylate. Each of the components will be described in more detail.

Polymer Compound

The polymer compound in the biomedical electrode composition of the present invention is a polymer salt blended as a conductive material, having both an ionic repeating unit "a" and a repeating unit "b" of (meth)acrylate.

The ionic repeating unit "a" is a repeating unit of a sodium salt, a potassium salt, or an ammonium salt including a partial structure represented by the following general formula (1), (1)

$$\left(\begin{array}{c} O \\ \| \\ -S-N^- \\ \| \\ O \end{array} \begin{array}{c} X^+ \\ \\ S=O \\ \| \\ O \end{array} Rf_1 \right)$$

wherein, $Rf_1$ represents a linear, or a branched alkyl group having 1 to 4 carbon atoms, having at least one fluorine atom; $X^+$ represents any of a sodium ion, a potassium ion, or an ammonium ion; and "a" satisfies the equation $0<a<1.0$.

The repeating unit "a" is preferably a repeating unit "a1" represented by the following general formula (3), (3)

$$\left(\begin{array}{c} R^3 \\ | \\ \\ \\ Z_1 \\ | \\ R^4 \end{array}\right)_{a1}$$

wherein, $R^3$ represents a hydrogen atom or a methyl group; $R^4$ represents any of a single bond, an ester group, or a linear, a branched, or a cyclic hydrocarbon group having 1 to 13 carbon atoms that may include an ether group; $Z_1$ represents any of a single bond, a phenylene group, a naphthylene group, an ether group, an ester group, or an amide group; a1 satisfies the equation $0<a1<1.0$; and $Rf_1$ and $X^+$ represent the same meanings as before.

Illustrative example of the sulfonimide salt monomer for obtaining a repeating unit "a1" represented by the general formula (3) includes the following monomers.

-continued
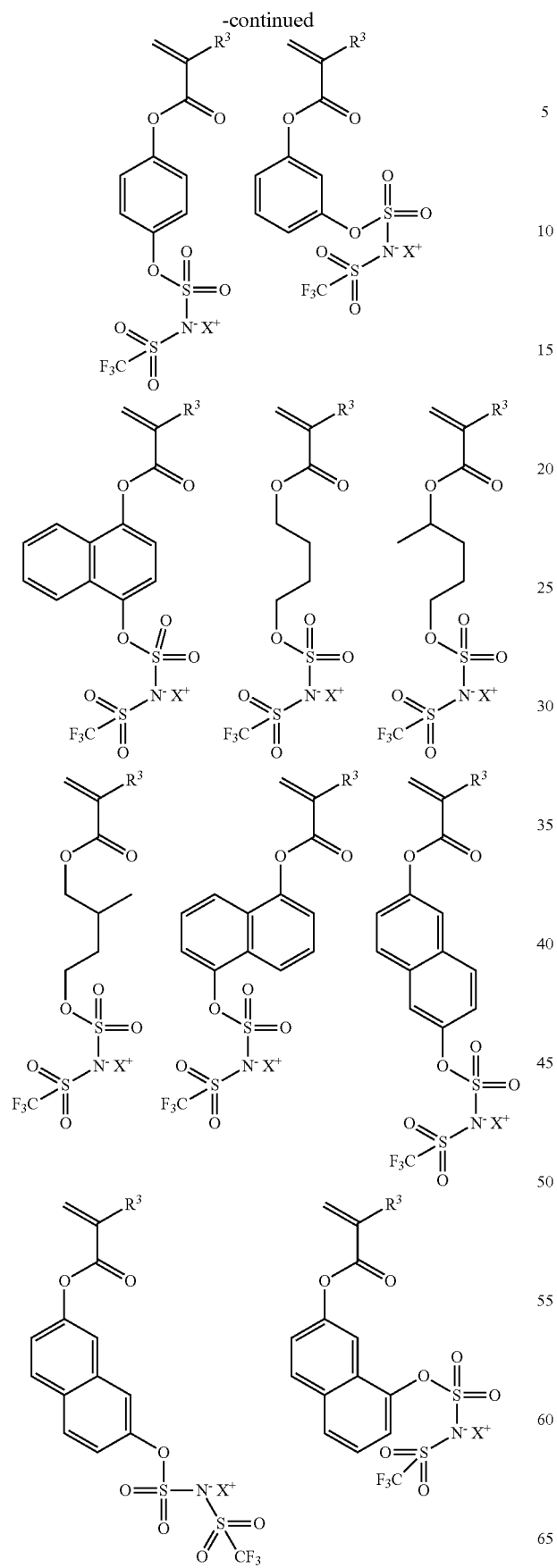
-continued
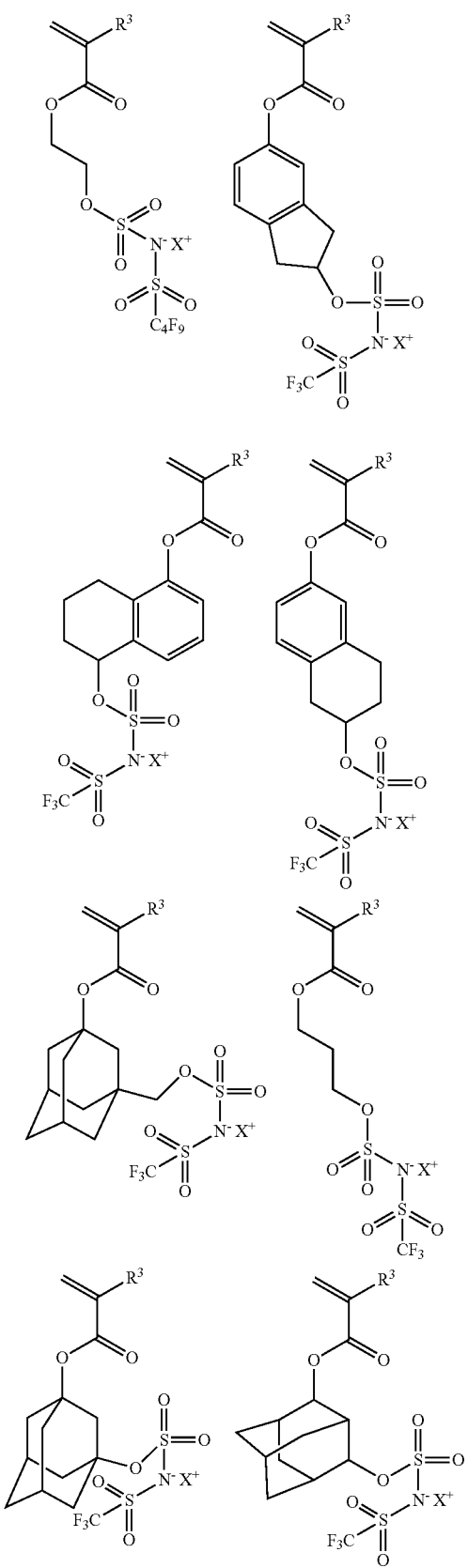

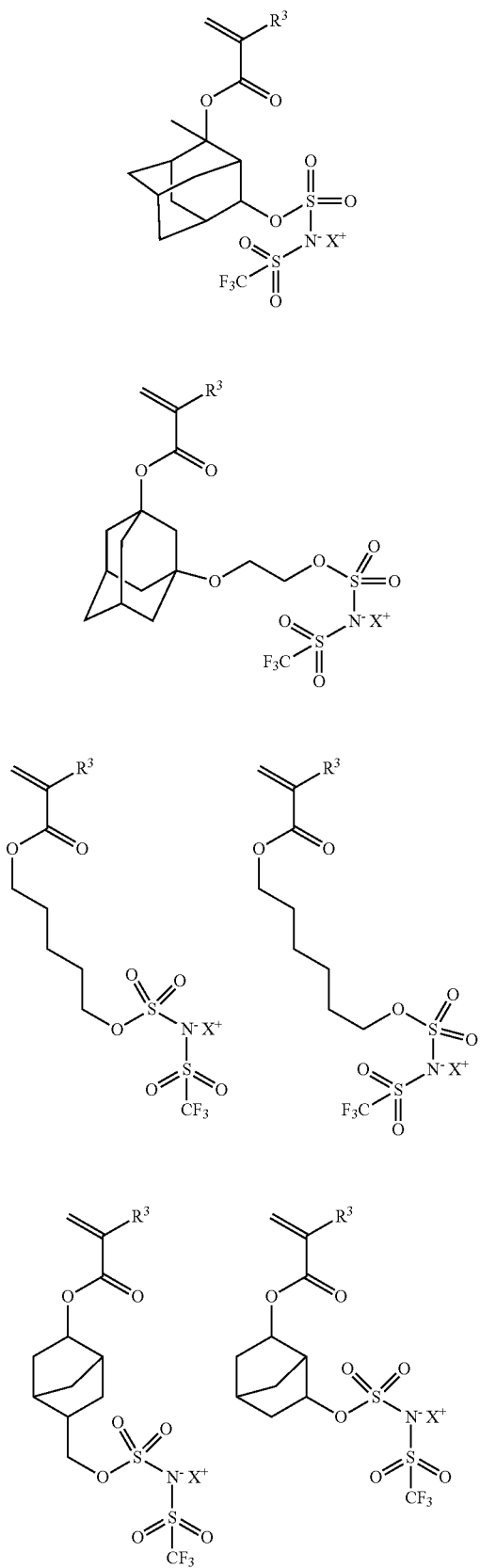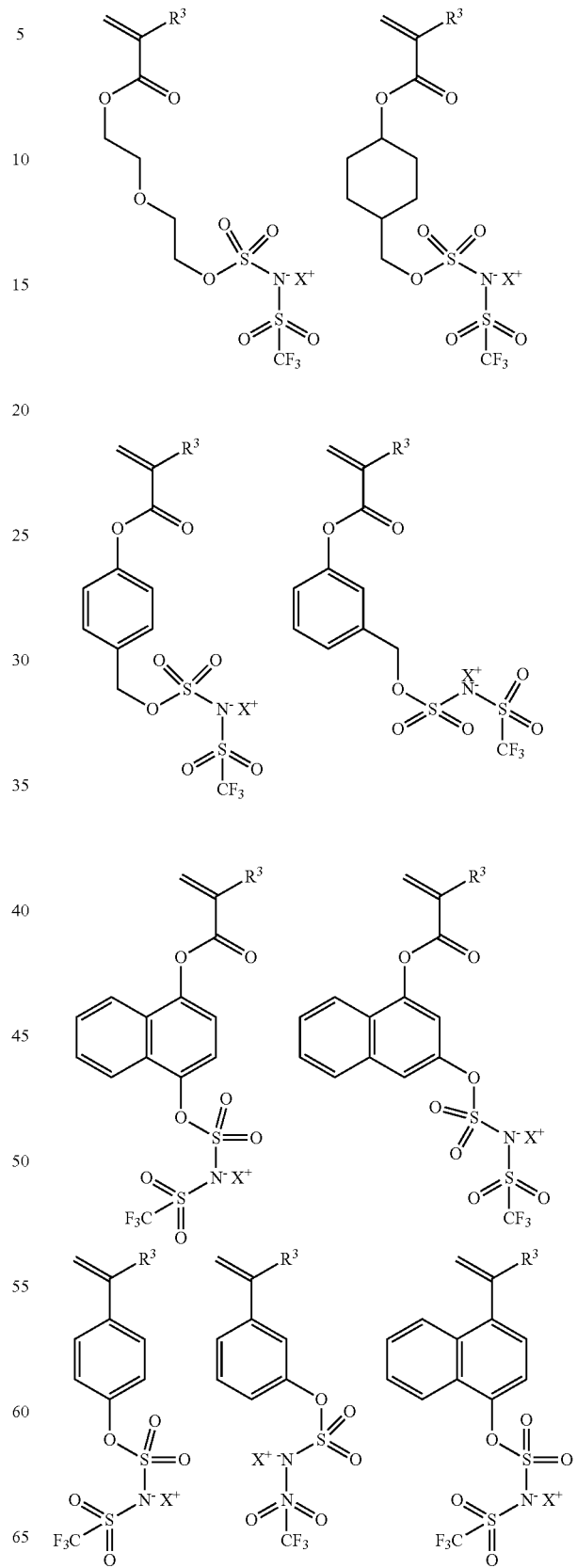

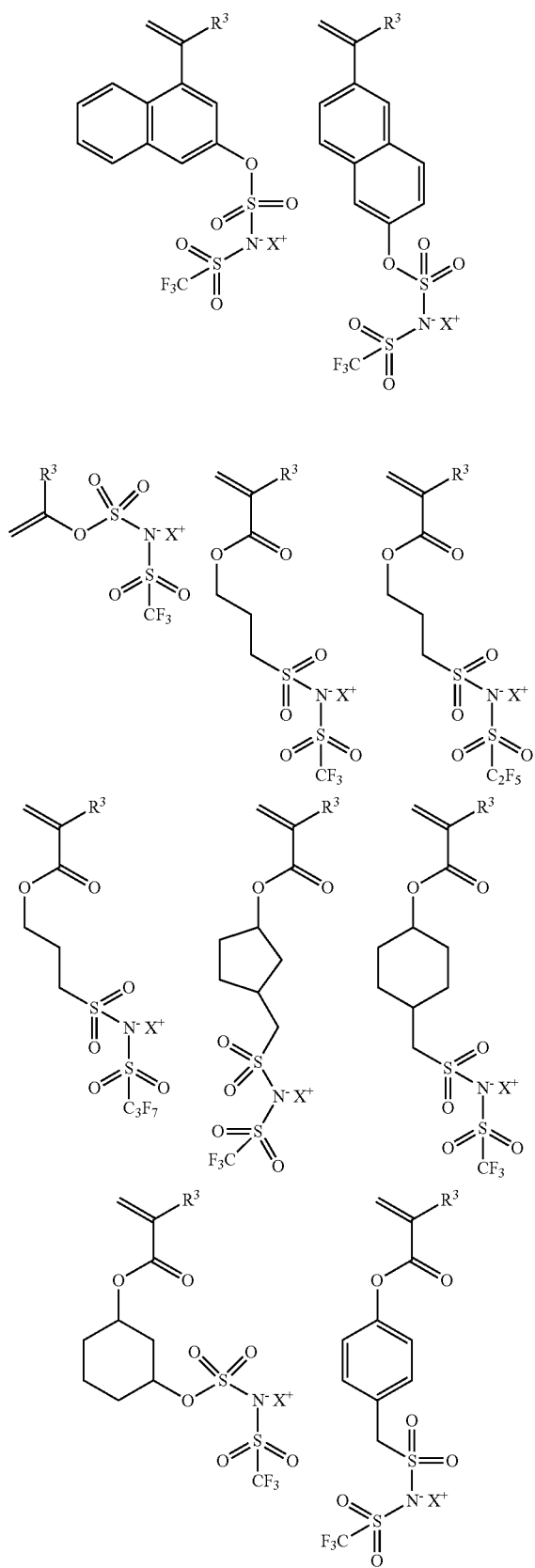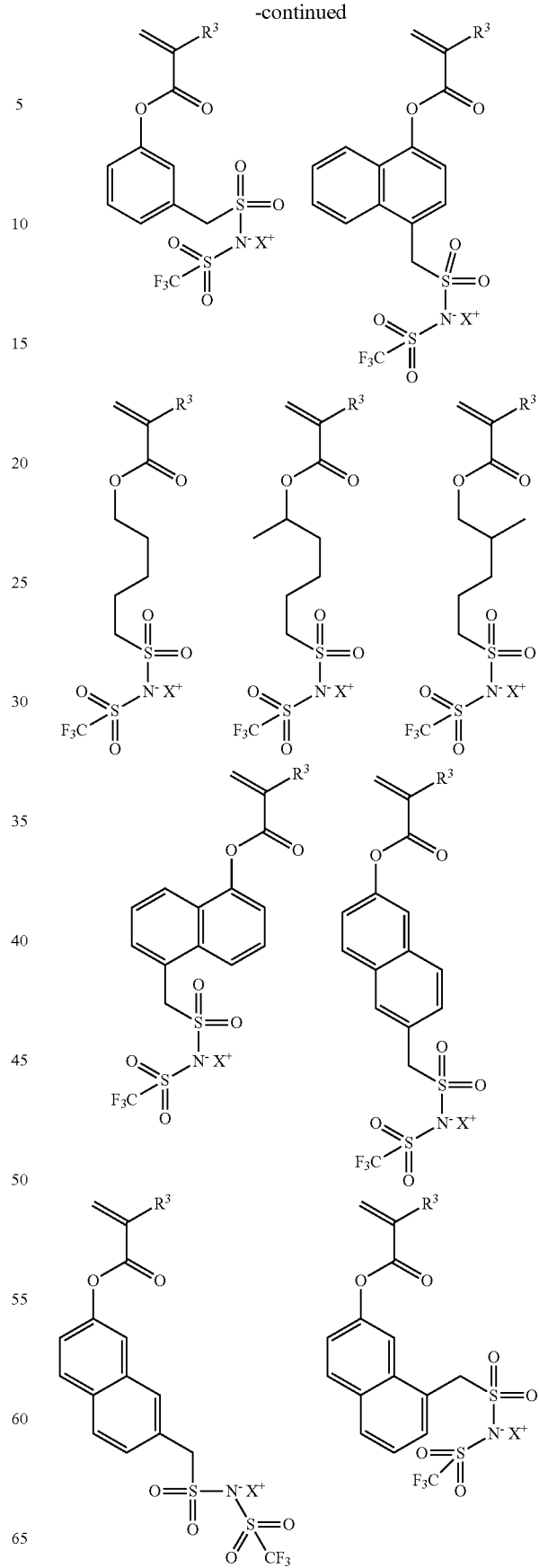

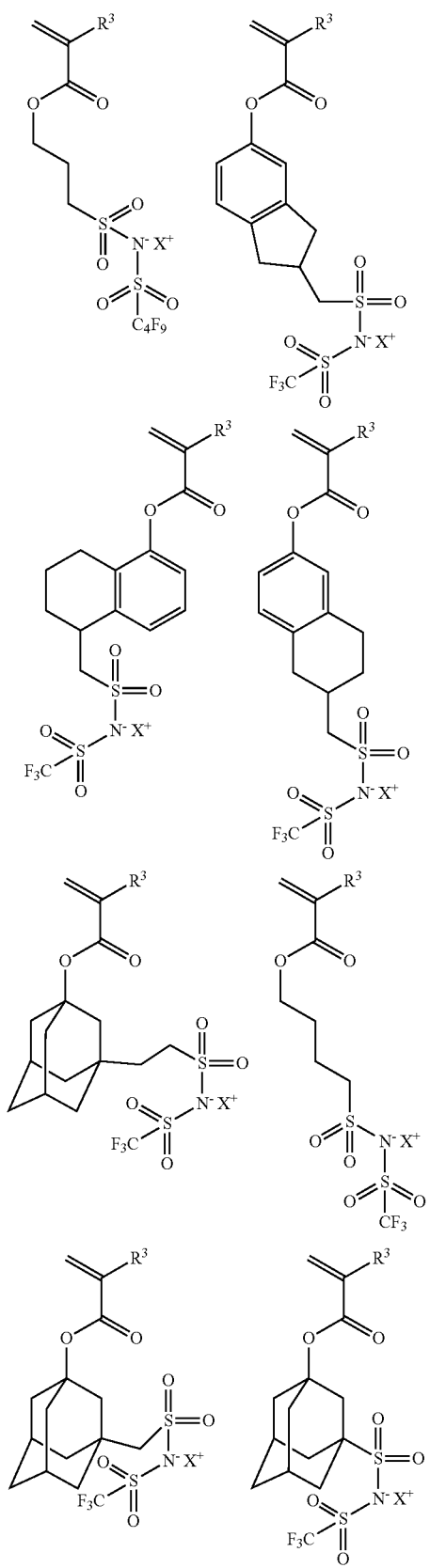
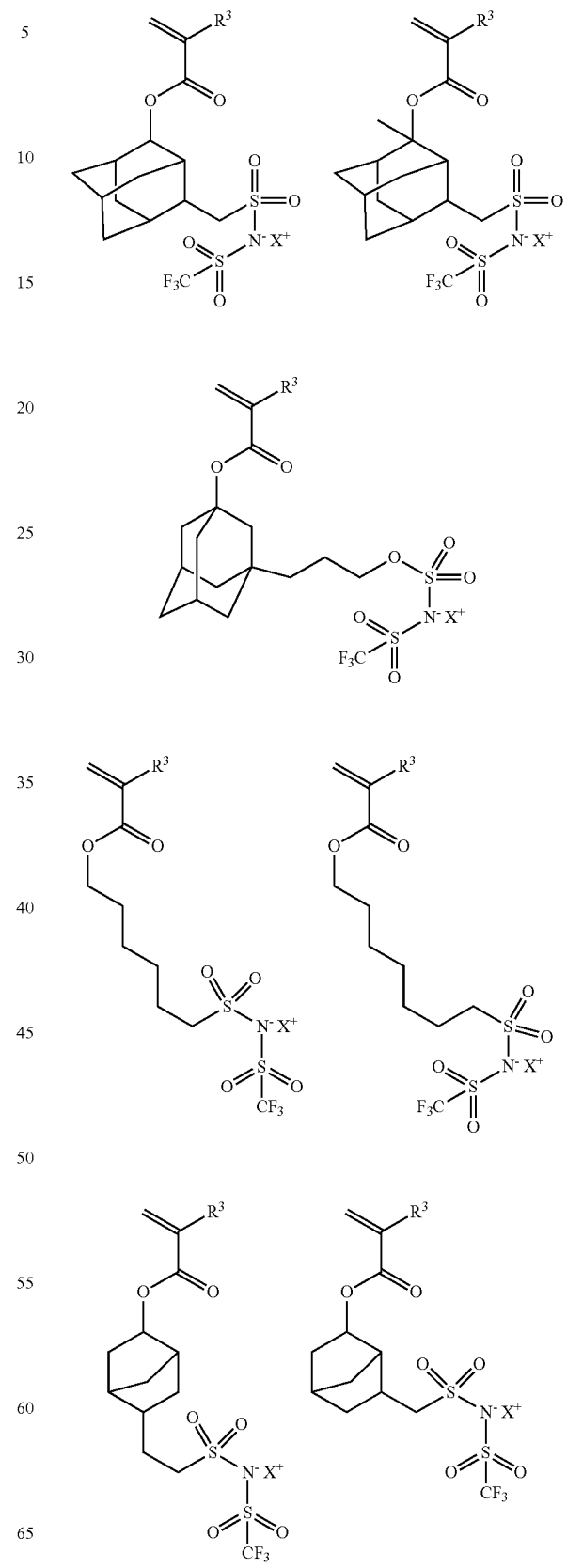

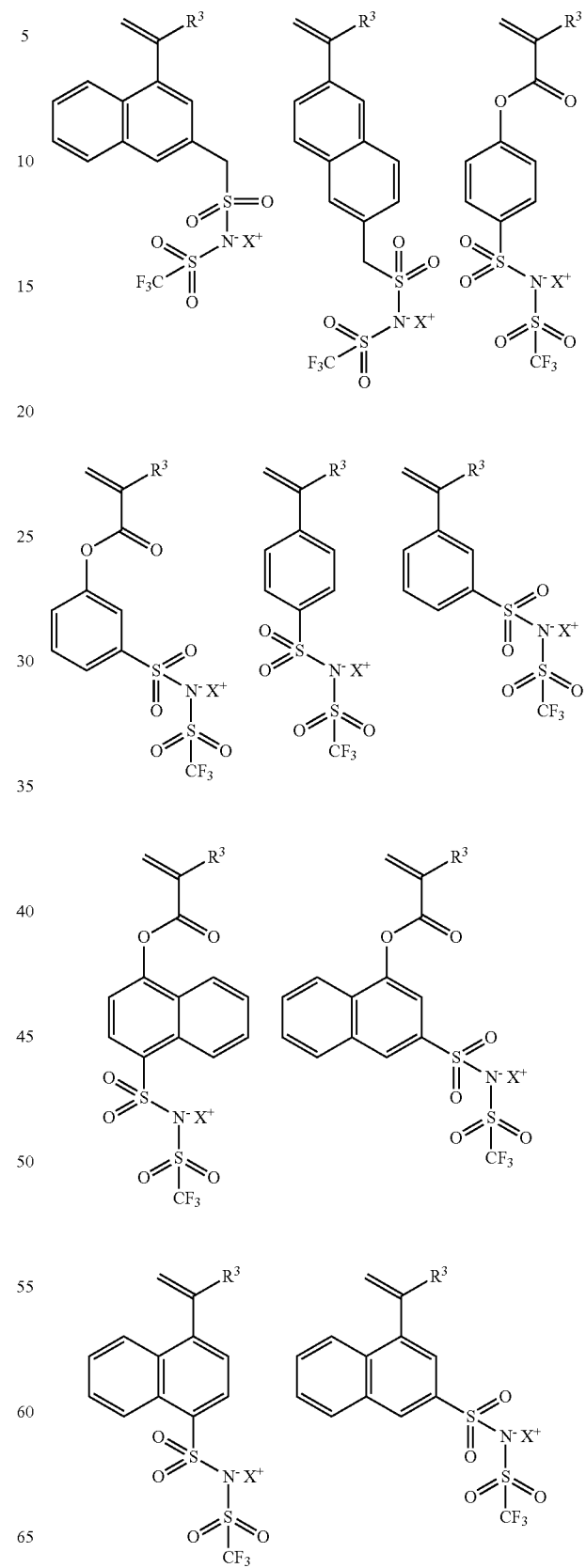

-continued

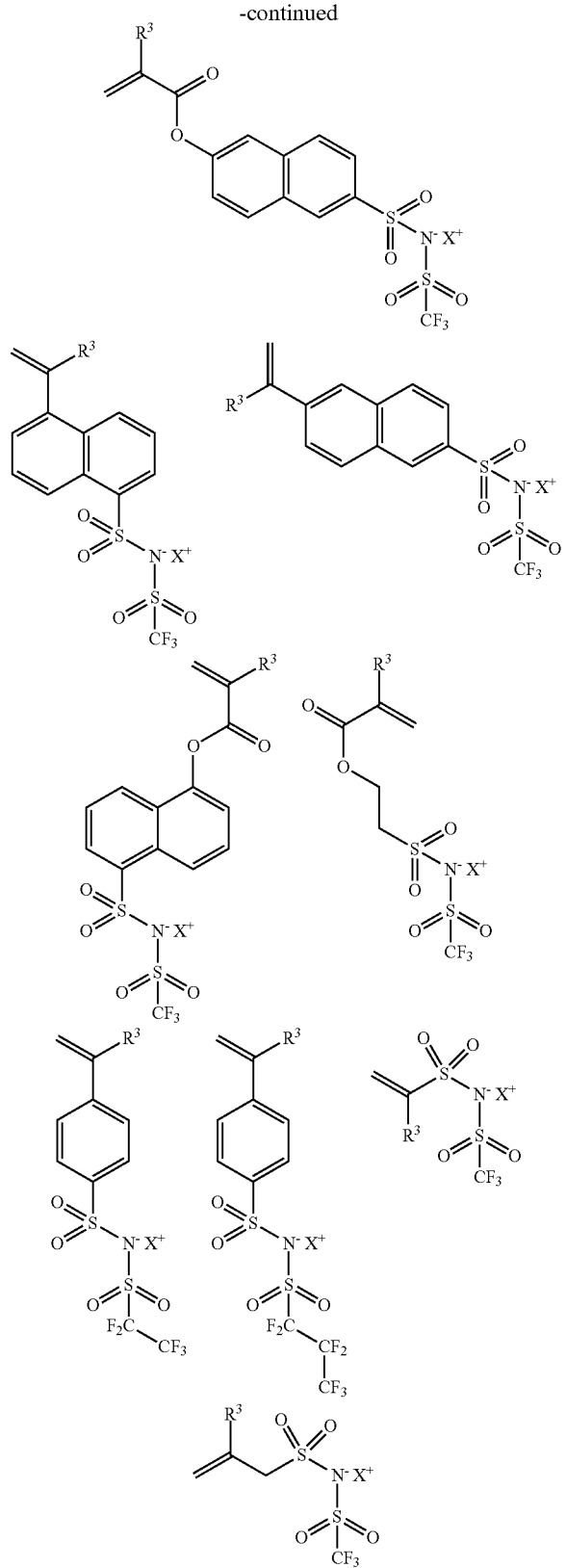

wherein, R³ and X⁺ represent the same meanings as before.

In the present invention, X⁺ in the general formula (1) represents any of a sodium ion, a potassium ion, and an ammonium ion. When X⁺ is an ammonium ion, it may be represented by the following general formula (4),

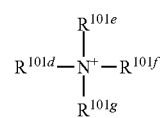

(4)

wherein, each of $R^{101d}$, $R^{101e}$, $R^{101f}$, and $R^{101g}$ independently represents any of a hydrogen atom, a linear, a branched, or a cyclic alkyl group, an alkenyl group, an oxoalkyl group, or an oxoalkenyl group having 1 to 12 carbon atoms, an aryl group having 6 to 20 carbon atoms, an aralkyl group or an aryloxoalkyl group having 7 to 12 carbon atoms a part or all of whose hydrogen atoms may be substituted by an alkoxy group; $R^{101d}$ and $R^{101e}$, or $R^{101d}$, $R^{101e}$, and $R^{101f}$ may be bonded to form a ring along with a nitrogen atom bonded to these, and in this case, $R^{101d}$ and $R^{101e}$, and $R^{101d}$, $R^{101e}$, and $R^{101f}$ form an alkylene group having 3 to 10 carbon atoms, or a heteroaromatic ring having a nitrogen atom in the formula in a ring.

The method for synthesizing a monomer of a sodium salt and a potassium salt to obtain a repeating unit "a1" represented by the general formula (3) may be a method for obtaining the repeating unit "a1" by mixing an ammonium salt of the above sulfonimide with sodium chloride or chloride potassium in an organic solvent. In this case, chloride ammonium generated as a by-product is preferably removed by water cleaning.

The ionic repeating unit "a" in the biomedical electrode composition of the present invention is described in JP-A-5264723. In this patent publication, however, a polymer compound in which ionic repeating units "a" are polymerized is combined with polythiophene, etc. to merely form a transparent conductive film. In fact, the polymer compound is not copolymerized with an adhesive monomer or used in biomedical electrode applications.

The polymer compound in the biomedical electrode composition of the present invention has the repeating unit "a", and as an adhesive repeating unit, a repeating unit "b" of (meth)acrylate represented by the following general formula (2),

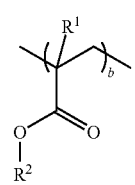

(2)

wherein, R¹ represents a hydrogen atom or a methyl group; R² represents any of a linear, a branched, or a cyclic alkyl group having 1 to 39 carbon atoms, a linear, a branched, or a cyclic alkenyl group having 2 to 30 carbon atoms, a linear, a branched, or a cyclic alkynyl group having 2 to 30 carbon atoms, a phenyl group, or a naphthyl group, and when R² represents any of an alkyl group, an alkenyl group, or an alkynyl group, the R² may include any of a hydroxy group, an ether group, an ester group, or an aromatic group; and b satisfies the equation 0<b<1.0.

The number of carbon atoms of $R^2$ is preferably 4 to 30, and more preferably 6 to 28.
The ratio of the repeating unit "a" and the repeating unit "b" satisfies the equations $0<a<1.0$, $0<b<1.0$, and $0<a+b\leq1.0$.
Illustrative example of the monomer for obtaining the repeating unit "b" includes the following monomers.
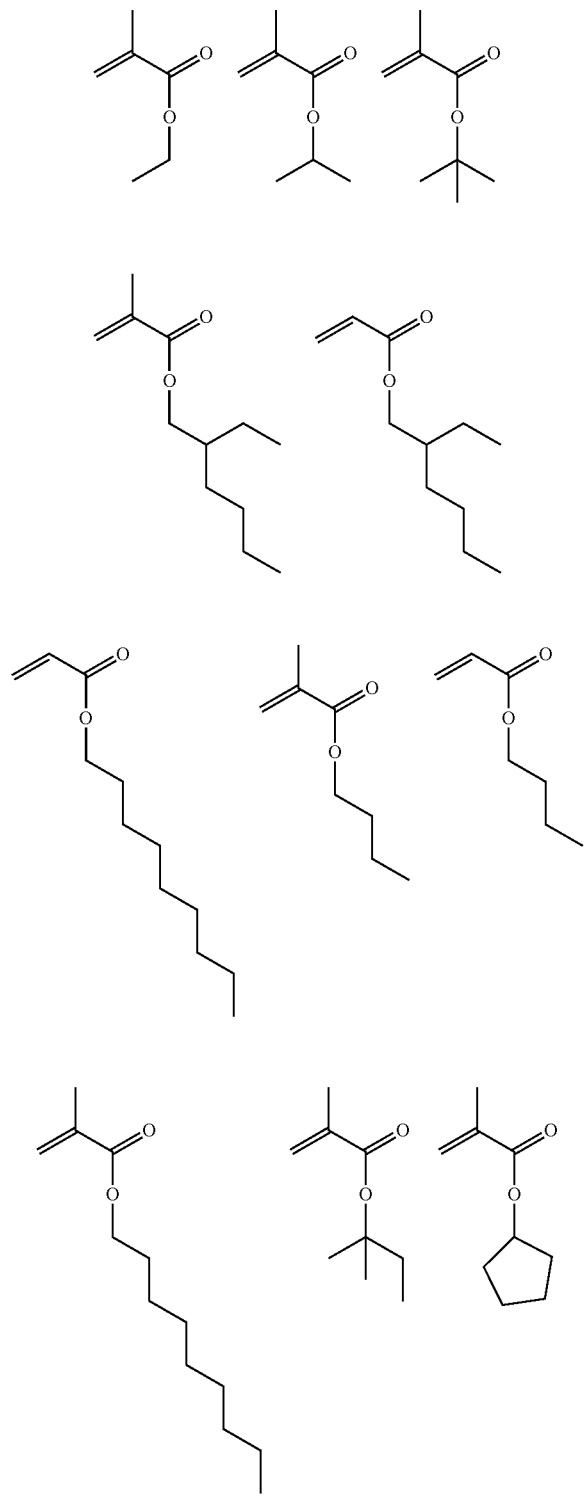
-continued
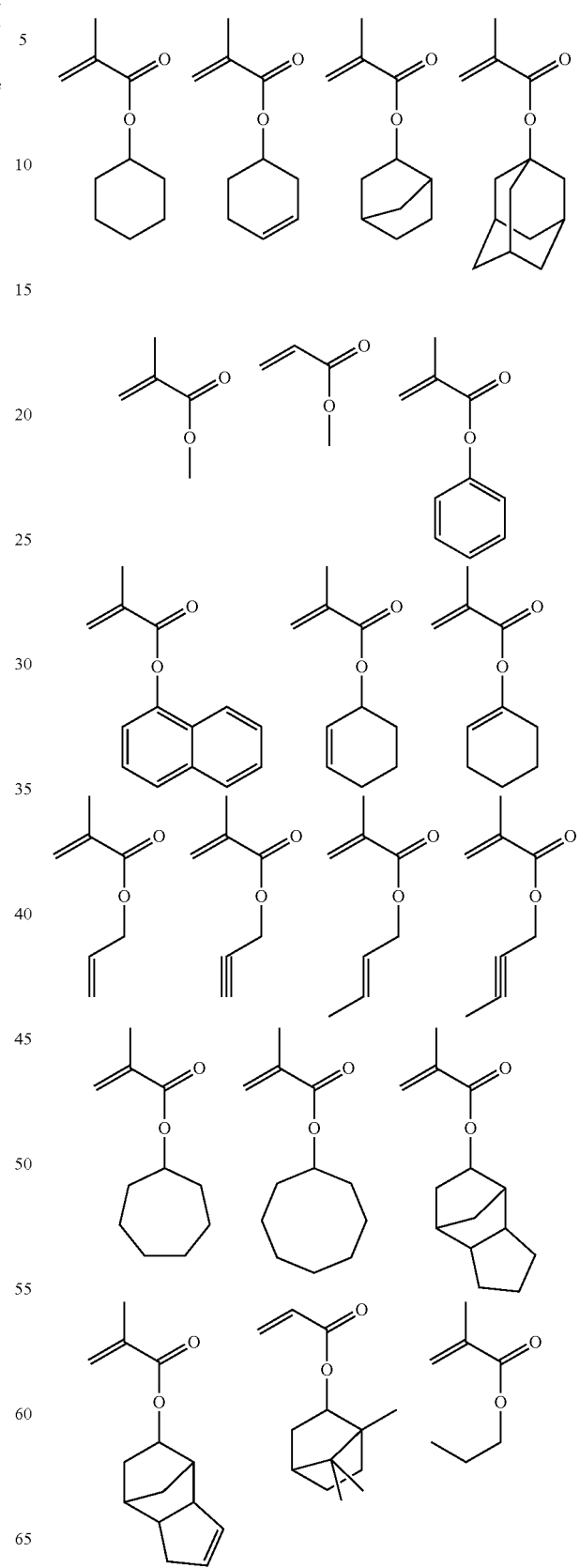

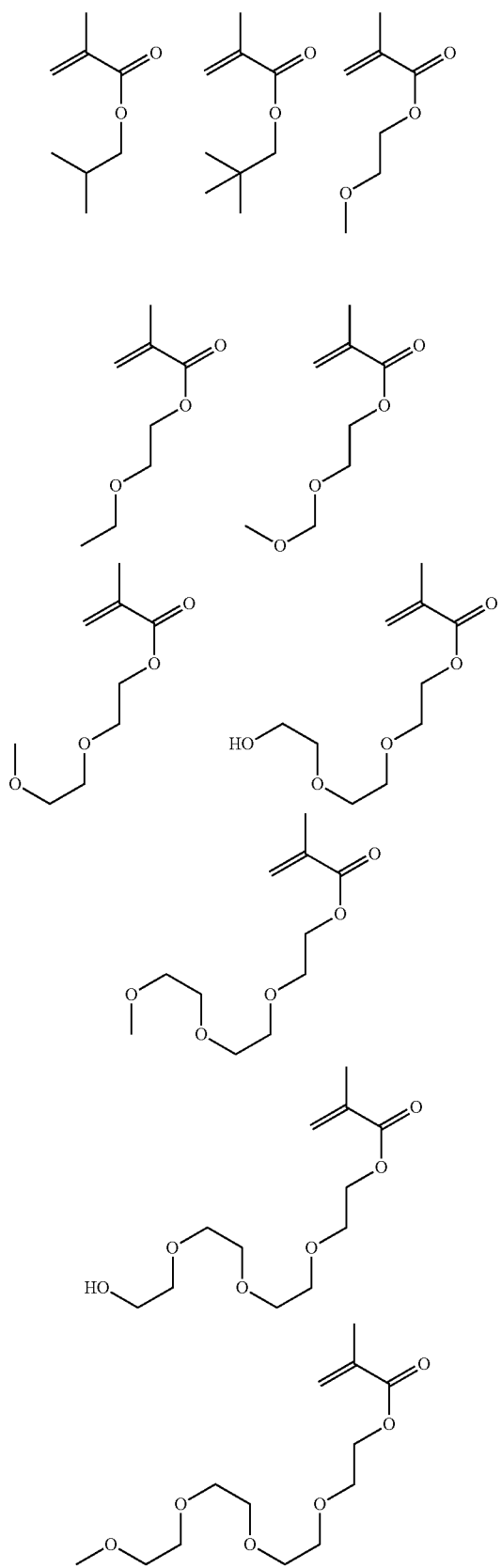
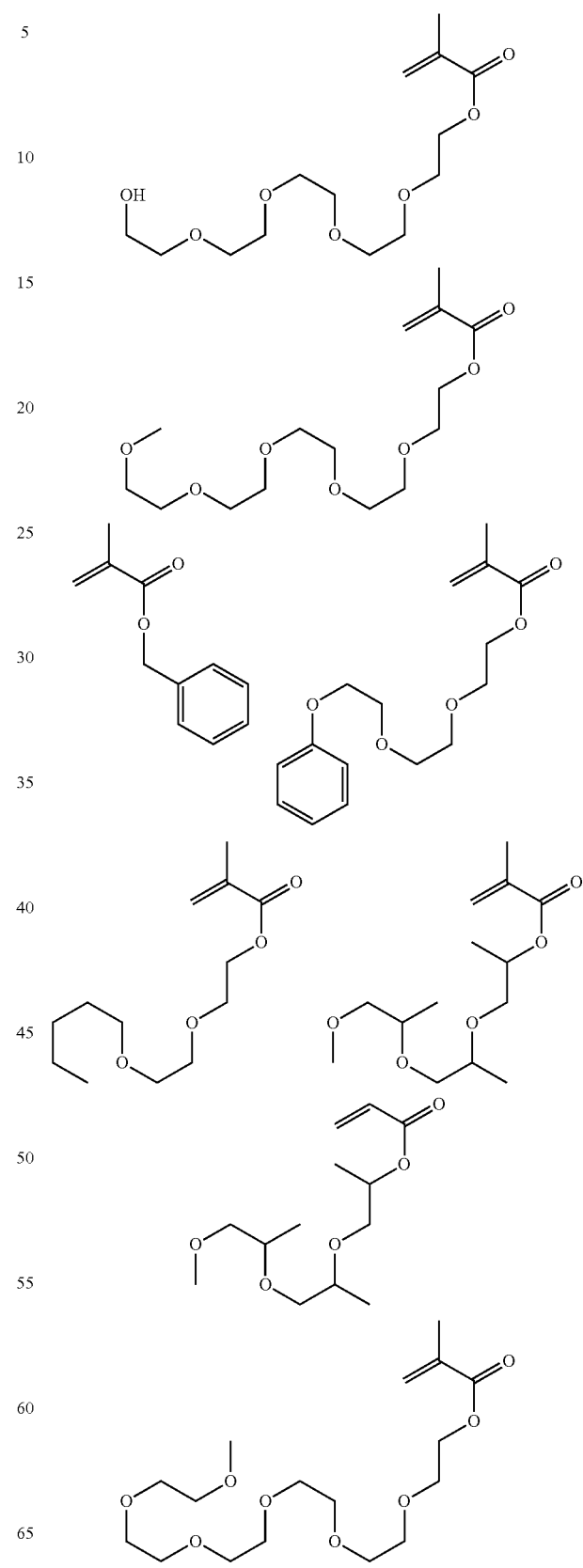

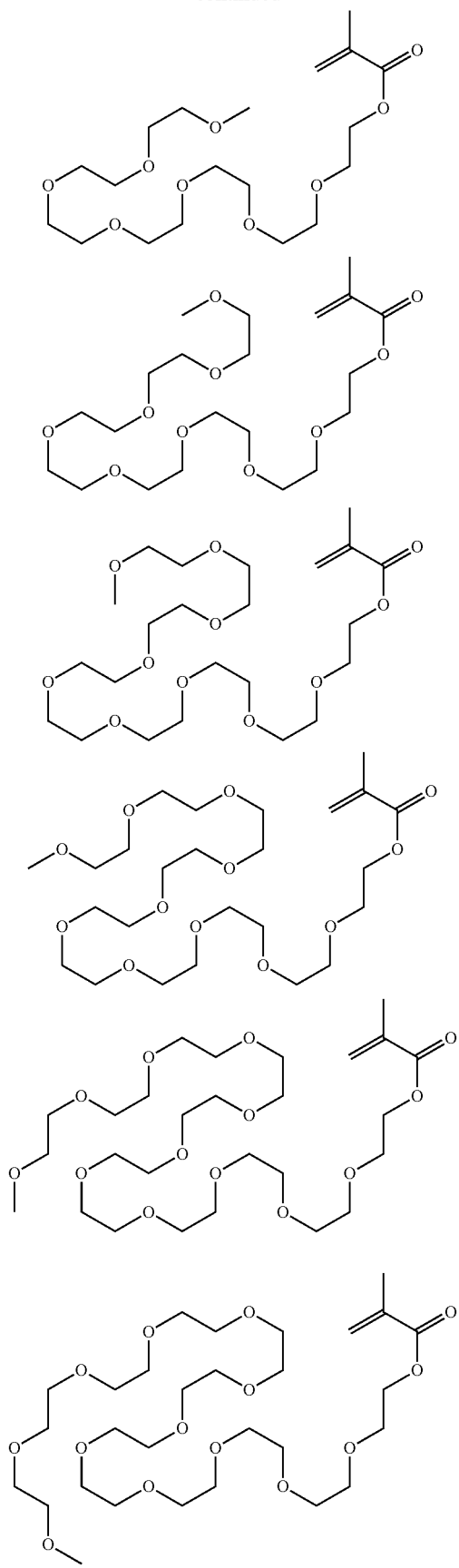
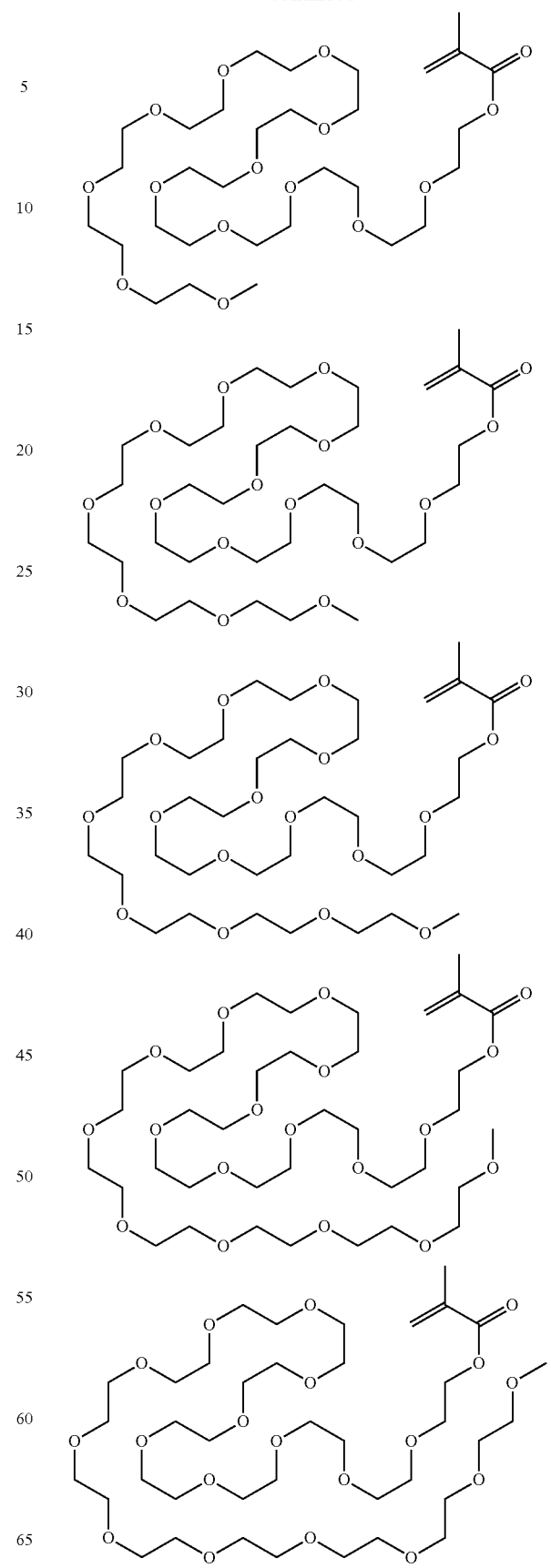

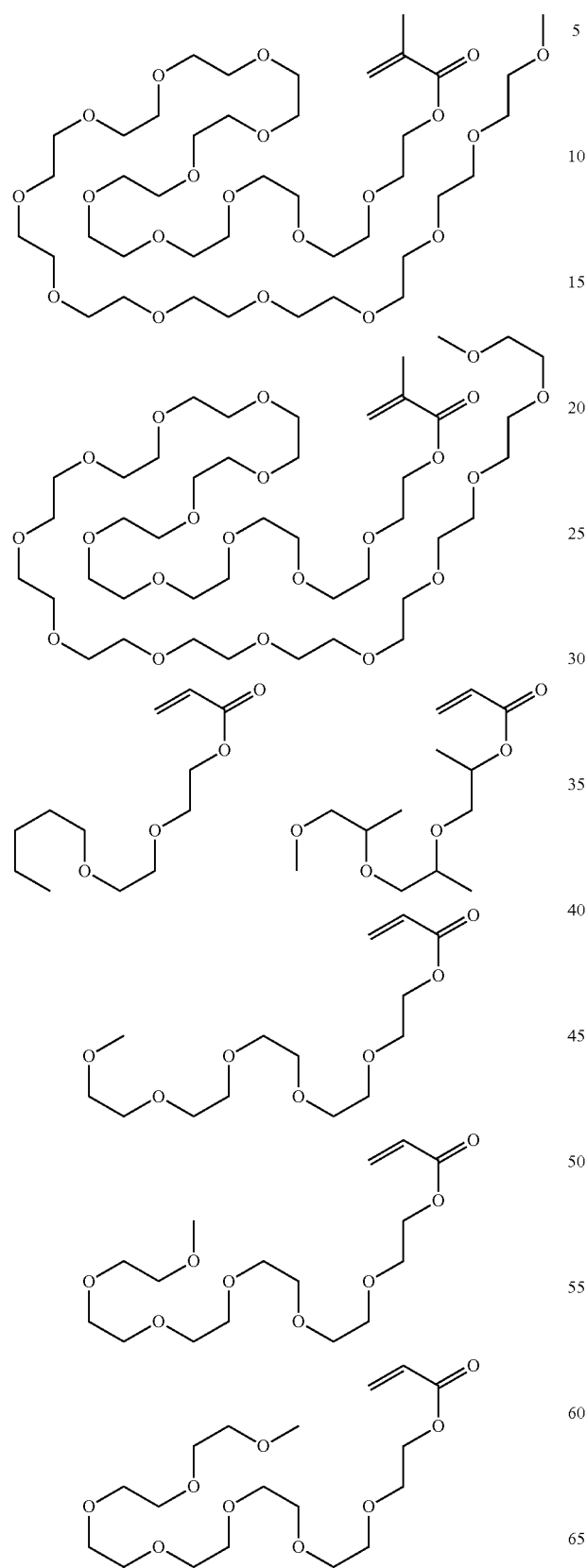
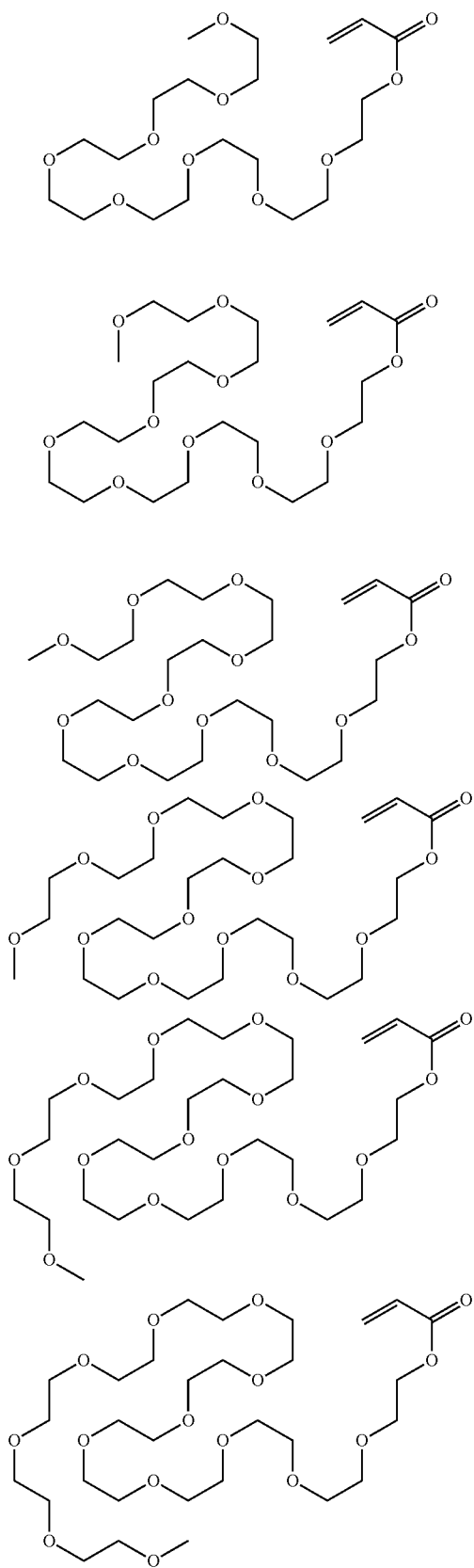

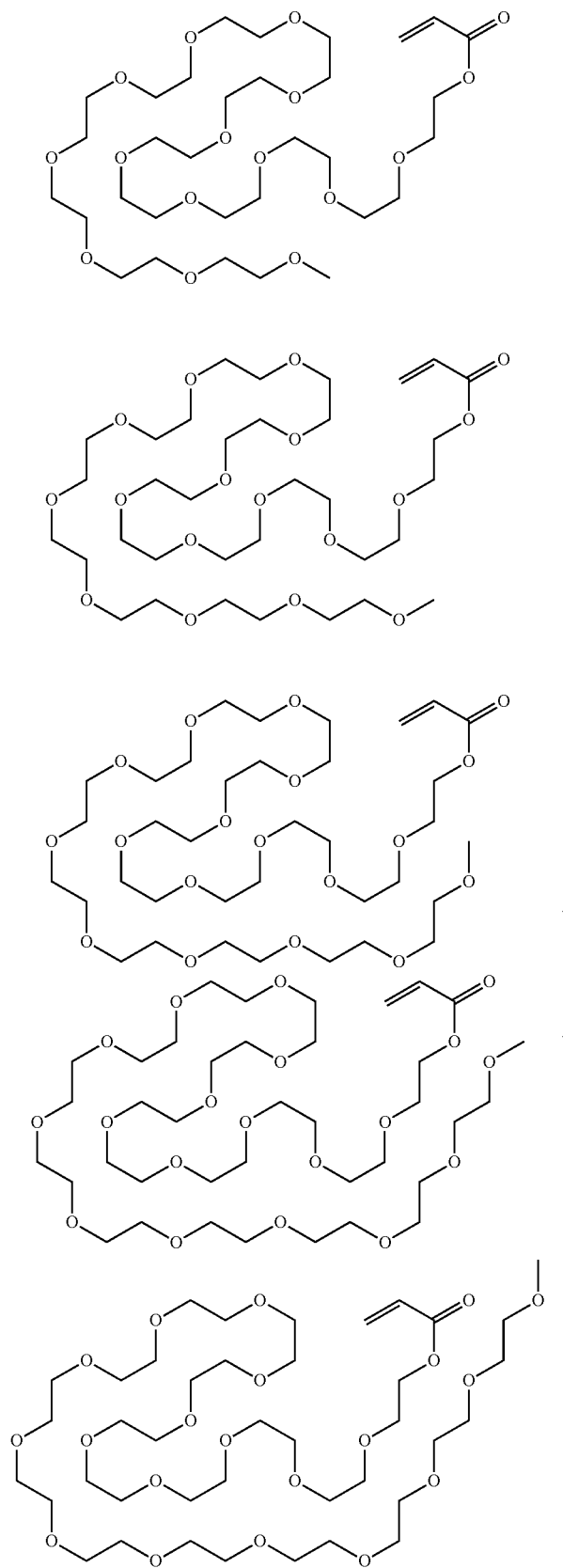
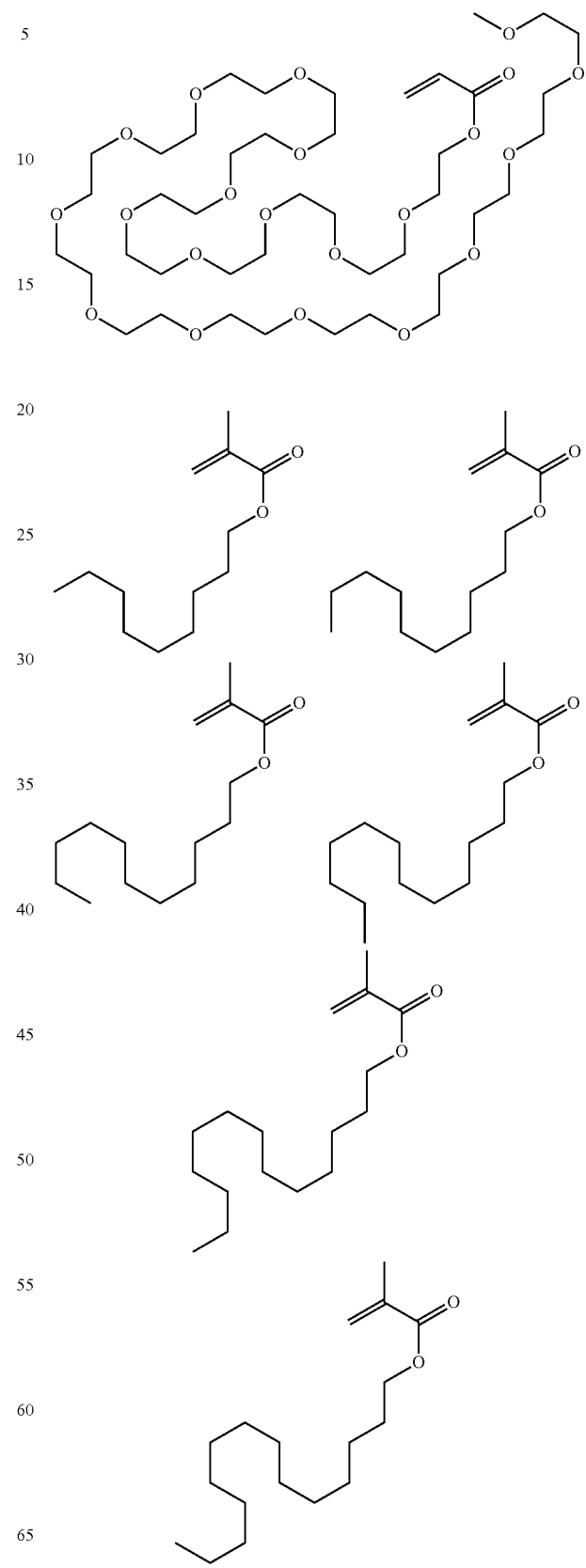

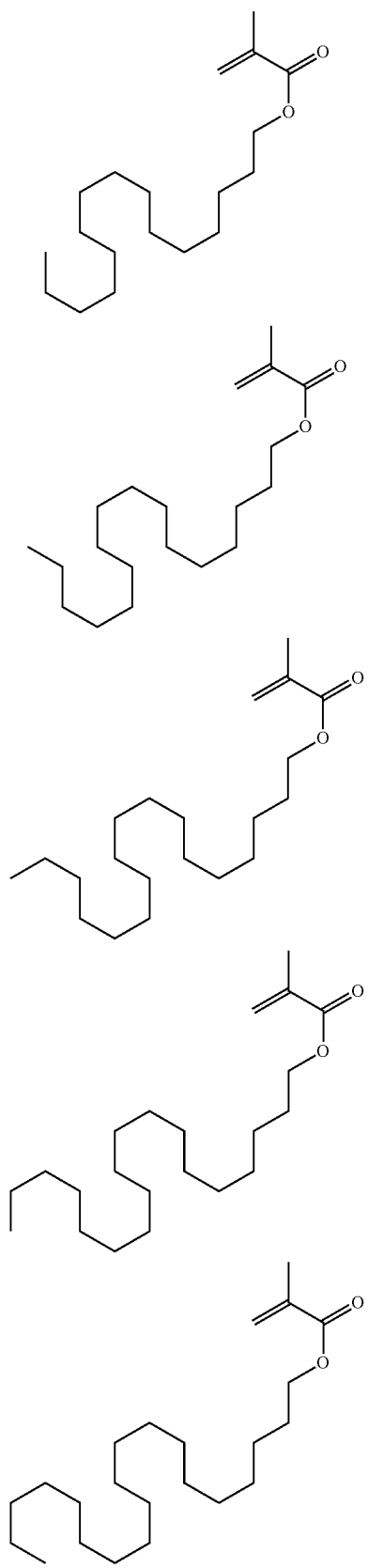
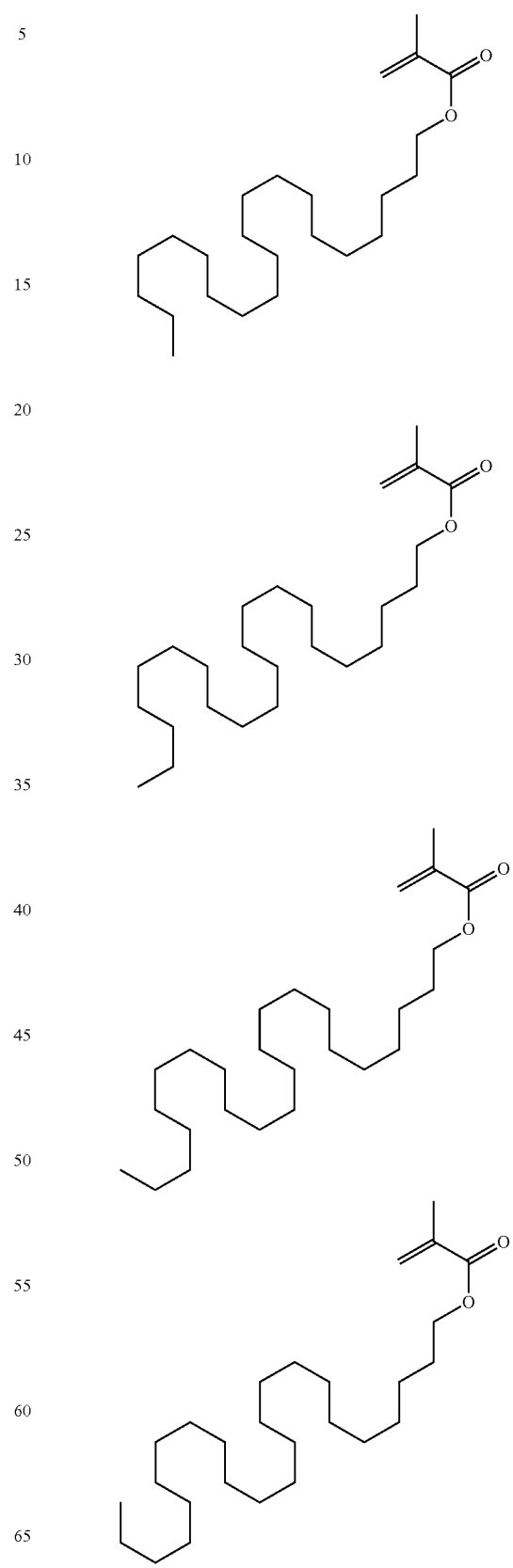

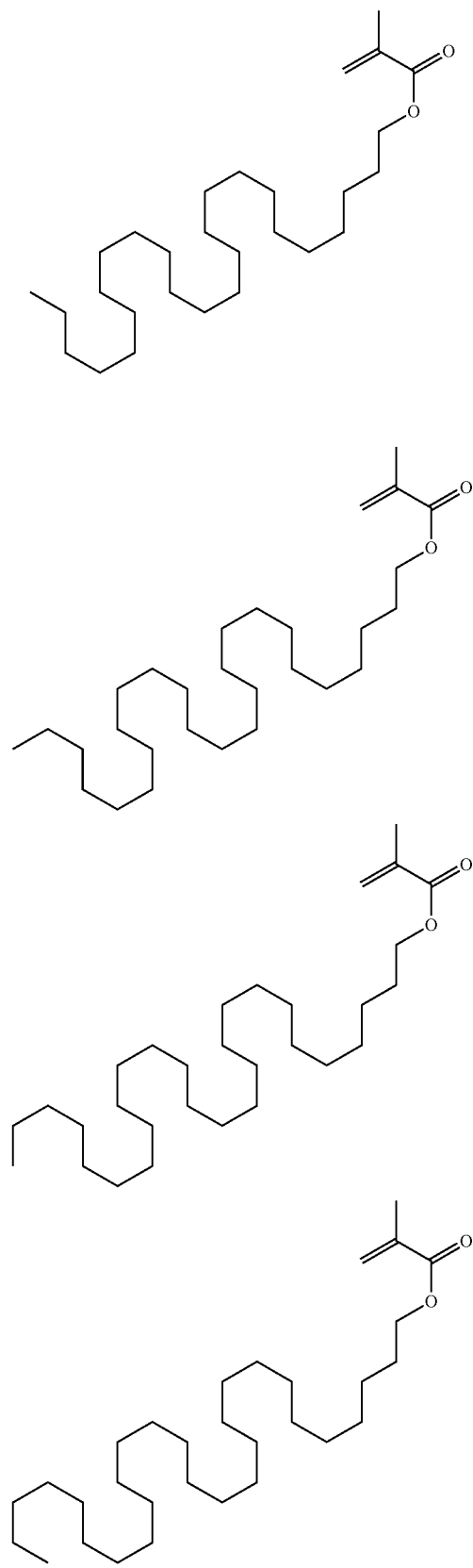
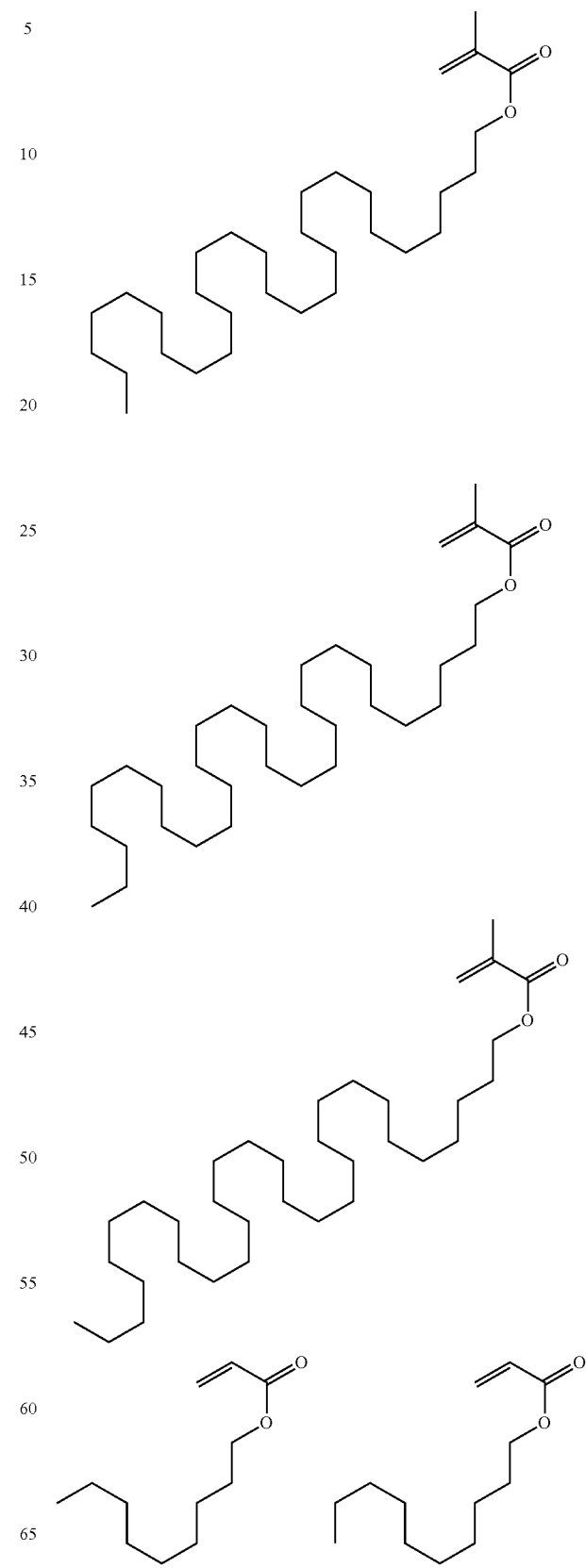

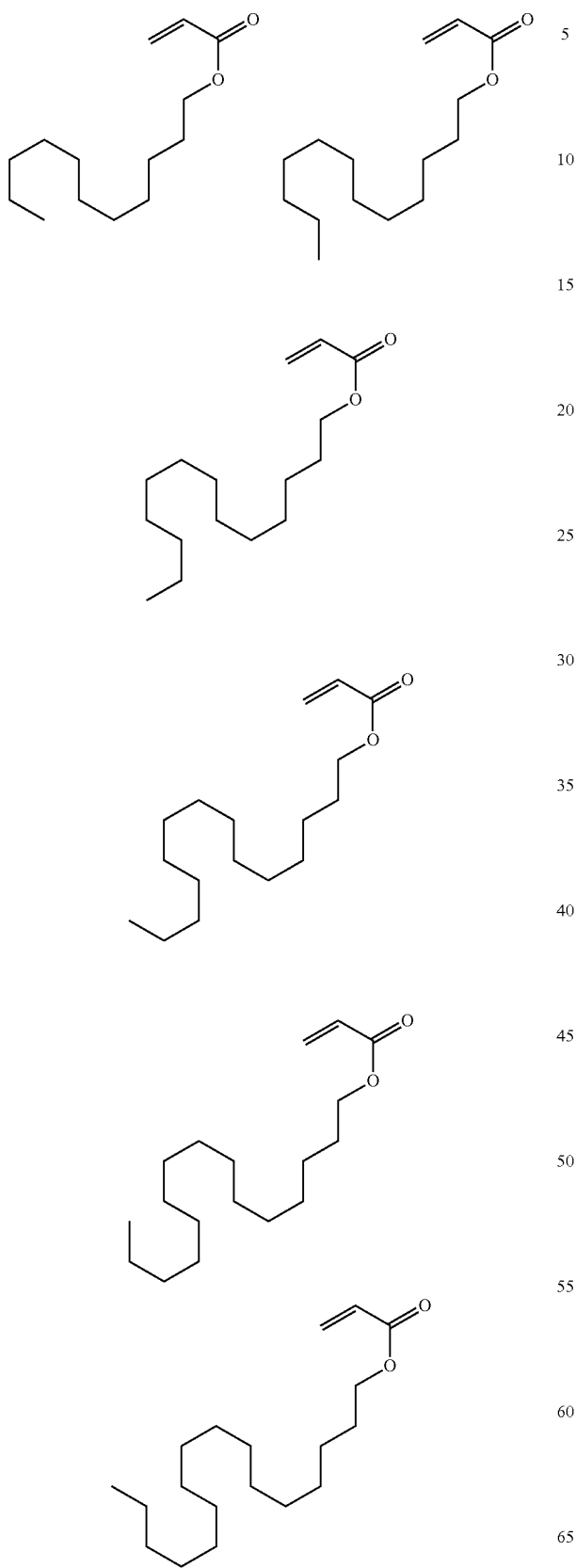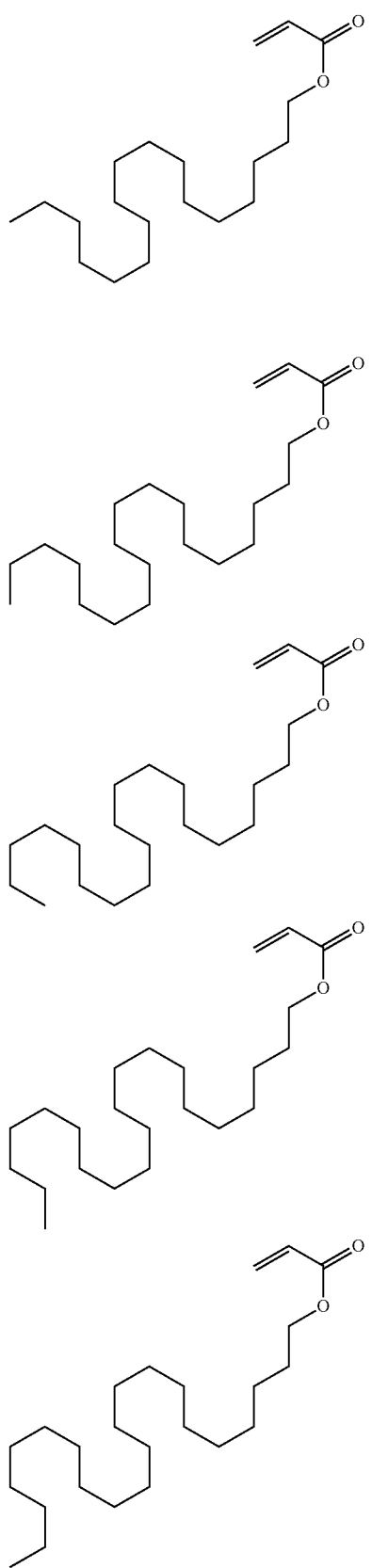

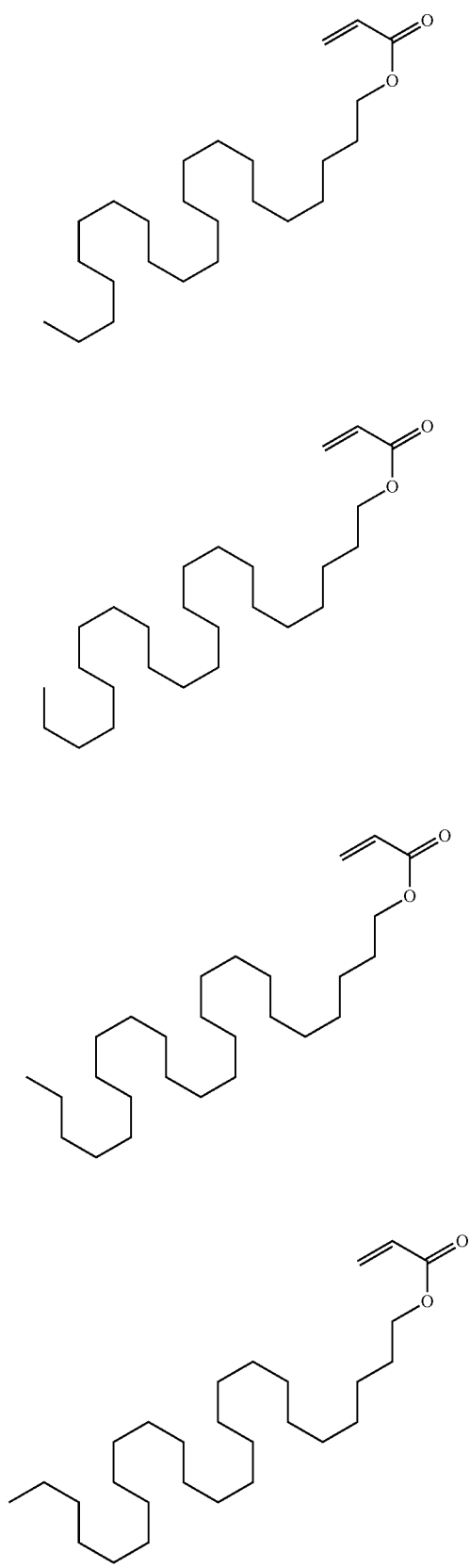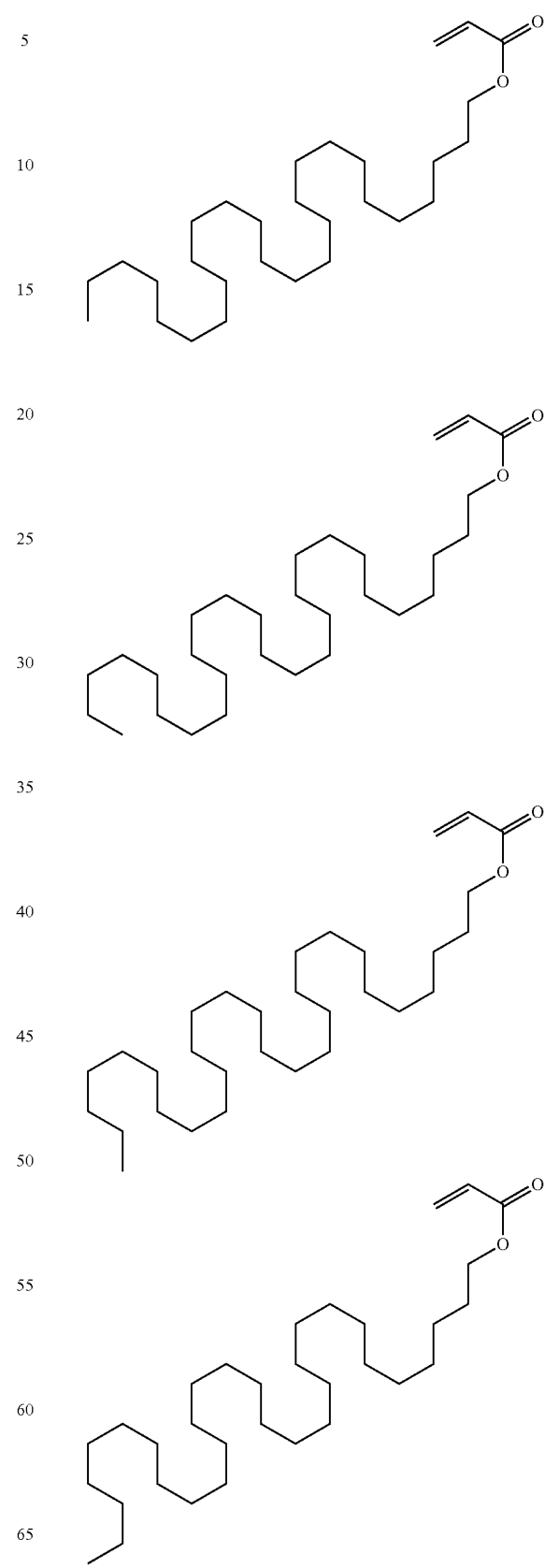

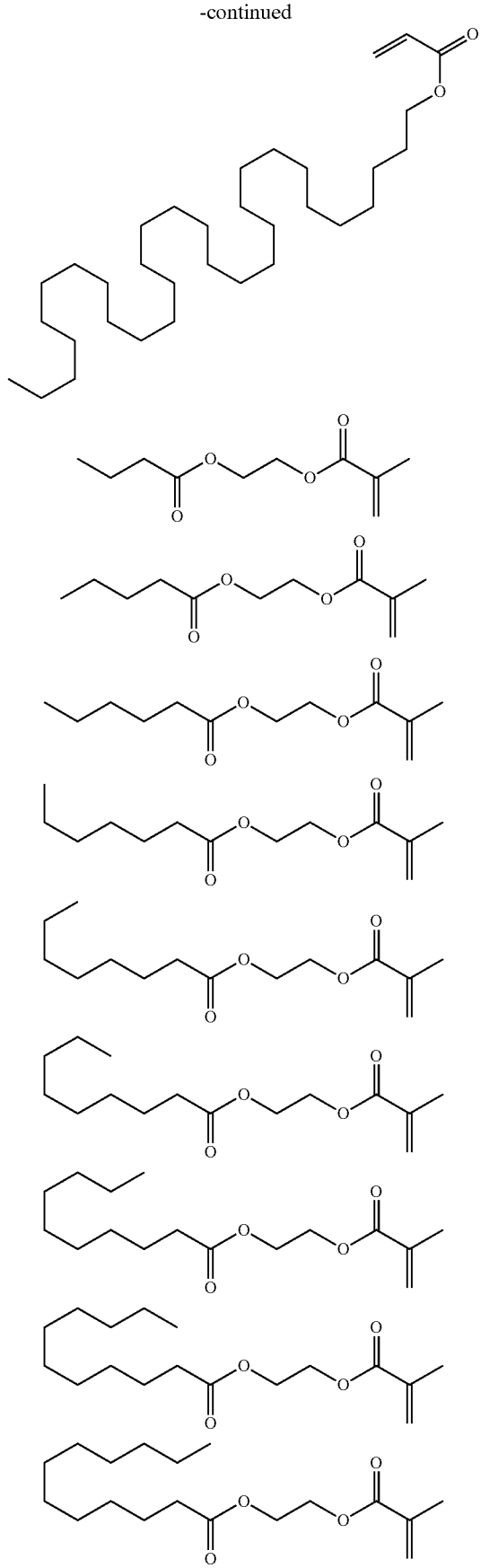
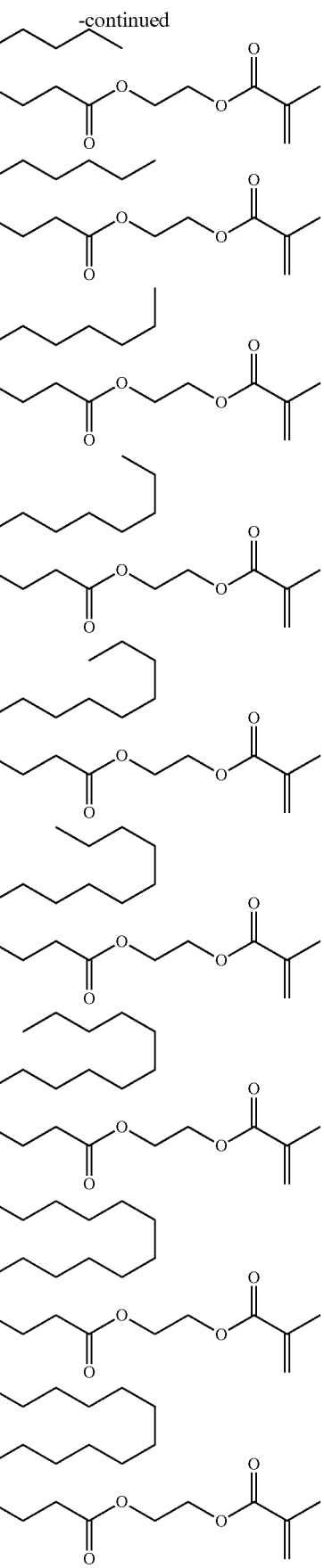

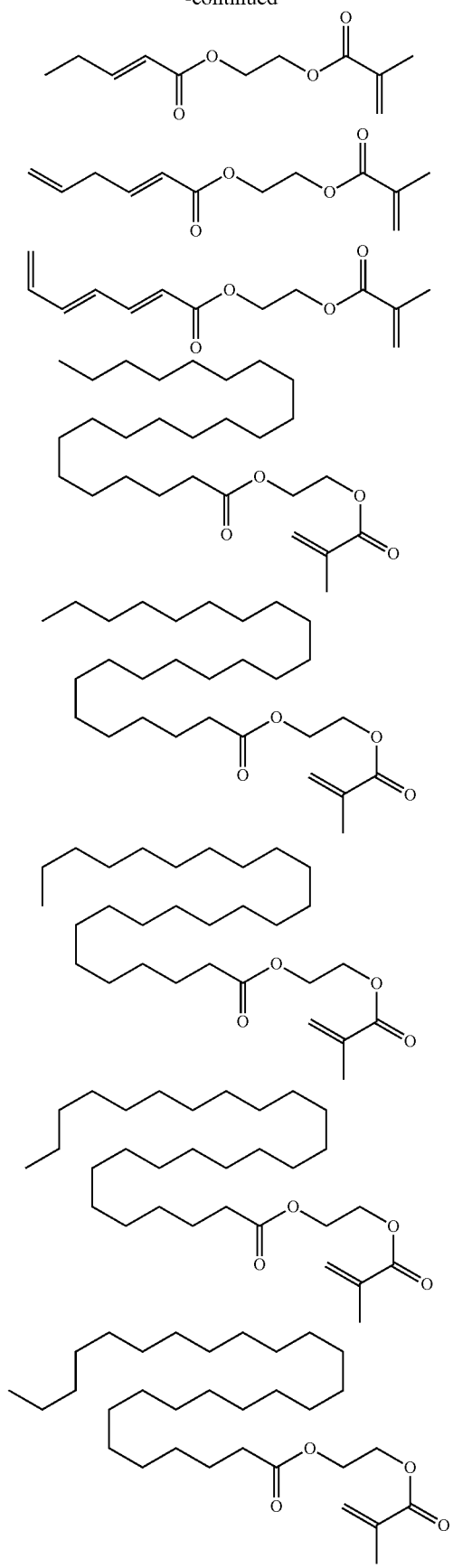
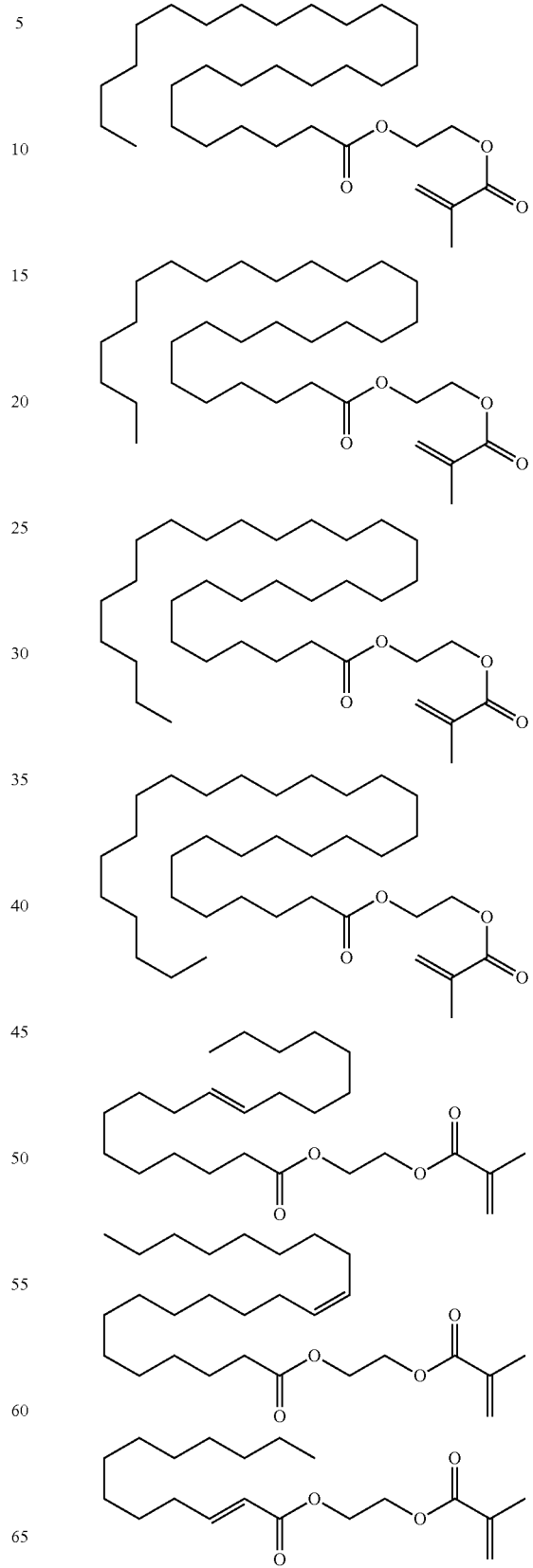

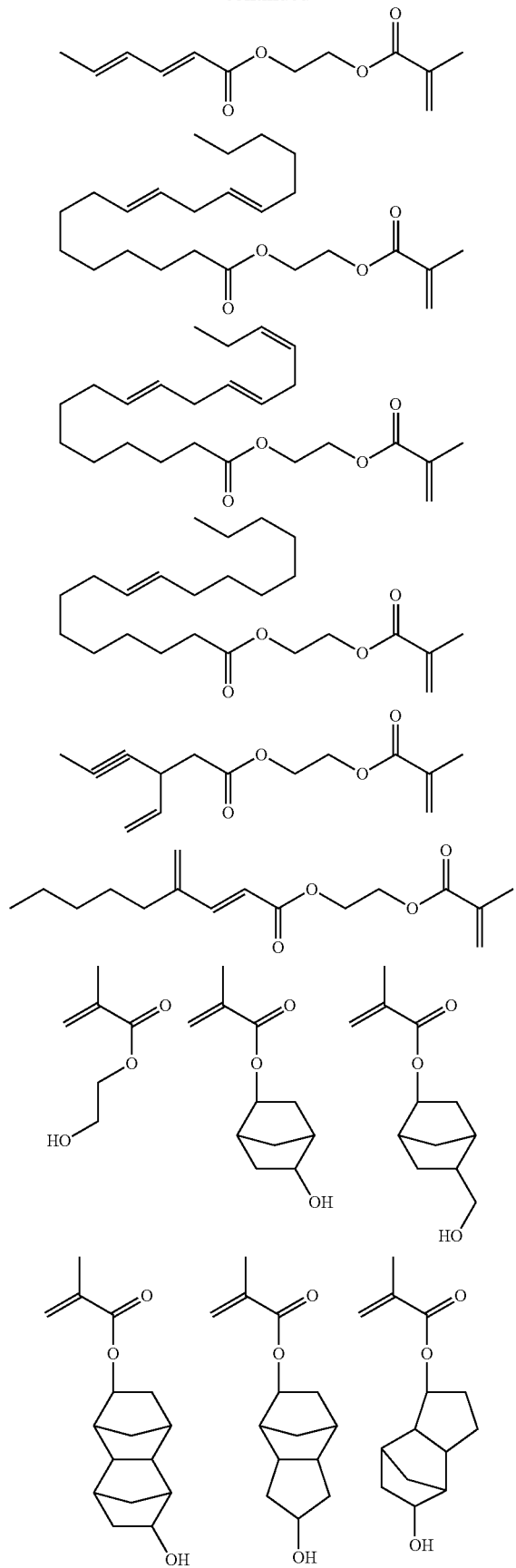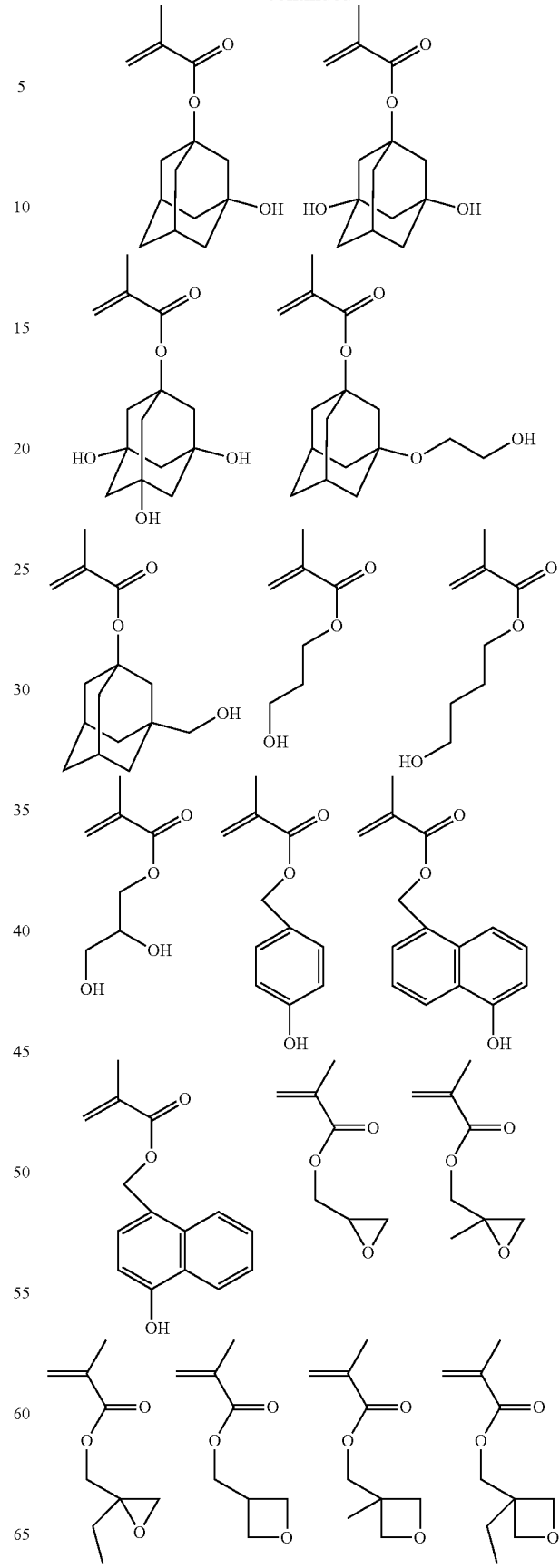

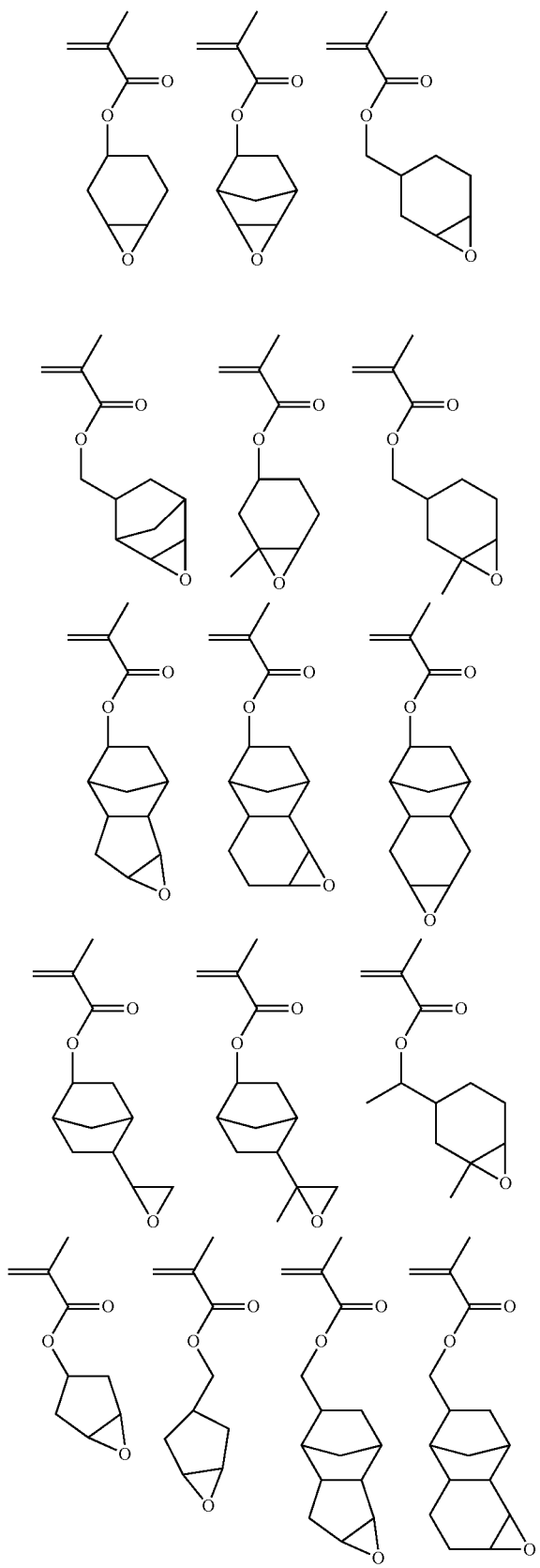
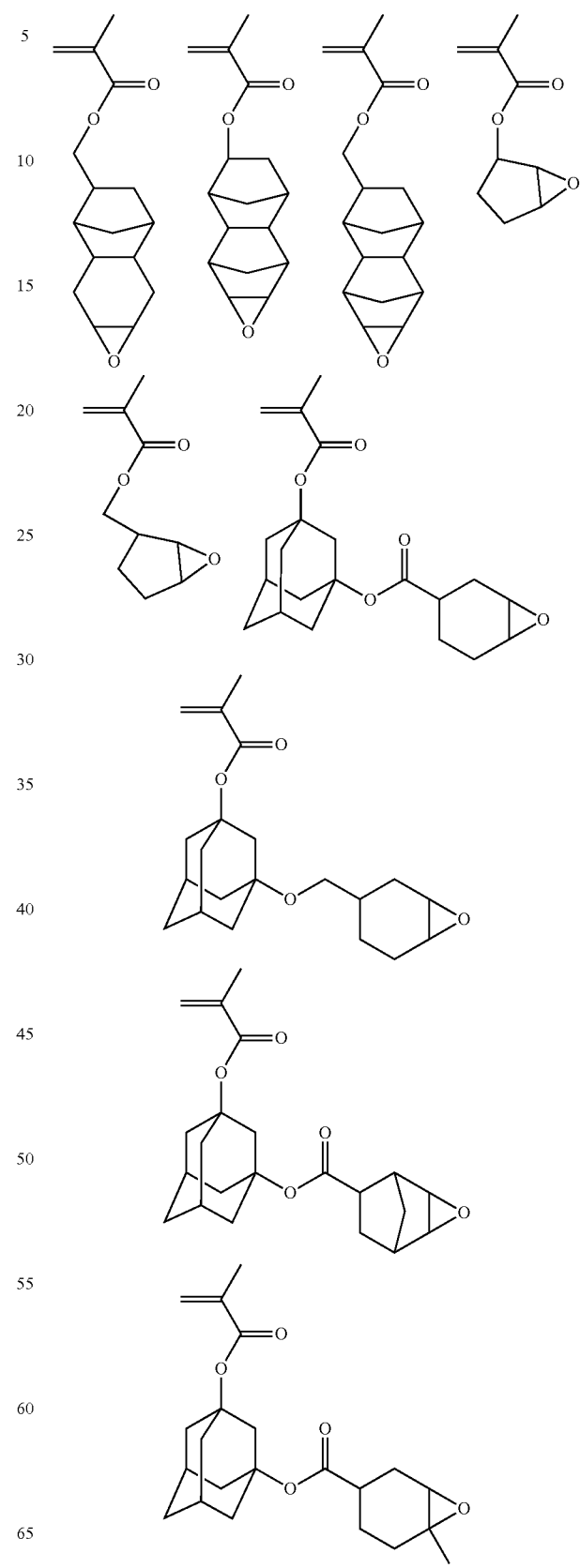

-continued
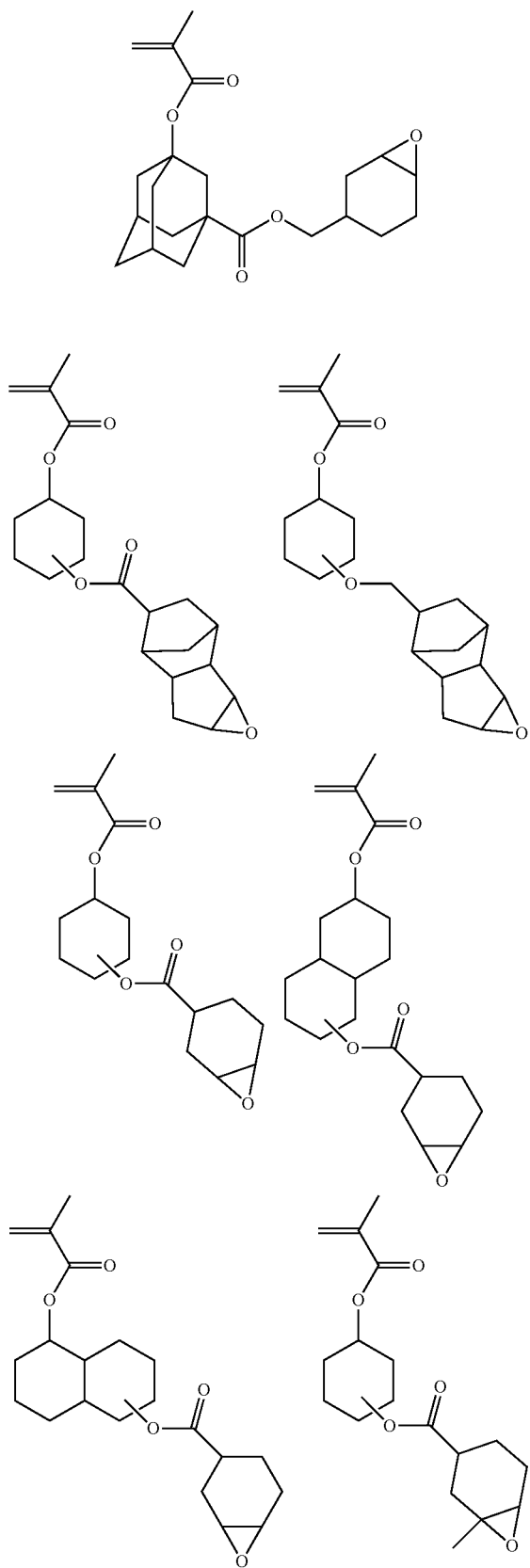
-continued
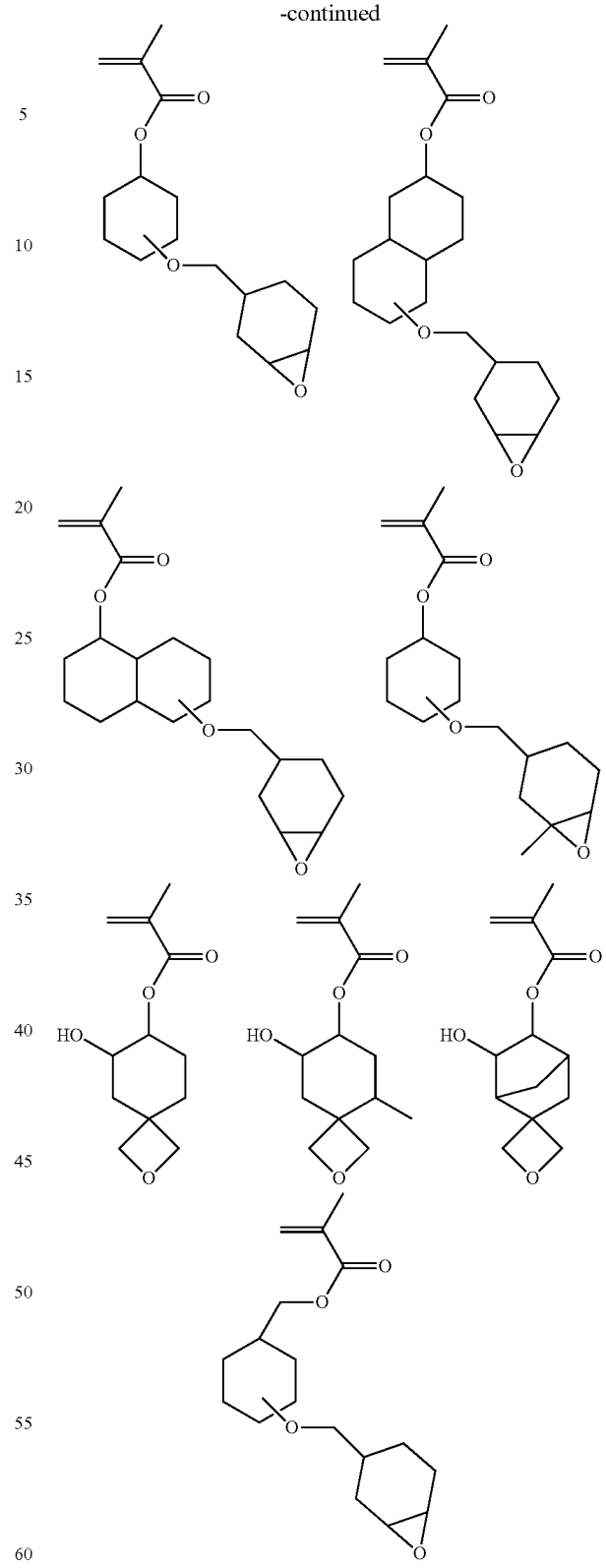
Preferably, the polymer compound in the biomedical electrode composition of the present invention not only has the repeating unit "a" and the repeating unit "b", but also includes a repeating unit "c" having a fluorine atom or a silicon atom and/or a repeating unit "d" having one or more groups selected from a hydroxy group, carboxyl group, oxirane group, and oxetane group.

The repeating unit "c" is a repeating unit giving a water repellency capability, and copolymerizing such repeating units can prevent changes in conductivity by sweating or washing. The repeating unit "d" is a repeating unit giving a crosslinking capability, and copolymerizing such repeating units can prevent peeling from a conductive substrate.

Illustrative example of the monomer for obtaining the repeating unit "c" giving a water repellency capability includes the following monomers.

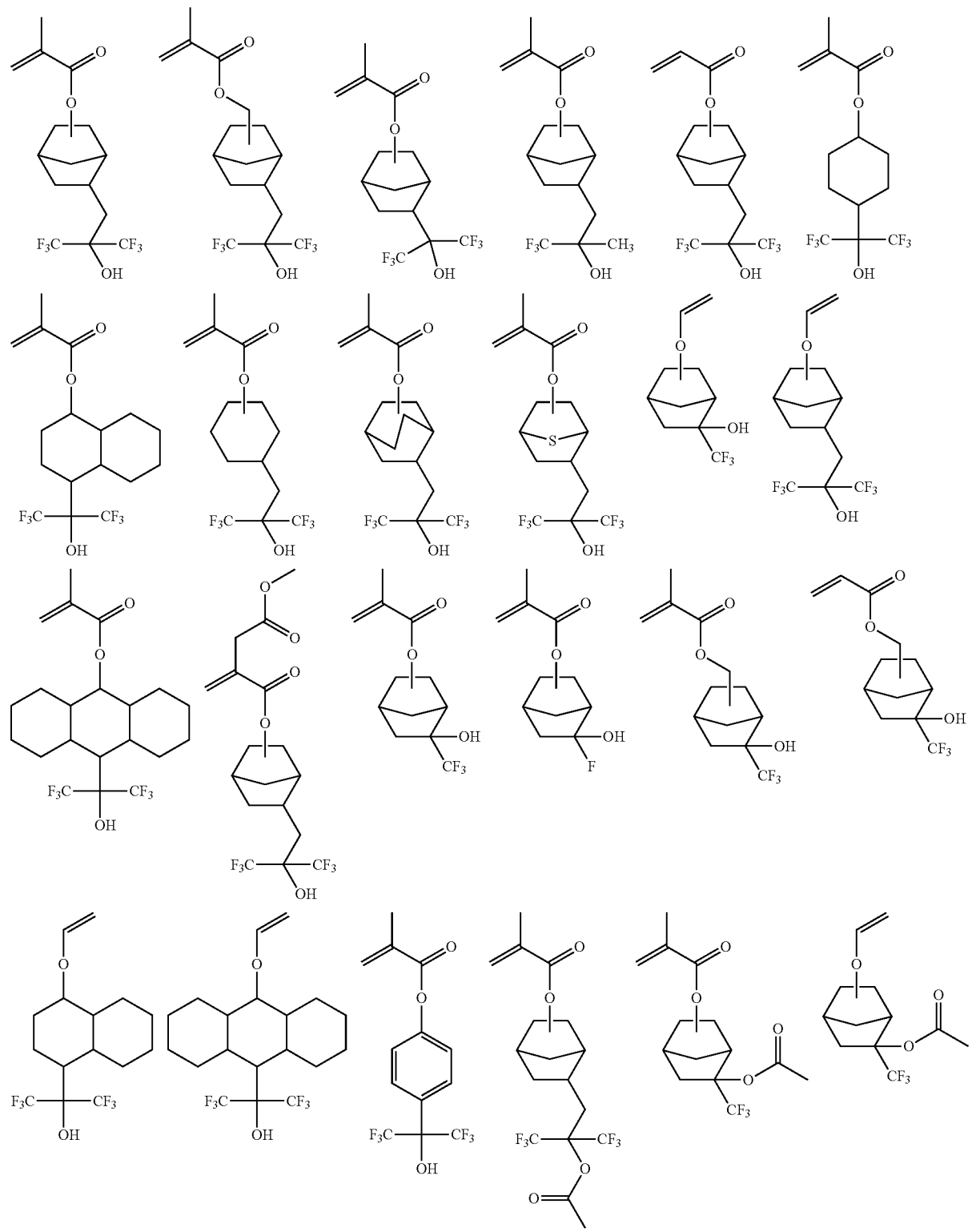

-continued
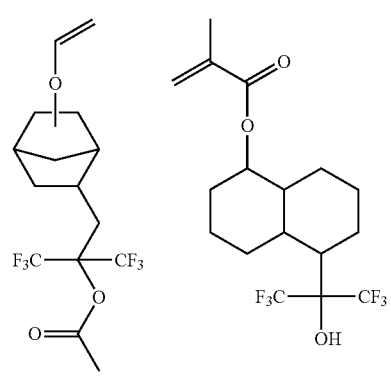 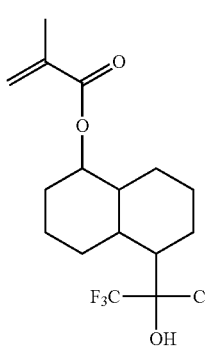 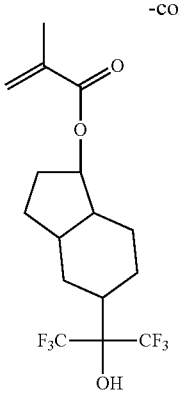 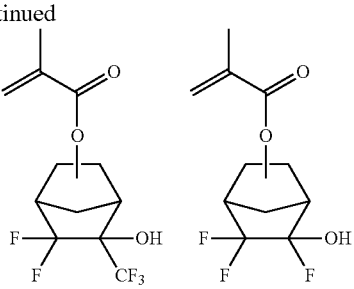 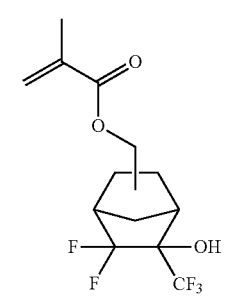
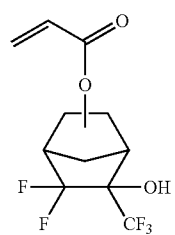 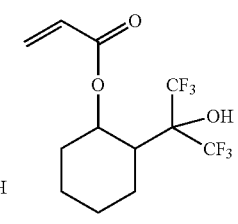 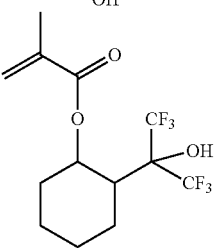 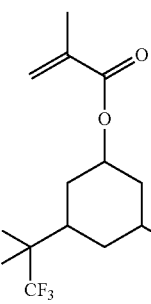 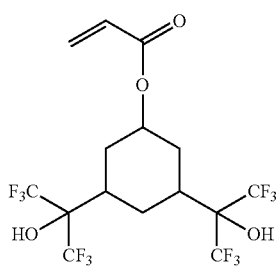
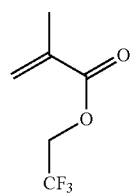 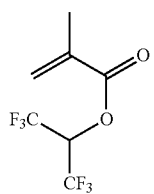 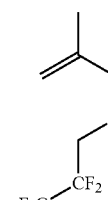 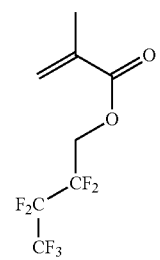 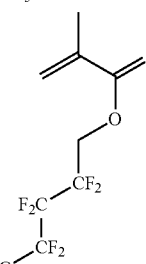 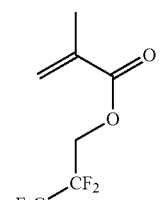
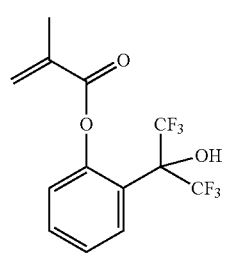 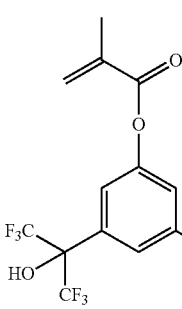 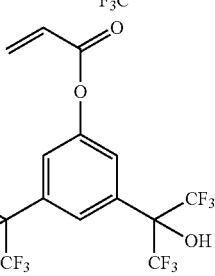 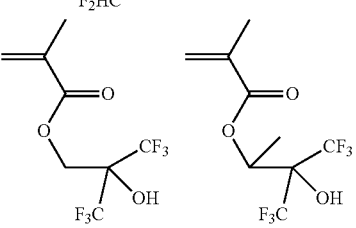
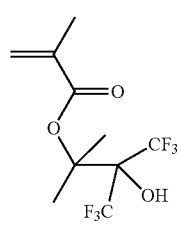 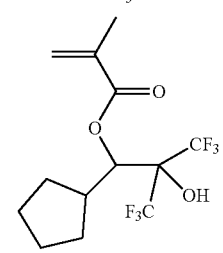 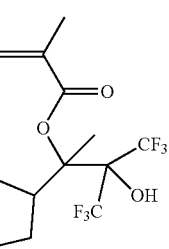 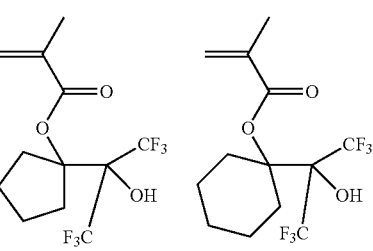
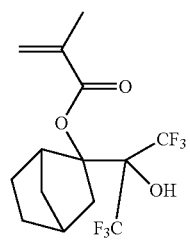 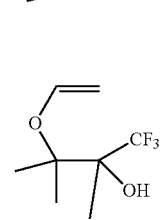 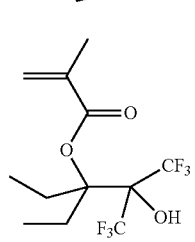 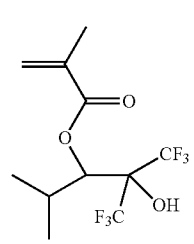 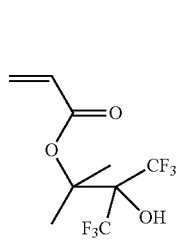 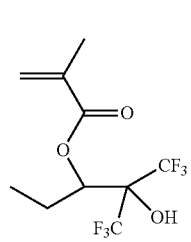

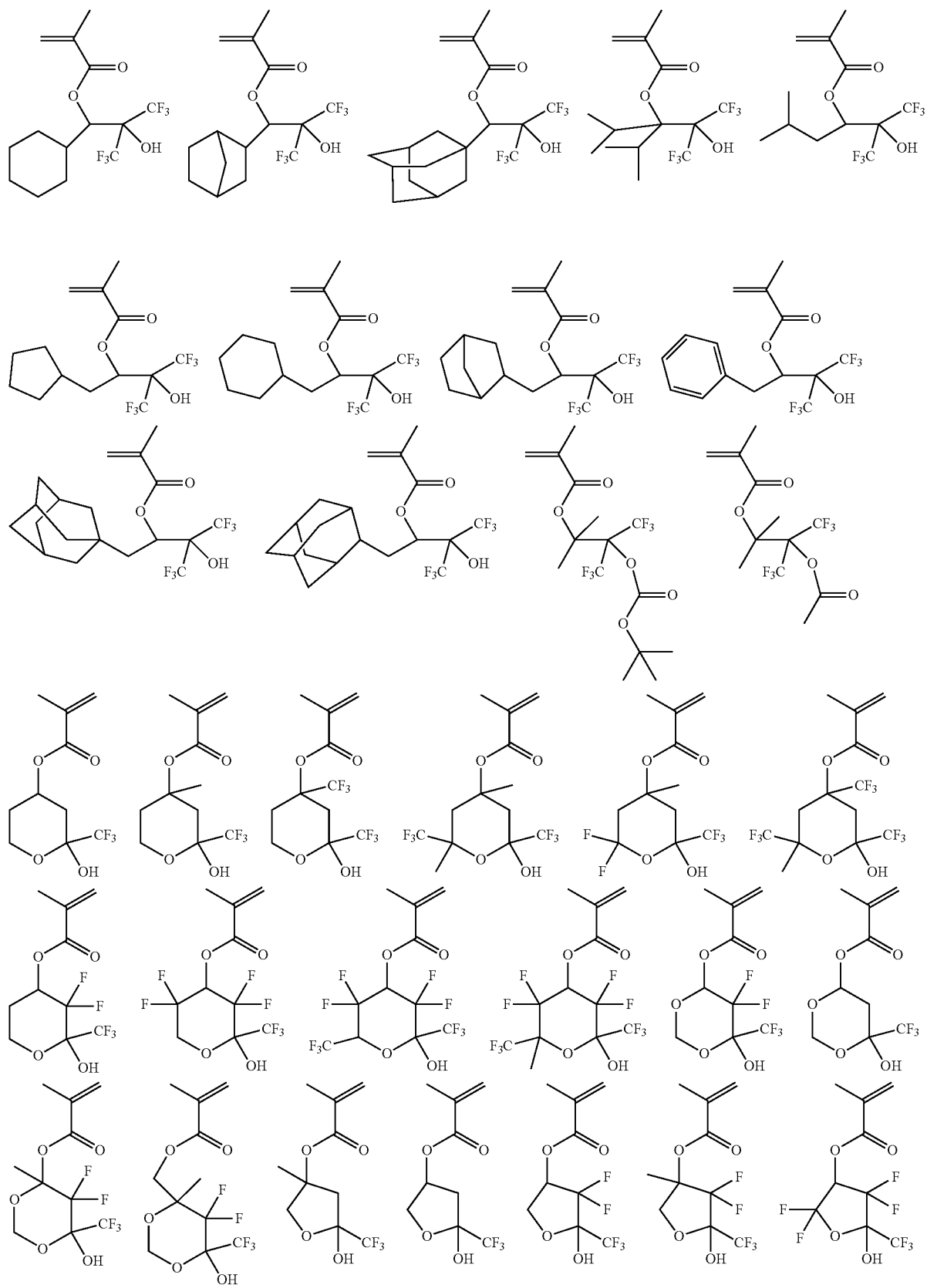

-continued
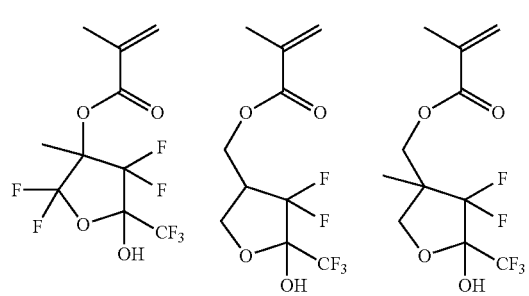
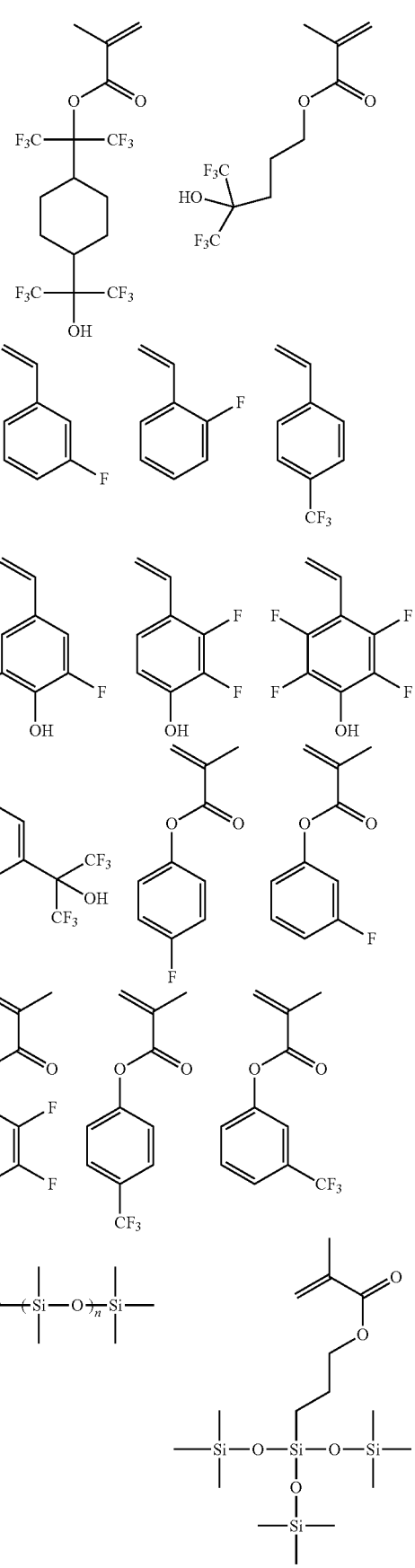

-continued
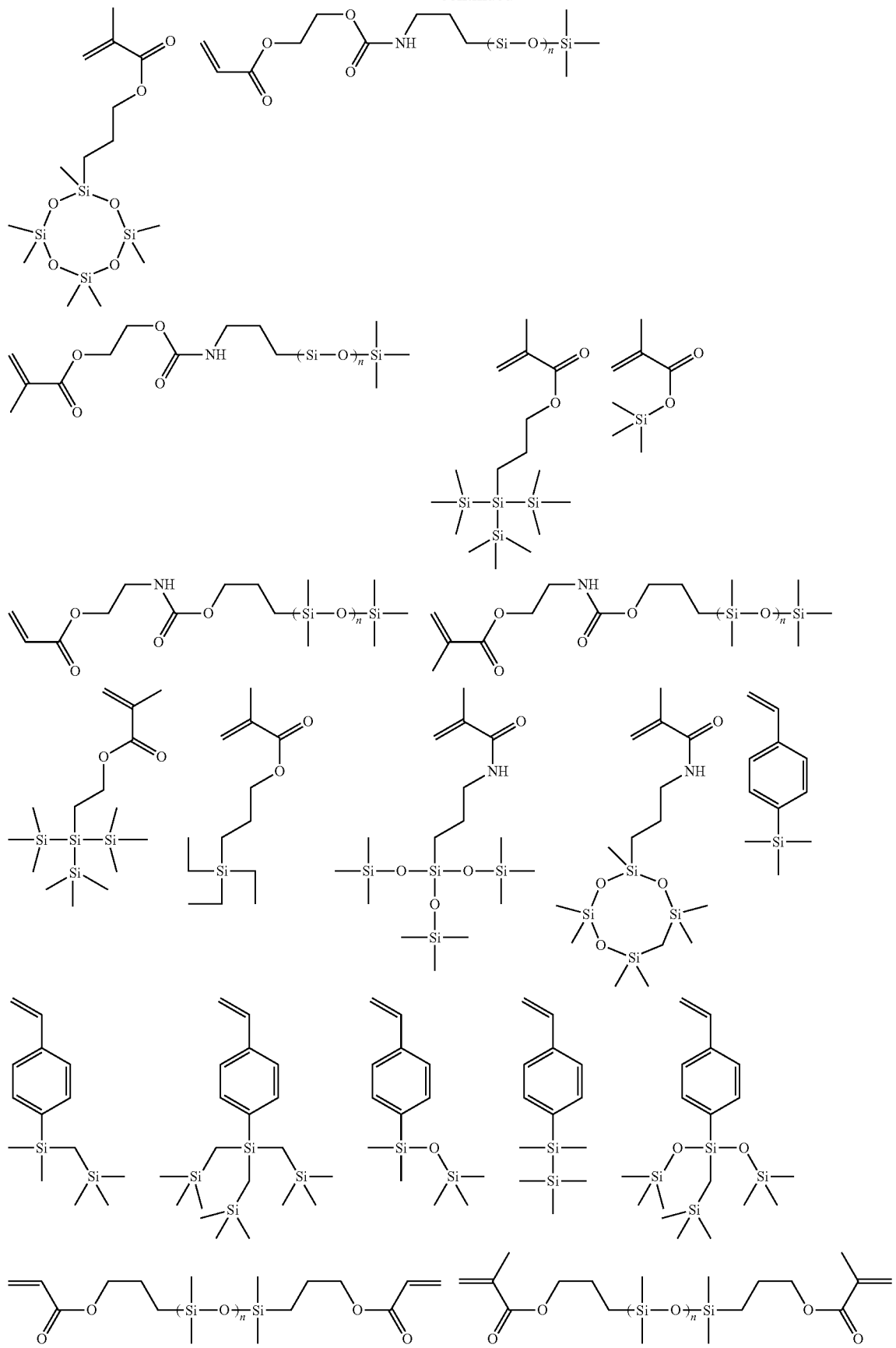

-continued
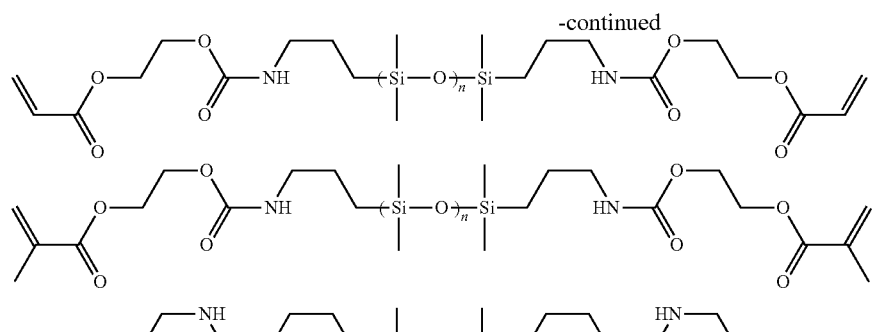
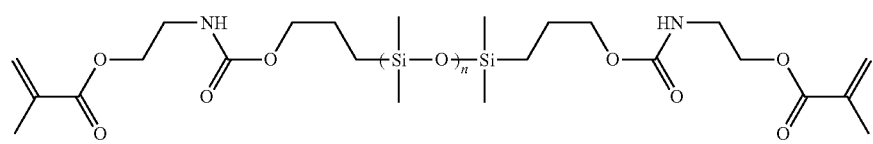
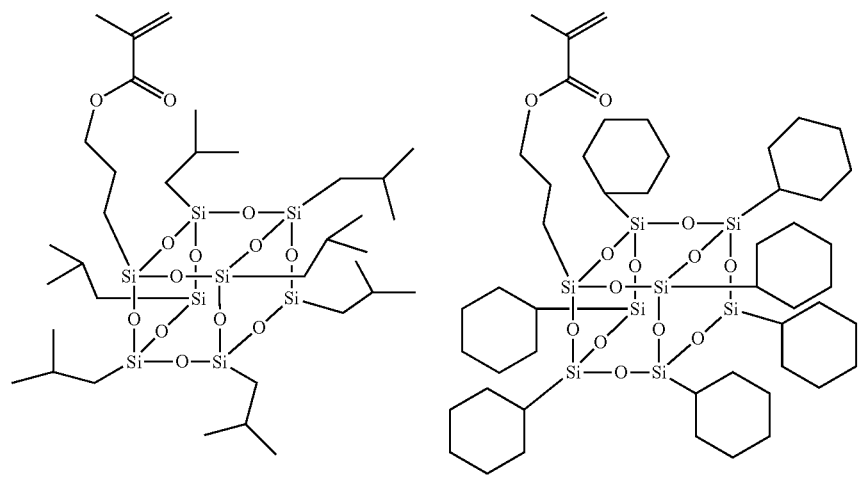
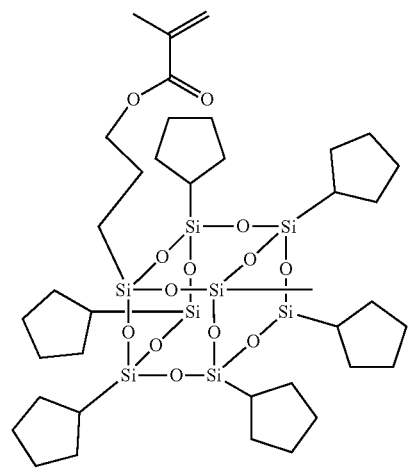
wherein, "n" is an integer of 0 to 100.

[0079] Illustrative example of the monomer for obtaining the repeating unit "d" giving a crosslinking capability includes the following monomers.
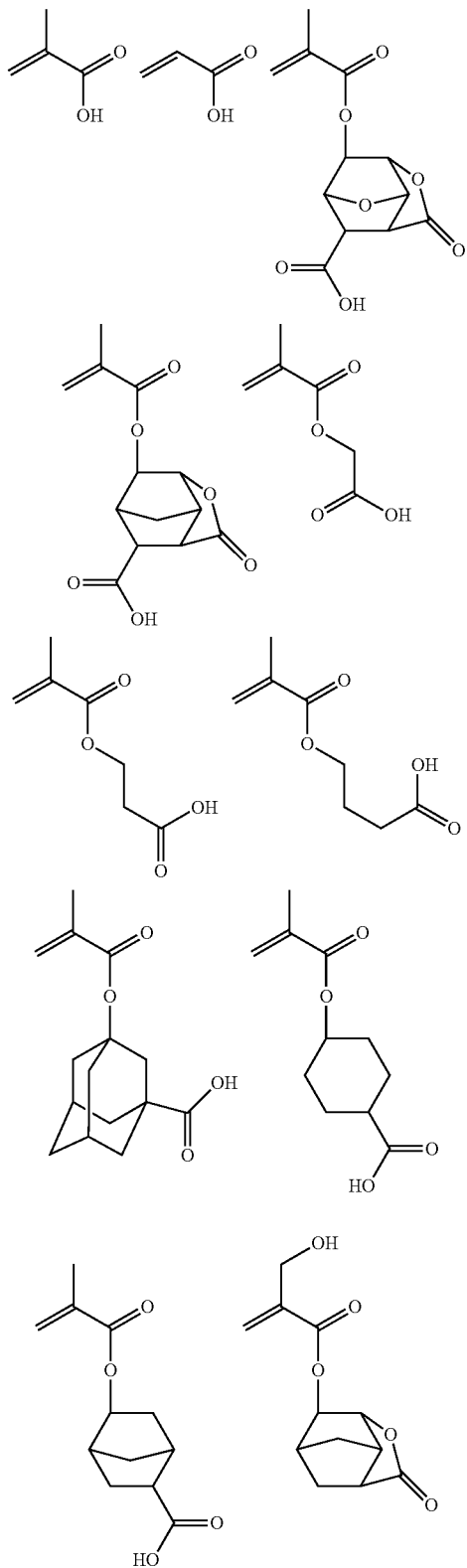
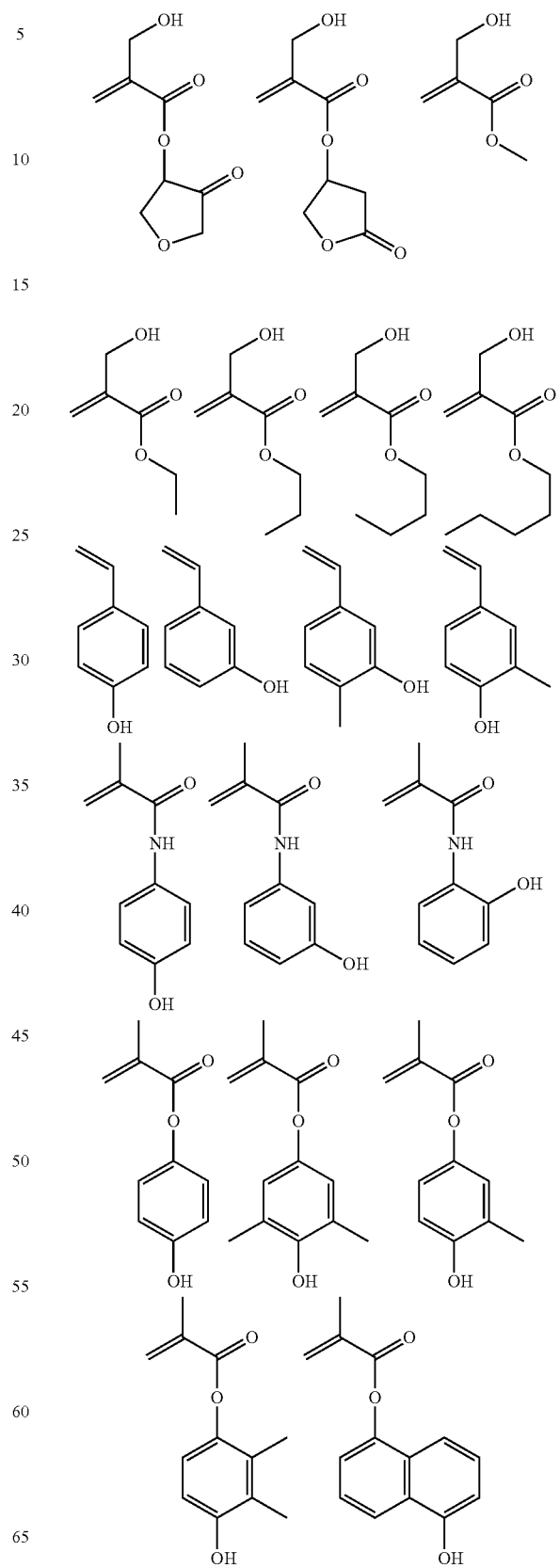

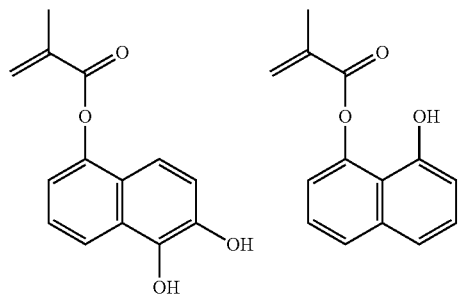
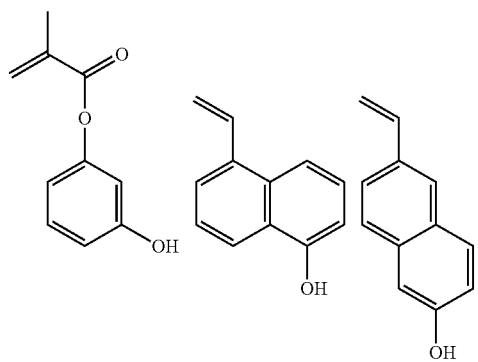
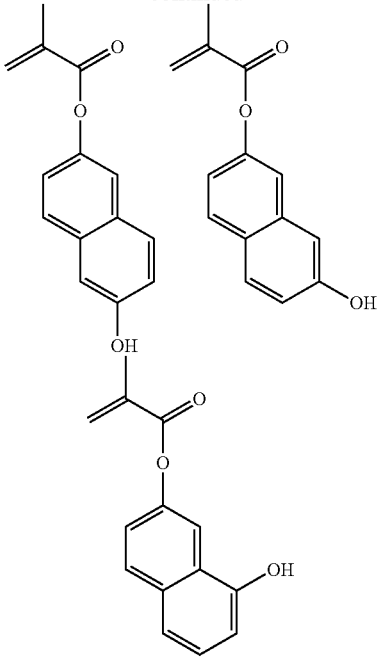
In addition, a monomer having a plurality of polymerizable double bonds can be copolymerized(repeating unit e). Accordingly, polymer compounds are crosslinked between polymers after polymerization. Illustrative example of the monomer having a plurality of polymerizable double bonds includes the following monomers.
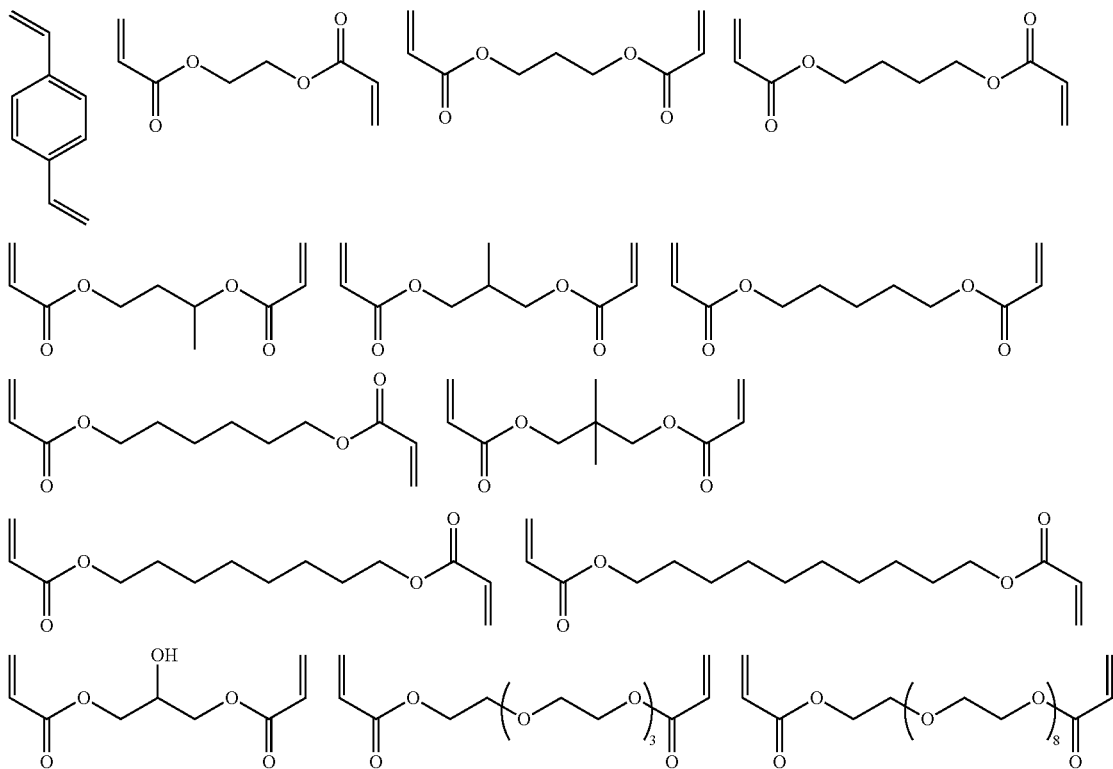

-continued
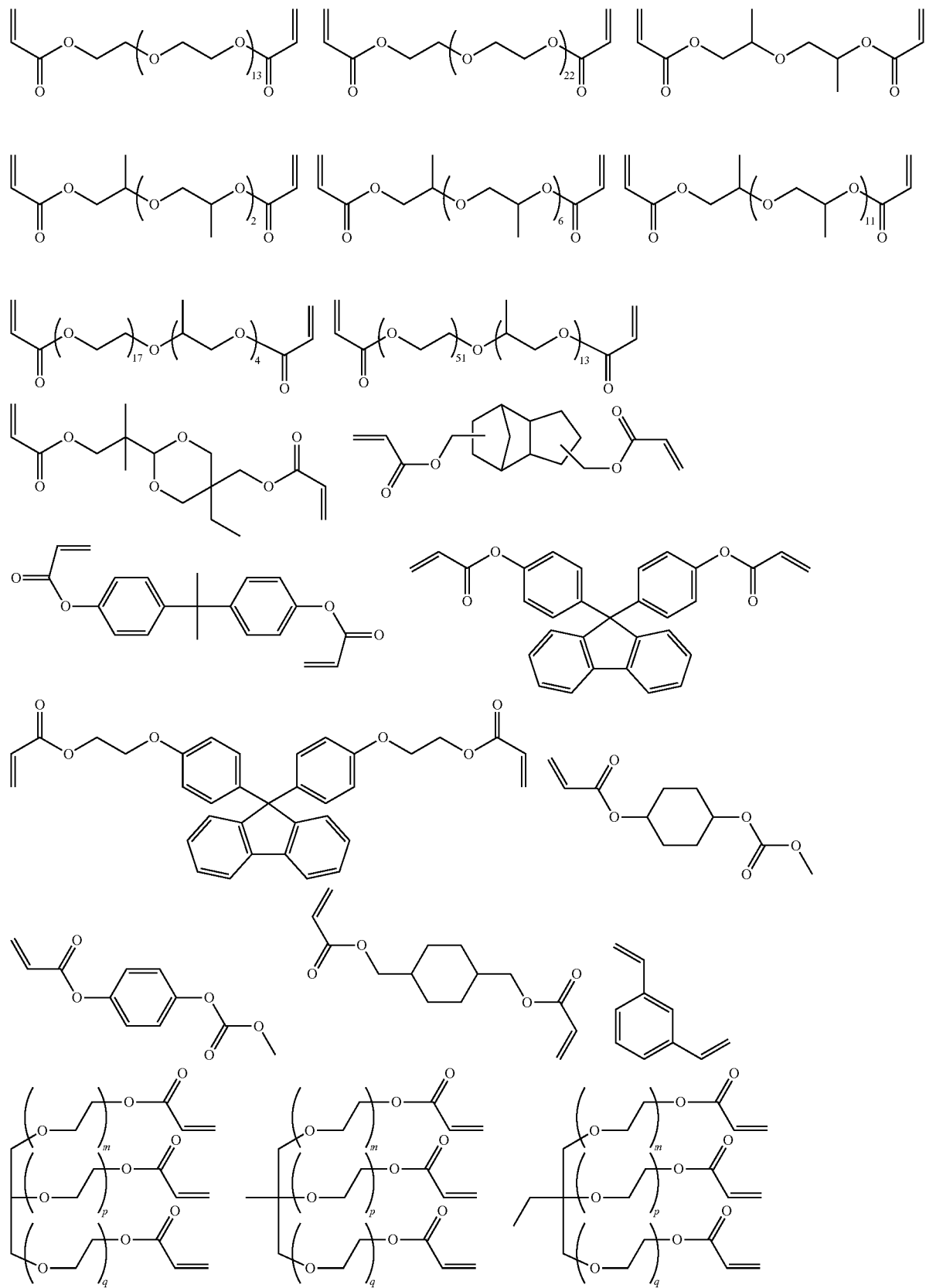

-continued
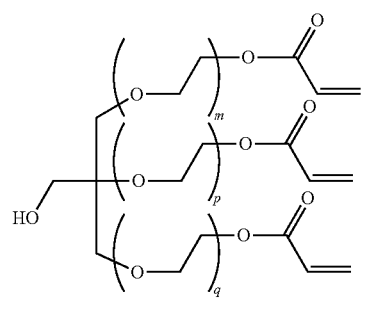 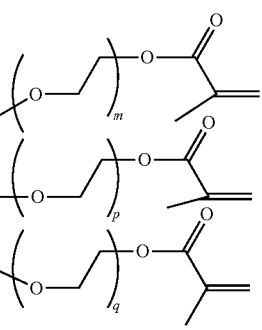
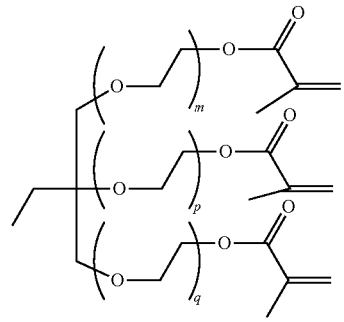 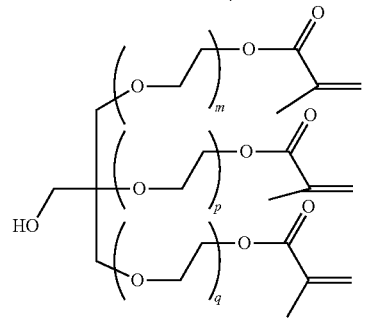 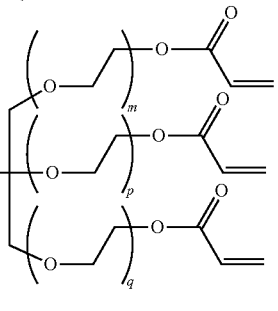
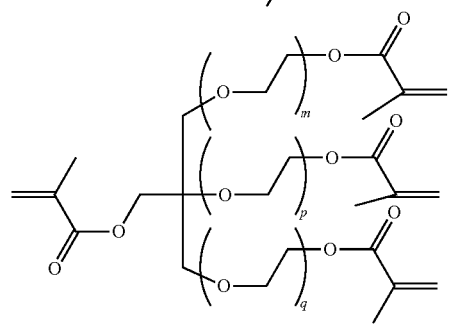 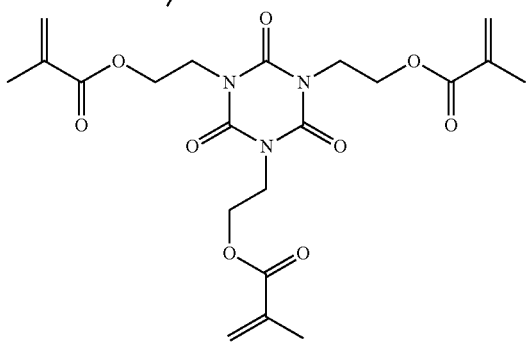
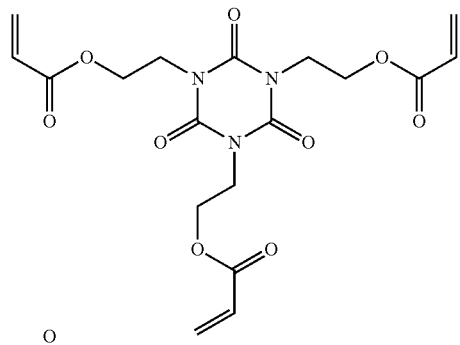
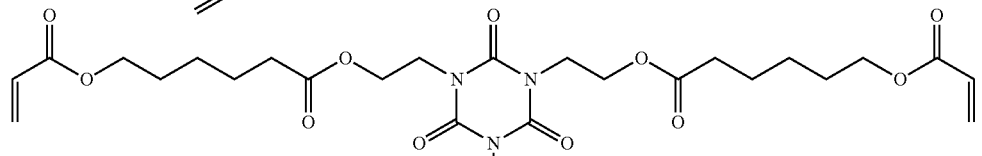
wherein, 3≤m+p+q≤30 is satisfied.

The method for synthesizing such a polymer compound may be a method for obtaining a copolymer compound by adding an initiator of radical polymerization and conducting heat polymerization of desired monomers out of monomers giving repeating units "a", "b", "c", "d", and "e" in an organic solvent.

Illustrative example of the organic solvent used in polymerization includes toluene, benzene, tetrahydrofuran, diethyl ether, and dioxane. Illustrative example of the initiator of radical polymerization includes a 2,2'-azobisisobutyronitrile (AIBN), 2,2'-azobis(2,4-dimethylvaleronitrile), dimethyl-2,2-azobis(2-methyl propionate), benzoyl peroxide, and lauroyl peroxide, and can preferably polymerize by heating at 50 to 80° C. The reaction time is 2 to 100 hours, preferably 5 to 20 hours.

When hydroxystyrene or hydroxyvinyl naphthalene is copolymerized, acetoxystyrene or acetoxyvinyl naphthalene is used, in place of hydroxystyrene or hydroxyvinyl naphthalene, to make polyhydroxystyrene or hydroxy polyvinyl naphthalene by subjecting an acetoxy group to deprotection by alkaline hydrolysis after polymerization.

The base during alkaline hydrolysis may be ammonia water or triethylamine. The reaction temperature is −20 to 100° C., preferably 0 to 60° C. The reaction time is 0.2 to 100 hours, preferably 0.5 to 20 hours.

When the polymer compound in the biomedical electrode composition of the present invention includes the repeating unit "a1", the ratios of the repeating units "a1," "b","c","d", and "e" satisfy the equations $0<a1<1.0$, $0<b<1.0$, $0\leq c<1.0$, $0\leq d\leq 0.7$, and $01.\leq e\leq 0.4$, preferably $0<a1\leq 0.9$, $0.05\leq b\leq 0.9$, $0\leq c\leq 0.8$, $0\leq d\leq 0.6$, and $0\leq e\leq 0.3$, and more preferably $0<a1\leq 0.8$, $0.1\leq b\leq 0.8$, $0\leq c\leq 0.7$, $0\leq d\leq 0.5$, and $0\leq e\leq 0.2$.

For example, "a+b+c=1" means that in a polymer compound including repeating units "a","b", and "c", the total amount of the repeating units "a","b", and "c" is 100 mole % relative to the total amount of all the repeating units, and "a+b+c<1" means that the total amount of the repeating units "a","b", and "c" is under 100 mole % relative to all the repeating units, including other repeating units other than the units "a","b", and "c."

The molecular weight of polymer compound is preferably 500 or more as weight average molecular weight, more preferably 1,000 or more and 1,000,000 or less, and much more preferably 2,000 or more and 500,000 or less. When a small amount of ionic monomer (residual monomer) is not incorporated into a polymer compound after polymerization, the immersion of the monomer in the skin is found to cause no allergy in a biocompatibility test. Preferably, the residual monomer is reduced to 10% by mass or less relative to 100 parts by mass of the polymer compound.

Organic Solvent

Also, an organic solvent can be added to the biomedical electrode composition of the present invention. Illustrative example of the organic solvent includes an aromatic hydrocarbon solvent such as toluene, xylene, cumene, 1,2,3-trimethyl benzene, 1,2,4-trimethyl benzene, 1,3,5-trimethyl benzene, styrene, α-methyl styrene, butyl benzene, sec-butyl benzene, isobutyl benzene, cymene, diethyl benzene, 2-ethyl-p-xylene, 2-propyl toluene, 3-propyl toluene, 4-propyl toluene, 1,2,3,5-tetramethyl toluene, 1,2,4,5-tetramethyl toluene, tetrahydro naphthalene, 4-phenyl-1-butene, tert-amyl benzene, amyl benzene, 2-tert-butyl toluene, 3-tert-butyl toluene, 4-tert-butyl toluene, 5-isopropyl-m-xylene, 3-methylethyl benzene, tert-butyl-3-ethyl benzene, 4-tert-butyl-o-xylene, 5-tert-butyl-m-xylene, tert-butyl-p-xylene, 1,2-diisopropyl benzene, 1,3-diisopropyl benzene, 1,4-diisopropyl benzene, dipropyl benzene, 3,9-dodecadiyne, pentamethyl benzene, hexamethyl benzene, hexyl benzene, 1,3,5-triethyl benzene; an aliphatic hydrocarbon-based solvent such as n-heptane, isoheptane, 3-methylhexane, 2,3-dimethylpentane, 3-ethyl pentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methyinonane, Cert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, a-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-en, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, isoparaffin; a ketone-based solvent such as cyclohexanone, cyclopentanone, 2-octanone, 2-nonanone, 2-heptanone, 3-heptanone, 4-heptanone, 2-hexanone, 3-hexanone, disobutyl ketone, methylcyclohexanone, and methyl-n-pentyl ketone; an alcohol-based solvent such as 3-methoxy butanol, 3-methyl-3-methoxy butanol, 1-methoxy-2-propanol, and 1-ethoxy-2-propanol; an ether-based solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methylcyclopentyl ether, methylcyclohexyl ether, di-n-butyl ether, di-sec-butyl ether, diisopentyl ether, di-sec-pentyl ether, di-tert-amyl ether, di-n-hexyl ether, and anisole; an ester-based solvent such as propylene glycol monomethyl ether acetate, propylene glycol monoethyl ether acetate, ethyl lactate, ethyl pyruvate, butyl acetate, methyl 3-methoxy propionate, ethyl 3-ethoxy propionate, tert-butyl acetate, tert-butyl propionate, propylene glycol mono-tert-butyl etheracetate; and a lactone-based solvent such as y-butyrolactone.

The amount of the organic solvent to be added is preferably 10 to 50,000 parts by mass relative to 100 parts by mass of the polymer compound.

Carbon Material

A carbon material can be added to the biomedical electrode composition of the present invention as a conductive improver to further enhance the conductivity. Illustrative example of the carbon material includes carbon black and carbon nanotube. The carbon nanotube may be either single-layer or multi-layer, and the surface may be modified with an organic group. The amount of the carbon material to be added is preferably in the range of 1 to 50 parts by mass relative to 100 parts by mass of the polymer compound.

Conductive Improver Other Than Carbon Material

A conductive improver other than a carbon material can be added to the biomedical electrode composition of the present invention. Illustrative example thereof includes a particle in which a resin is coated with a precious metal such as gold, silver, and platinum, and copper or nickel, a nanoparticle such as gold, silver, and platinum, and a particle of metal oxide such as indium tin oxide (ITO), indium zinc oxide (IZO), tin oxide, and zinc oxide. In particular, an ITO particle, or a particle coated with a metal selected from silver, gold, platinum, copper, and nickel is preferable.

Crosslinking Agent

After a biomedical electrode is peeled from the skin, a crosslinking agent may be added so that a living body contact layer is not attached to the skin. Illustrative example of the crosslinking agent used in the present invention includes a melamine compound substituted by at least one group selected from a methylol group, an alkoxymethyl group, and an acyloxymethyl group, a guanamine compound, a glycoluril compound, or a urea compound, an epoxy compound, an isocyanate compound, an azide compound, and a compound containing a double bond such as an alkenyl ether group. These may be used as an additive, but may be introduced into a side chain of a polymer compound as a pendant group. Also, a compound containing a hydroxy group can be used as a crosslinking agent.

Illustrative example of the epoxy-based crosslinking agent includes tris(2,3-epoxypropyl)isocyanurate, trimethylol methane triglycidyl ether, trimethylol propane triglycidyl ether, triethylol ethane triglycidyl ether, and silicone having an epoxy group. Illustrative example of the melamine compound includes a compound in which 1 to 6 methylol groups of hexamethylol melamine, hexamethoxymethyl melamine, and hexamethylolmelamine are methoxymethylated or a mixture thereof, and a compound in which 1 to 6 methylol groups of hexamethoxyethyl melamine, hexaacyloxymethyl melamine, and hexamethylol melamine are acyloxymethylated or a mixture thereof. Illustrative example of the guanamine compound includes a compound in which 1 to 4 methylol groups of tetramethylol guanamine, tetramethoxymethyl guanamine, and tetramethylol guanamine are methoxymethylated or a mixture thereof, and a compound in which 1 to 4 methylol groups of tetramethoxyethyl guanamine, tetraacyloxy guanamine, and tetramethylol guanamine are acyloxymethylated or a mixture thereof. Illustrative example of the glycoluril compound includes a compound in which 1 to 4 methylol groups of tetramethylolglycol uril, tetramethoxyglycol uril, tetramethoxymethylglycol uril, and tetramethylolglycol uril are methoxymethylated or a mixture thereof, and a compound in which 1 to 4 methylol groups of tetramethylolglycol uril are acyloxymethylated or a mixture thereof. Illustrative example of the urea compound includes a compound in which 1 to 4 methylol groups of tetramethylol urea, tetramethoxymethyl urea, and tetramethylol urea are methoxymethylated or a mixture thereof, and tetramethoxyethyl urea.

Illustrative example of the isocyanate compound includes tolylene diisocyanate, diphenylmethane diisocyanate, and hexamethylene diisocyanate, and cyclohexane diisocyanate, and illustrative example of the azide compound includes 1,1'-biphenyl-4,4'-bisazide, 4,4'-methylidenebisazide, and 4,4'-oxybisazide.

Illustrative example of the compound containing an alkenyl ether group includes ethylene glycoldivinyl ether, triethylene glycoldivinyl ether, 1,2-propanediol divinyl ether, 1,4-butanediol divinyl ether, tetramethyleneglycol divinyl ether, neopentylglycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitoltetra vinyl ether, sorbitolpenta vinyl ether, and trimethylolpropanetrivinyl ether.

As described above, the biomedical electrode composition of the present invention can form a living body contact layer for a biomedical electrode that is capable of efficiently converting changes in ion concentration from the skin into electric signals and efficiently transmitting such electric signals to a device (or that is excellent in conductivity), generating no allergy despite its long-time attachment to the skin due to no immersion of polymer ion components to the skin (or that is excellent in biocompatibility), reducing no conductivity by sweating or washing because of no ion component extraction even though the biomedical electrode is in contact with water, is light-weight, can be manufactured at low cost. Accordingly, the biomedical electrode composition also serves as an adhesive agent. Also, the addition of a carbon material or a precious metal-coated particle can further improve the conductivity to manufacture a highly adhesive, elastic biomedical electrode. The polymer compound composition and the thickness of a living body contact layer can be adjusted as required to control the elasticity and adhesion.

Biomedical Electrode

The present invention provides a biomedical electrode including a conductive substrate and a living body contact layer formed on the conductive substrate, wherein the living body contact layer is a cured product of the biomedical electrode composition of the present invention.

The biomedical electrode of the present invention will be described in detail with reference to the drawings, but the present invention is not restricted thereto.

FIG. 1 is a schematic cross-sectional view showing one example of a biomedical electrode of the present invention. In FIG. 1, a biomedical electrode 1 includes a conductive substrate 2 and a living body contact layer 3 formed on the conductive substrate 2. The living body contact layer 3 is a layer in which a carbon material 4 is dispersed in a polymer compound (resin) 5.

Figure 2:
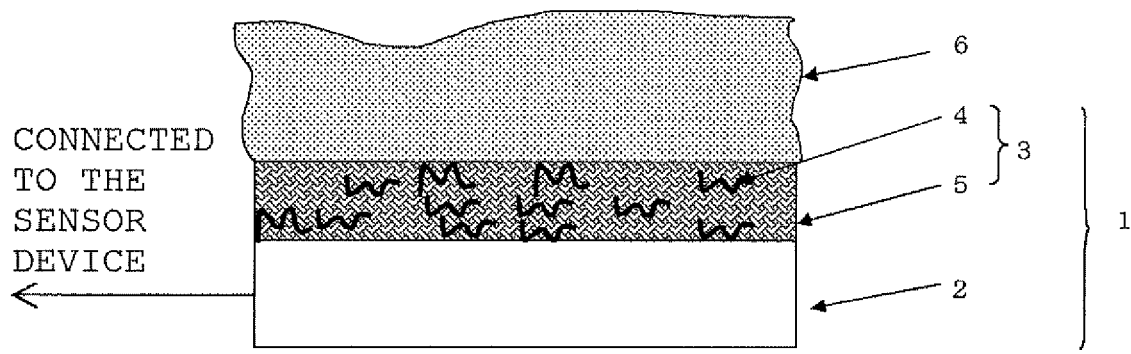
FIG. 2 is a schematic cross-sectional view showing one example of a biomedical electrode of the present invention that is attached to a living body.

When such a biomedical electrode 1 shown in FIG. 1 is used, as shown in FIG. 2, a living body contact layer 3 (or, a layer in which a carbon material 4 is dispersed in a polymer compound 5) is brought in contact with a living body 6 to take electric signals out of the living body 6 by the polymer compound 5 and the carbon material 4, and the electric signals are transmitted via the conductive substrate 2 to a sensor device (not shown). Accordingly, the biomedical electrode of the present invention can satisfy both conductivity and biocompatibility by the polymer compound. As required, a conductive improver such as carbon material can be added to further improve the conductivity, and its adhesion can keep the contact area with the skin constant and stably obtain electric signals from the skin with high sensitivity.

Each component of the biomedical electrode of the present invention will be described in more detail.

Conductive Substrate

The biomedical electrode of the present invention includes a conductive substrate. The conductive substrate is normally electrically connected to a sensor device unit to transmit electric signals taken out of a living body via a living body contact layer to the sensor device unit.

The conductive substrate is not particularly restricted so long as it is conductive, preferably e.g., one or more substances selected from gold, silver, silver chloride, platinum, aluminum, magnesium, tin, tungsten, iron, copper, nickel, stainless steel, chromium, titanium, and carbon.

The conductive substrate is not particularly restricted, but may be a hard conductive substrate, a flexible conductive film, a fabric coated with a conductive paste on the surface, or a fabric weaved with a conductive polymer. The conductive substrate may be selected according to use of a biomedical electrode, and may be flat, irregular or mesh weaved with metal wire.

Living Body Contact Layer

The biomedical electrode of the present invention includes a living body contact layer formed on the conductive substrate. The living body contact layer is in contact with a living body when the biomedical electrode is used, having conductivity and adhesion. The living body contact layer is a cured product of the biomedical electrode composition of the present invention, or an adhesive resin layer including the adhesive polymer compound, and as required, an additive such as carbon material.

The adhesive strength of a living body contact layer is preferably 0.1N/25 mm or more and 20N/25 mm or less. The method for measuring an adhesive strength is commonly stipulated according to JIS Z 0237 standards. The substrate may be a metal substrate such as SUS (stainless steel) or a PET (polyethylene terephthalate) substrate, but human skin can be used for measurement. The human skin has a lower surface energy than metals and plastics, and it is as low as Teflon (registered trademark), and the skin is less likely to adhere.

The thickness of the living body contact layer of the biomedical electrode is preferably 0.1 μm or more and 5 mm or less, more preferably 0.2 μm or more and 3 mm or less. A thinner living body contact layer is characterized by lower adhesive strength, but by improved flexibility, and light-weight and then favorable compatibility with the skin. The thickness of a living body contact layer can be selected in view of adhesion and touch feeling to the skin.

In the biomedical electrode of the present invention, as in a conventional biomedical electrode (e.g., a biomedical electrode disclosed in JP-A-2004-033468), an additional adhesive film may be provided on a living body contact layer to prevent the biomedical electrode from peeling from the living body when in use. In this case, an adhesive film may be made of an acrylic, a urethane, or a silicone adhesive film material. In particular, a silicone adhesive film material has high oxygen permeability, allowing for dermal respiration with the same attached to the skin. Higher water repellency can also control reduction in adhesion by sweating, and the stimulation to the skin is advantageously low. In the biomedical electrode of the present invention, as described above, the addition of a tackiness imparting agent to a biomedical electrode composition or use of a polymer compound favorably adhesive to a living body can prevent peeling from the living body, thereby saving the above additional adhesive film.

When the biomedical electrode of the present invention is used as a wearable device, wires for connecting a biomedical electrode and a sensor device and other members are not particularly restricted, but those disclosed in e.g., JP-A-2004-033468 can be employed.

As described above, the biomedical electrode of the present invention has a living body contact layer formed of a cured product of the biomedical electrode composition of the present invention and therefore, is capable of efficiently transmitting electric signals from the skin to a device (or, that is excellent in conductivity), generating no allergy despite its long-time attachment to the skin (or, that is excellent in biocompatibility), is light-weight, can be manufactured at low cost, and can control significant reduction in conductivity even though the biomedical electrode is soaked in water or dried. Addition of a carbon material can further improve the conductivity, and a combination of an adhesive and elastic polymer compound can manufacture a particularly highly adhesive, elastic biomedical electrode. Furthermore, the use of additives can improve the elasticity and adhesion to the skin. The polymer compound composition and the thickness of a living body contact layer can be adjusted as required to control the elasticity and adhesion. Accordingly, such a biomedical electrode of the present invention is particularly desirable as a biomedical electrode used in medical wearable devices.

A method for manufacturing a biomedical electrode. The present invention provides a method for manufacturing a biomedical electrode including a conductive substrate and a living body contact layer formed on the conductive substrate, including: applying the biomedical electrode composition of the present invention to the conductive substrate to be cured to form the living body contact layer.

A conductive substrate, a biomedical electrode composition and others used in the method for manufacturing a biomedical electrode of the present invention may be the same as before.

The method for applying a biomedical electrode composition to a conductive substrate is not particularly restricted, but e.g., such methods as dipping coat, spraying coat, spin coat, roll coat, flow coat, doctor coat, screen printing, flexographic printing, gravure printing, and ink-jet printing are desirable.

The method for curing a polymer compound is not particularly restricted and may be selected according to the type of polymer compound used in the biomedical electrode composition, preferably e.g., by heating and/or light exposure. Also, a catalyst for generating an acid or a base can be added to the biomedical electrode composition, thereby generating a crosslinking reaction to cure a polymer compound.

The heating temperature is not particularly restricted and may be selected according to the type of polymer compound used in the biomedical electrode composition, preferably e.g., 50 to 250° C.

The polymer compound may be cured by heating and light exposure at the same time, or first light exposure and then heating, or vice versa. The polymer compound may be air-dried to evaporate a solvent prior to heating after making film.

As described above, the method for manufacturing a biomedical electrode of the present invention can readily manufacture the biomedical electrode of the present invention that is excellent in conductivity and biocompatibility, is light-weight, can be manufactured at low cost, and can control significant reduction in conductivity even though the biomedical electrode is soaked in water or dried.

EXAMPLE

The present invention will be described in detail with reference to the Examples and Comparative Examples, but the present invention is not restricted thereto.

Ionic polymer compounds 1 to 10, a Comparative polymer compound 1, and Comparative ionic polymer compounds 1 and 2 blended into a biomedical electrode composition solution as a polymer compound are shown as follows.

A PGMEA (propylene glycol-1-monomethyl ether-2-acetate) solution including 30% by mass of each monomer was mixed in a reaction vessel, and the reaction vessel was cooled down to −70° C. in nitrogen atmosphere, subjected to reduced pressure for deaeration and nitrogen blow three times. After the product was heated at elevated temperatures up to room temperature, AIBN (azobisisobutyronitrile) was added by 0.01 mole relative to 1 mole of the total monomer as a polymerization initiator, heated at elevated temperatures up to 60° C. Then the product was reacted for 15 hours to obtain solutions containing each of the polymer compounds (ionic polymer solutions 1 to 10, Comparative polymer solution 1, Comparative ionic polymer solutions 1 and 2). The composition of the polymers obtained were confirmed by $^1$H-NMR after drying the solvent, and the molecular weight (Mw) and the degree of dispersion (Mw/Mn) of the polymers obtained were confirmed by GPC, using THF as a solvent.

Ionic Polymer 1
Mw=20, 900
Mw/Mn=2.21

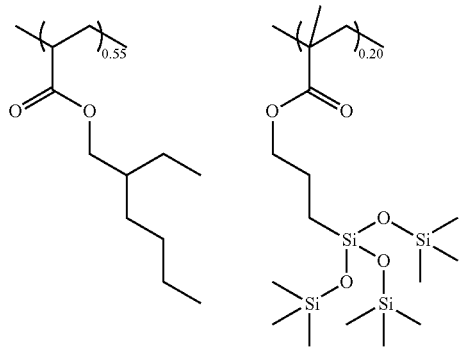

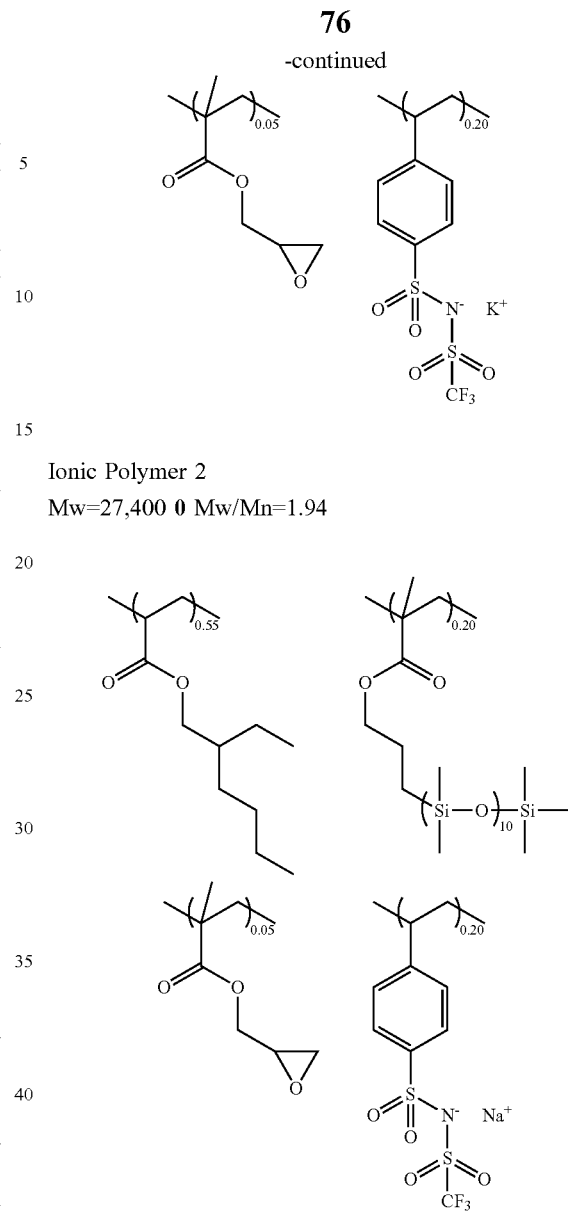

Ionic Polymer 2
Mw=27,400 0 Mw/Mn=1.94 wherein, the repeating number represents the average.

Ionic Polymer 3
Mw=30,600
Mw/Mn=1.88

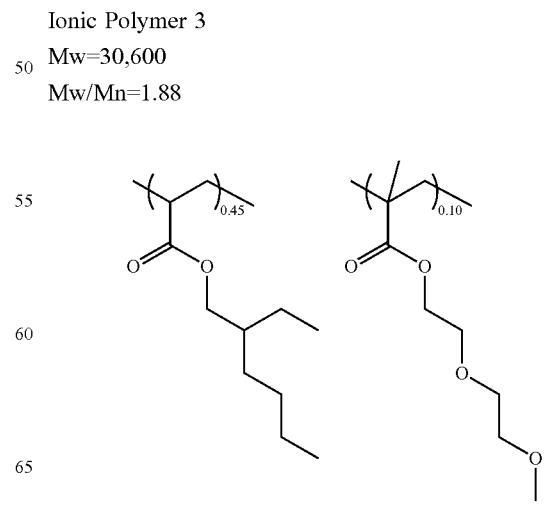

-continued
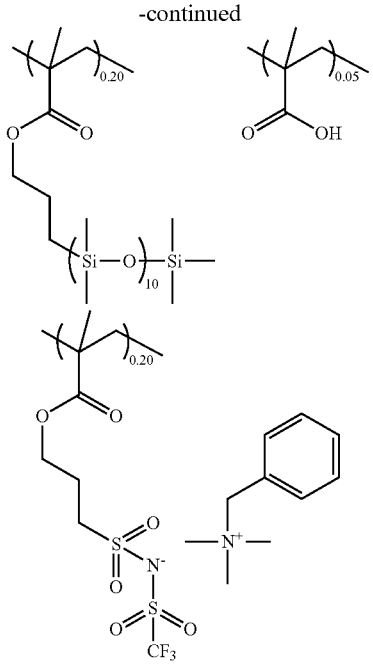
wherein, the repeating number represents the average.
Ionic Polymer 4
Mw=26,600
Mw/Mn=1.86
Ionic Polymer 5
Mw=80,900
Mw/Mn=4.33
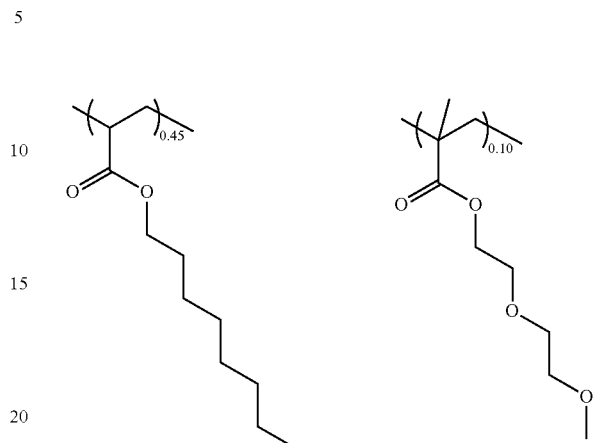
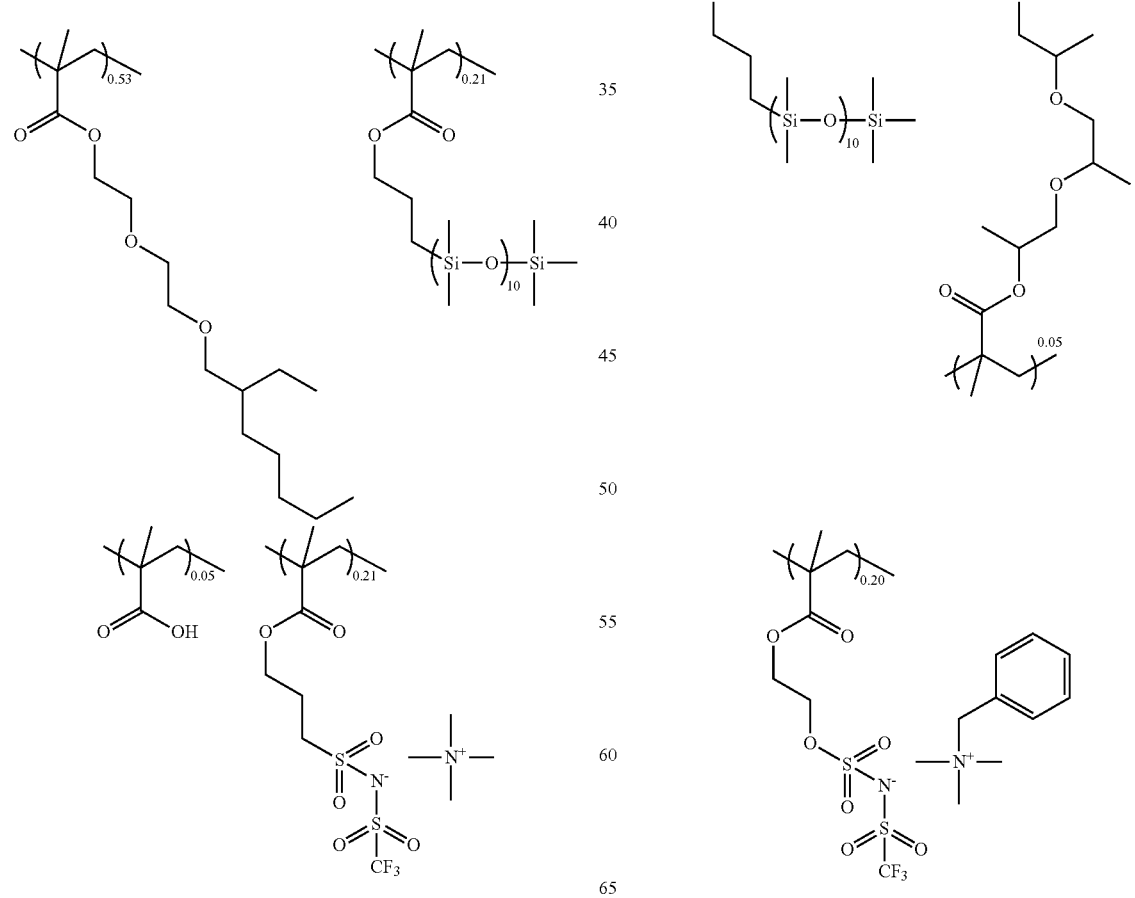
wherein, the repeating number represents the average.

Ionic Polymer 6
Mw=35,700
Mw/Mn=2.33
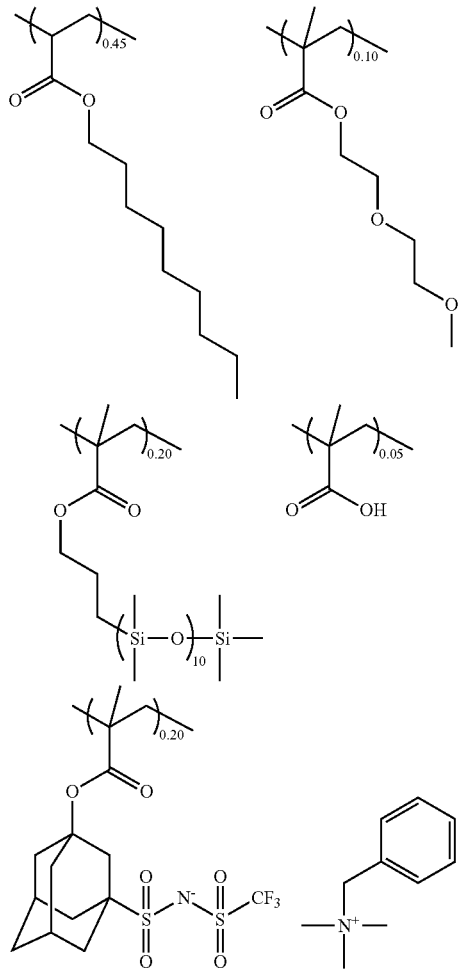
wherein, the repeating number represents the average.
Ionic Polymer 7
Mw=16,300
Mw/Mn-1.75
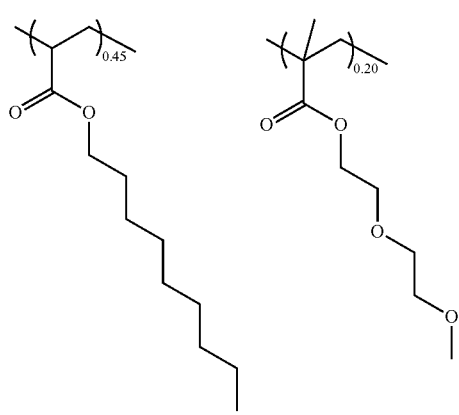
-continued
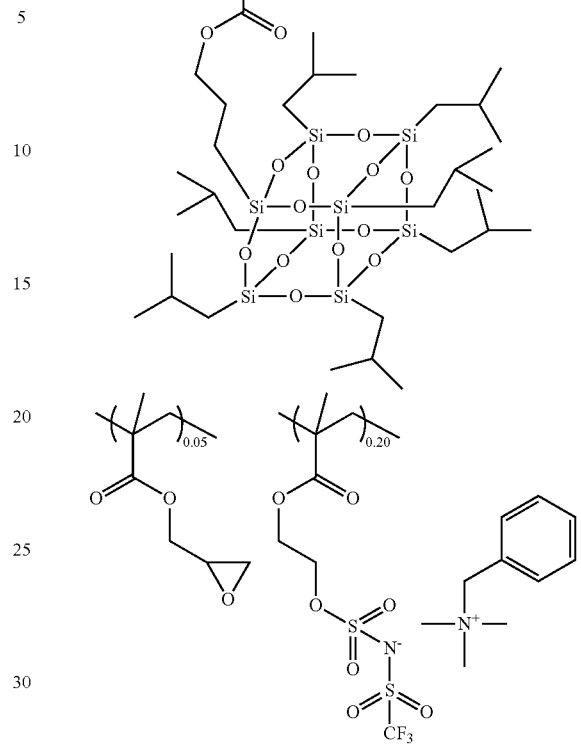
Ionic Polymer 8
Mw-50,100
Mw/Mn=2.21
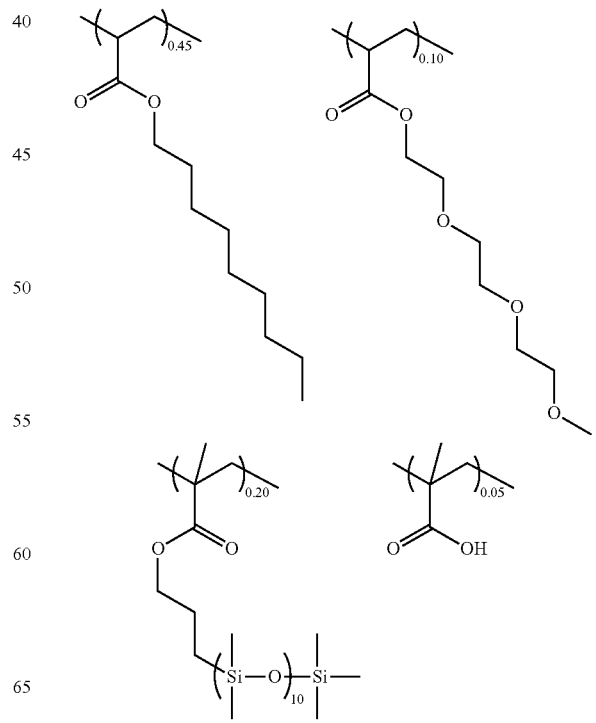

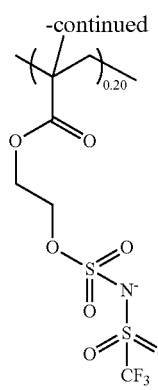
wherein, the repeating number represents the average.
Ionic Polymer 9
Mw=48,500
Mw/Mn=2.03
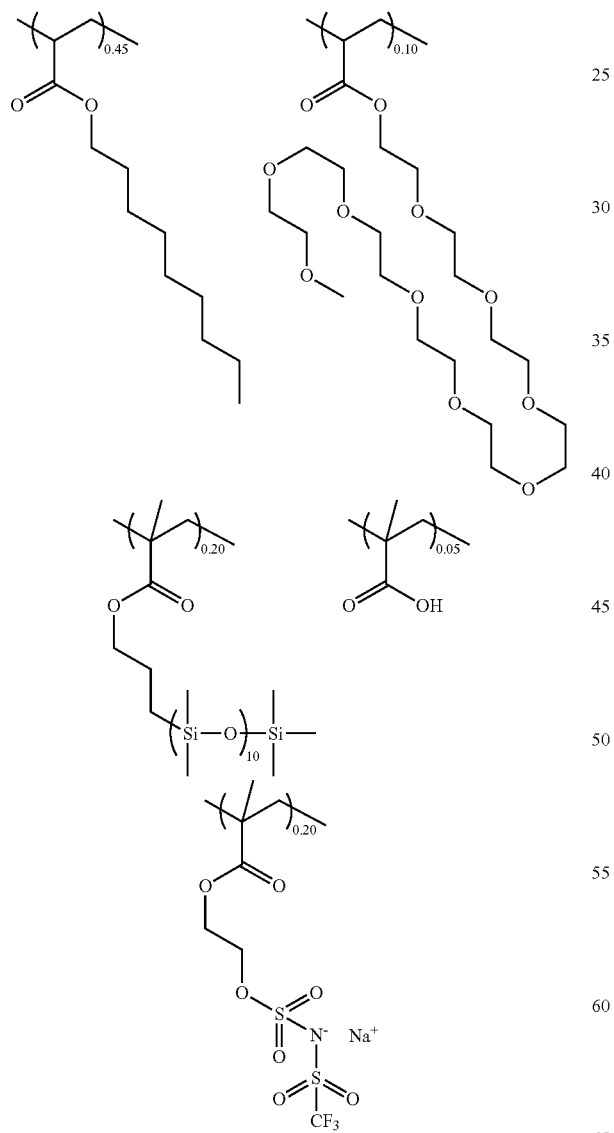
wherein, the repeating number represents the average.
Ionic Polymer 10
Mw=48,500
Mw/Mn-2.03
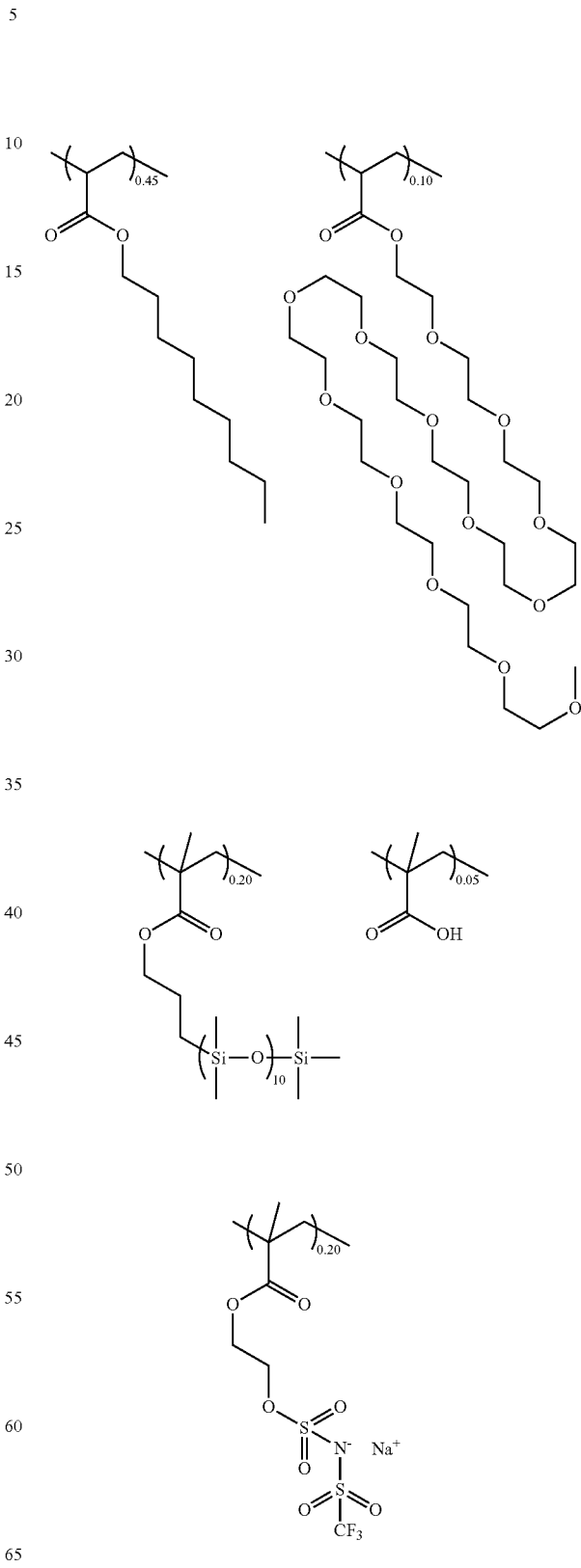
wherein, the repeating number represents the average.

Comparative Polymer 1
Mw=116,000
Mw/Mn=2.20

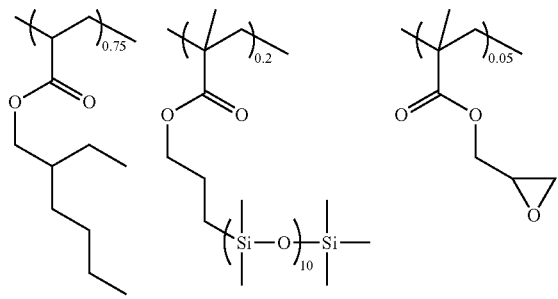

wherein, the repeating number represents the average.
Comparative Ionic Polymer 1
Mw=44,900
Mw/Mn=2.59

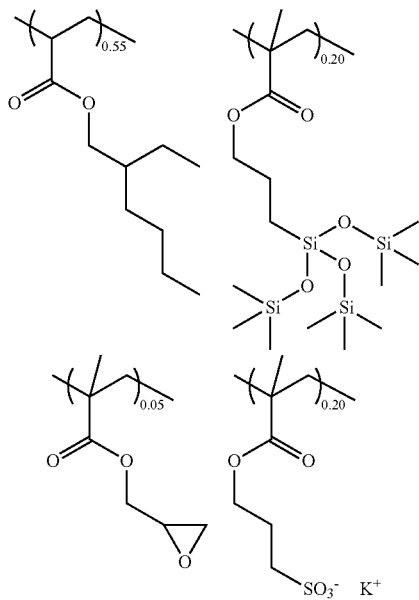

Comparative Ionic Polymer 2
Mw=57,900
Mw/Mn=1.89

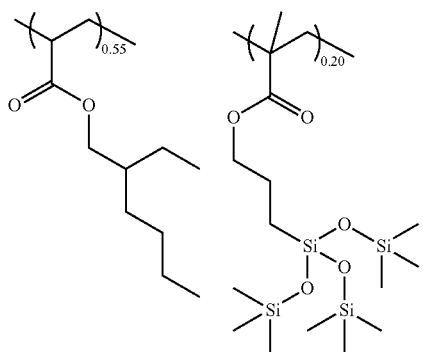

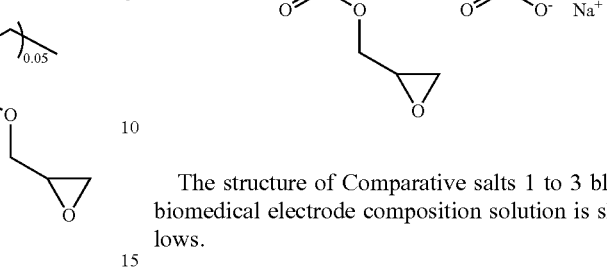

The structure of Comparative salts 1 to 3 blended into a biomedical electrode composition solution is shown as follows.

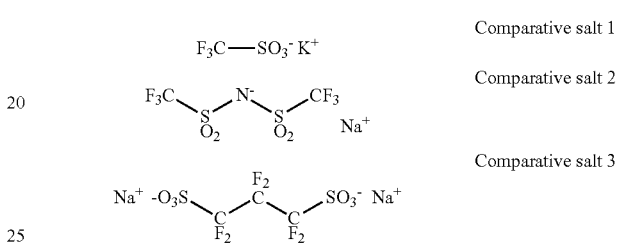

The structure of a crosslinking agent 1 blended into a biomedical electrode composition solution as an additive is shown as follows.

Crosslinking Agent 1

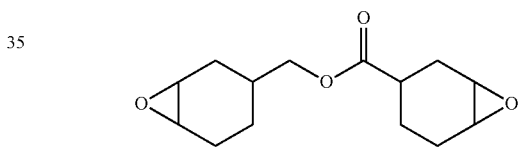

Conductive improvers (carbon black, carbon nanotube, gold-coated particle, silver-coated particle, and ITO particle) blended into a biomedical electrode composition solution as an additive are shown as follows.

Carbon black: Denka Black HS-100, Product from Denka Company Limited.

Carbon nanotube: Multi-walled 60 to 100 nm in diameter, 5 μm in length, Product from Sigma-Aldrich Co. LLC.

Gold-coated particle: Micropearl AU (100 μm in diameter), Product from SEKISUI CHEMICAL CO., LTD.

Silver-coated particle: silver-coated powder (30 μm in diameter), Product from MITSUBISHI MATERIALS Corporation ITO particle: ITO powder (0.03 μm in diameter), Product from MITSUBISHI MATERIALS Corporation Examples 1 to 14, Comparative Examples 1 to 5

Polymer compound solutions, Comparative salts, and additives (conductive improver and crosslinking agent) were blended with the compositions described in Table 1 to prepare biomedical electrode composition solutions (biomedical electrode composition solutions 1 to 14 and Comparative biomedical electrode composition solutions 1 to 5).

TABLE 1

| Biomedical electrode composition solution | Polymer solution (parts by mass) | comparative salt (parts by mass) | Additive (parts by mass) |
|---|---|---|---|
| Biomedical electrode composition solution 1 | Ionic polymer solution 1 (10) | — | Carbon black (0.3) |
| Biomedical electrode composition solution 2 | Ionic polymer solution 2 (10) | — | Carbon black (0.3) |
| Biomedical electrode composition solution 3 | Ionic polymer solution 3 (10) | — | Carbon black (0.3) |
| Biomedical electrode composition solution 4 | Ionic polymer solution 4 (10) | — | Carbon black (0.3) |
| Biomedical electrode composition solution 5 | Ionic polymer solution 5 (10) | — | Carbon black (0.3) |
| Biomedical electrode composition solution 6 | Ionic polymer solution 6 (10) | — | Carbon nanotube (0.2) Crosslinking agent 1 (0.05) |
| Biomedical electrode composition solution 7 | Ionic polymer solution 7 (10) | — | Carbon black (0.3) |
| Biomedical electrode composition solution 8 | Ionic polymer solution 1 (10) | — | Gold-coated particle (0.5) |
| Biomedical electrode composition solution 9 | Ionic polymer solution 1 (10) | — | Silver-coated particle (0.5) |
| Biomedical electrode composition solution 10 | Ionic polymer solution 1 (10) | — | ITO particle (0.7) |
| Biomedical electrode composition solution 11 | Ionic polymer solution 1 (10) | — | — |
| Biomedical electrode composition solution 12 | Ionic polymer solution 8 (10) | — | Carbon black (0.3) |
| Biomedical electrode composition solution 13 | Ionic polymer solution 9 (10) | — | Carbon black (0.3) |
| Biomedical electrode composition solution 14 | Ionic polymer solution 10 (10) | — | Carbon black (0.3) |
| Comparative biomedical electrode composition solution 1 | Comparative polymer solution 1 (10) | Comparative salt 1 (0.3) | Carbon black (0.3) |
| Comparative biomedical electrode composition solution 2 | Comparative polymer solution 1 (10) | Comparative salt 2 (0.3) | Carbon black (0.3) |
| Comparative biomedical electrode composition solution 3 | Comparative polymer solution 1 (10) | Comparative salt 3 (0.3) | Carbon black (0.3) |
| Comparative biomedical electrode composition solution 4 | Comparative ionic polymer solution 1 (10) | — | Carbon black (0.3) |
| Comparative biomedical electrode composition solution 5 | Comparative ionic polymer solution 2 (10) | — | Carbon black (0.3) |

Evaluation of Conductivity

Figure 3:
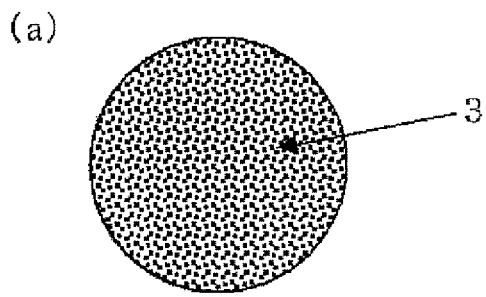
FIG. 3(a) is a schematic illustration of a biomedical electrode manufactured in an Example of the present invention viewed from the living body contact layer side.
FIG. 3(b) is a schematic illustration of a biomedical electrode manufactured in an Example of the present invention viewed from the conductive substrate side.
Figure 3:
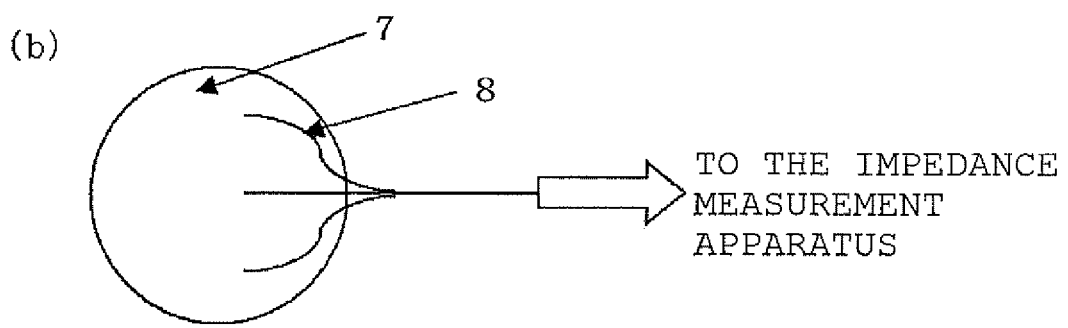
Figure 4:
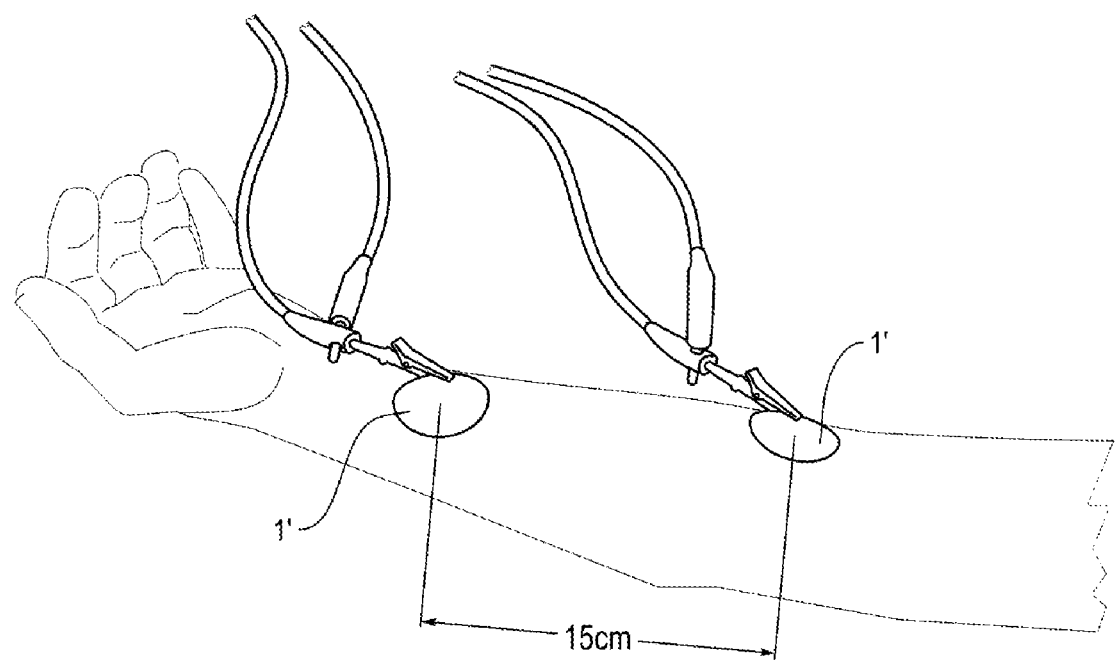
FIG. 4 is a schematic view showing that the impedance is measured on the skin surface, using a biomedical electrode manufactured in an Example of the present invention.

A biomedical electrode composition solution was applied to an aluminum disk 3 cm in diameter and 0.2 mm in thickness using an applicator, air-dried at room temperature for 6 hours, and then baked in nitrogen atmosphere at 130° C. for 30 minutes using an oven to be cured to prepare 4 biomedical electrodes per one biomedical electrode composition solution. The biomedical electrodes thus obtained, as shown in FIGS. 3(a) and 3(b), includes a living body contact layer 3 on one surface, and an aluminum disk 7 as a conductive substrate on the other surface. Then, as shown in FIG. 3(b), a copper wire 8 is attached to the surface of an aluminum disk 7 on a side that is not covered with the living body contact layer with adhesive tape, which was defined as an extraction electrode, and this electrode was connected to an impedance measurement apparatus. As shown in FIG. 4, 2 biomedical electrodes 1' were applied to the human arm's skin so that the skin is connected to the living body contact layer side, with an interval of 15 cm. The initial impedance was measured with an alternating current impedance measurement apparatus SI 1260 from Solartron Corporation with various frequencies. Then, after the two residual biomedical electrodes were immersed in pure water for one hour and the water was dried, the impedance on the skin was measured by the above method. Table 2 shows the impedance with a frequency of 1,000 Hz.

Evaluation of Adhesion

The biomedical electrode composition solutions were applied to PEN (polyethylene naphthalate) substrate 100 μm in thickness using an applicator, and air-dried at room temperature for 6 hours, then using an oven, baked in nitrogen atmosphere at 130° C. for 30 minutes to be cured to prepare an adhesive film. A 25 mm-width tape was cut from the adhesive film, and this was attached to a stainless plate (SUS304) by pressure, and left unattended at room temperature for 20 hours. The force required to peel a tape containing an adhesive agent from the stainless plate at a speed of 300 mm/min with an angle of 180 degrees (N/25 mm) was measured with a tensile tester. Table 2 shows the results.

Measurement of Thickness of Living Body Contact Layer

In the biomedical electrodes prepared in the conductivity evaluation test, the thickness of living body contact layers was measured with a micrometer. Table 2 shows the results.

As shown in Table 2, in Examples 1 to 14 where the biomedical electrode composition of the present invention in which a polymer compound having a specific structure was blended to form a living body contact layer, the initial impedance was low, and even after the biomedical electrode was immersed in water and dried, no changes in impedance were found. In the biomedical electrodes obtained in Examples 1 to 14, the initial conductivity was high, and there were no significant changes in conductivity even though the biomedical electrode was soaked in water or dried. These biomedical electrodes in Examples 1 to 14 have adhesion as favorable as that in Comparative Examples 1 to 5, are light-weight, excellent in biocompatibility, and can be manufactured at low cost.

Meanwhile, in Comparative Example 1 to 3 for forming a living body contact layer using biomedical electrode compositions in which a polymer compound including no repeating unit "a" and Comparative salt are blended, the initial impedance was low, but after the biomedical electrode

TABLE 2

| | Biomedical electrode composition solution | Adhesion (N/25 mm) | Thickness of living body contact layer (μm) | Initial impedance (Ω) | Impedance after immersion in water (Ω) |
|---|---|---|---|---|---|
| Example 1 | Biomedical electrode composition solution 1 | 1.3 | 140 | $1.0E^3$ | $1.1E^3$ |
| Example 2 | Biomedical electrode composition solution 2 | 1.6 | 125 | $8.2E^2$ | $7.4E^2$ |
| Example 3 | Biomedical electrode composition solution 3 | 1.8 | 110 | $6.8E^3$ | $4.1E^3$ |
| Example 4 | Biomedical electrode composition solution 4 | 2.1 | 104 | $6.2E^3$ | $6.1E^3$ |
| Example 5 | Biomedical electrode composition solution 5 | 2.7 | 170 | $2.2E^3$ | $3.2E^3$ |
| Example 6 | Biomedical electrode composition solution 6 | 2.0 | 110 | $1.6E^3$ | $1.3E^3$ |
| Example 7 | Biomedical electrode composition solution 7 | 1.6 | 180 | $8.8E^3$ | $8.9E^3$ |
| Example 8 | Biomedical electrode composition solution 8 | 1.1 | 150 | $8.6E^3$ | $8.9E^3$ |
| Example 9 | Biomedical electrode composition solution 9 | 1.8 | 120 | $9.8E^3$ | $9.5E^3$ |
| Example 10 | Biomedical electrode composition solution 10 | 1.6 | 250 | $1.2E^4$ | $1.3E^4$ |
| Example 11 | Biomedical electrode composition solution 11 | 3.4 | 120 | $7.4E^4$ | $8.8E^4$ |
| Example 12 | Biomedical electrode composition solution 12 | 1.2 | 190 | $8.0E^2$ | $7.1E^2$ |
| Example 13 | Biomedical electrode composition solution 13 | 1.1 | 175 | $7.2E^2$ | $6.4E^2$ |
| Example 14 | Biomedical electrode composition solution 14 | 1.0 | 165 | $4.2E^2$ | $3.4E^2$ |
| Comparative Example 1 | Comparative biomedical electrode composition solution 1 | 2.3 | 120 | $2.2E^4$ | $5.3E^5$ |
| Comparative Example 2 | Comparative biomedical electrode composition solution 2 | 2.2 | 130 | $3.2E^4$ | $7.3E^5$ |
| Comparative Example 3 | Comparative biomedical electrode composition solution 3 | 1.6 | 120 | $1.2E^4$ | $9.3E^5$ |
| Comparative Example 4 | Comparative biomedical electrode composition solution 4 | 4.5 | 140 | $2.9E^7$ | $1.9E^7$ |
| Comparative Example 5 | Comparative biomedical electrode composition solution 5 | 4.5 | 140 | $7.9E^7$ | $8.9E^7$ | was immersed in water and dried, the impedance significantly increased to a higher-digit number. The biomedical electrodes in Comparative Examples 1 to 3 showed high initial conductivity, but when they were soaked in water or dried, all the conductivity significantly declined.

In Comparative Examples 4 and 5 where a polymer in which salt of fluoroalkylated bissulfonylimide acid on either side is not copolymerized (or, a polymer compound having no repeating unit "a") is used, the initial impedance was high. The biomedical electrodes in Comparative Examples 4 and 5 show low initial conductivity only.

The above observations found that the biomedical electrode for forming a living body contact layer, using the biomedical electrode composition of the present invention, is excellent in conductivity, biocompatibility, adhesion to a conductive substrate, and holding force of a conductive material. Such a biomedical electrode doesn't significantly decline the conductivity even though the biomedical electrode is soaked in water or dried, is light-weight, and can be manufactured at low cost.

It should be noted that the present invention is not limited to the above-described embodiments. The above-described embodiments are described for illustrative purposes, and those having substantially the same configuration and those providing the same operational advantage as the technical concept described in the claims of the present invention are all encompassed in the technical scope of the present invention.

EXPLANATIONS OF LETTERS OR NUMERALS 1, 1' . . . Biomedical electrode, 2 . . . Conductive substrate,
3 . . . Living body contact layer,
4 . . . Carbon material, 5 . . . Polymer compound (resin),
6 . . . Living body, 7 . . . Aluminum disk, 8 . . . Cupper wire.

What is claimed is:
1. A biomedical electrode composition comprising a polymer compound comprising
an ionic repeating unit "a" that is a repeating unit of a sodium salt, a potassium salt, or an ammonium salt and includes a partial structure represented by the following general formula (1),
a repeating unit "b" of (meth)acrylate, the repeating unit "b" being a repeating unit selected from any of a repeating unit obtained from at least one monomer represented by the following formulae (T1) to (T10) and a repeating unit represented by the following general formula (T11), and
a repeating unit "c" having a fluorine atom or a silicon atom, the repeating unit "c" being a repeating unit selected from any of a repeating unit obtained from at least one monomer represented by the following formulae (C1) to (C7);

(1)

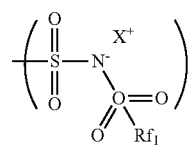

wherein,
$Rf_1$ represents a linear, or a branched alkyl group having 1 to 4 carbon atoms, having at least one fluorine atom; and $X^+$ represents any of a sodium ion, a potassium ion, or an ammonium ion;

wherein each of "a", "b" and "c" independently satisfies the equations $0<a<1.0$, $0<b<1.0$, $0<c<1.0$, $0<a+b+c<1.0$, formulae (T1) to (T11) are:

(T1)

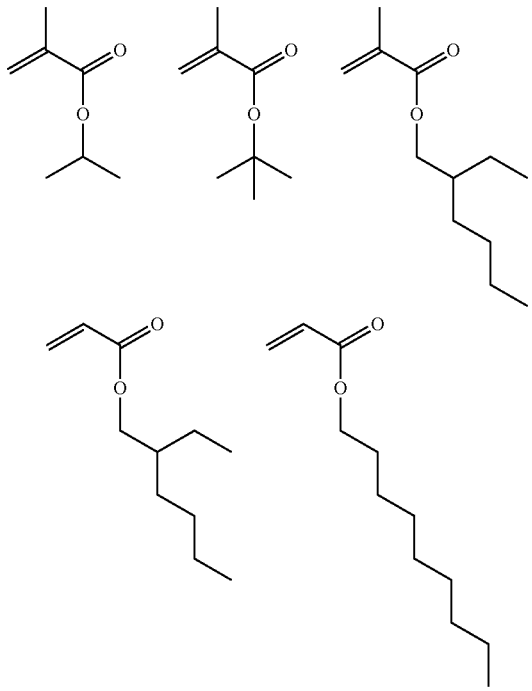

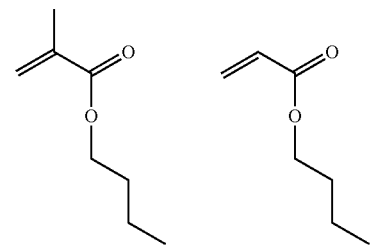

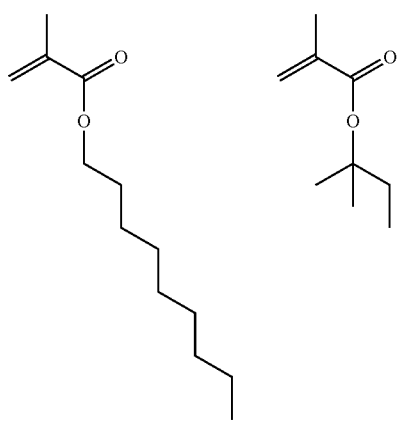

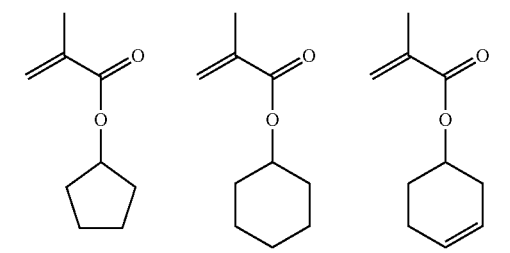
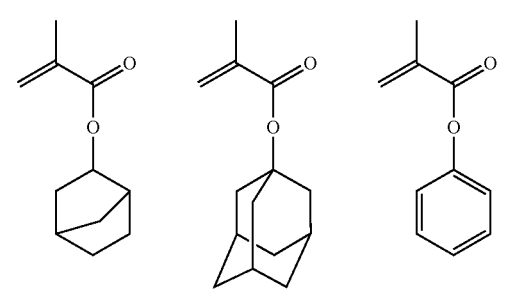
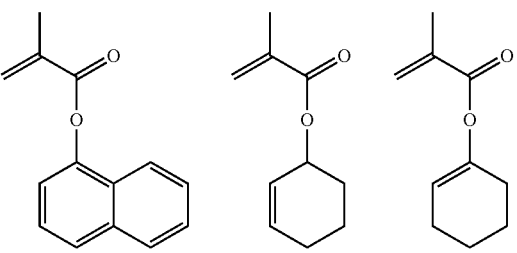
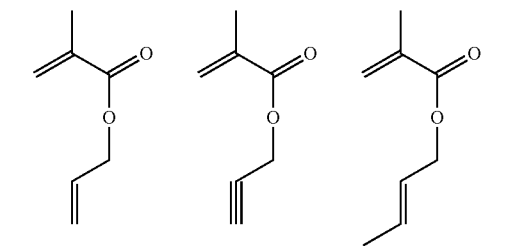
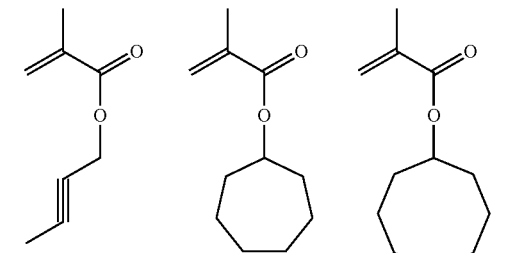
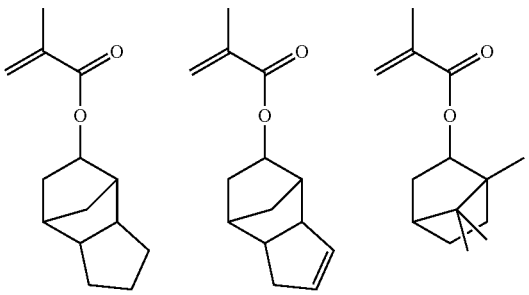
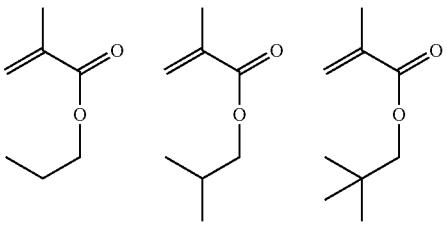
(T2)
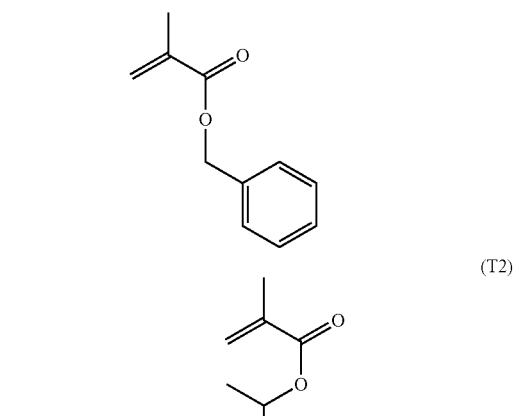
(T3)
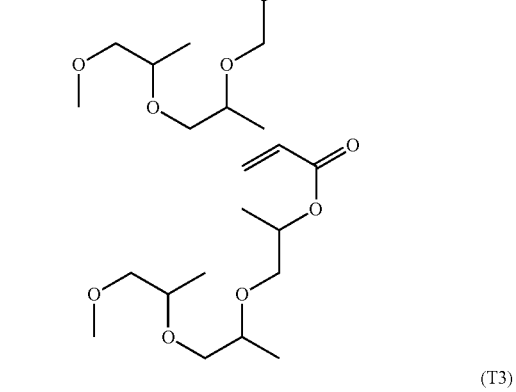
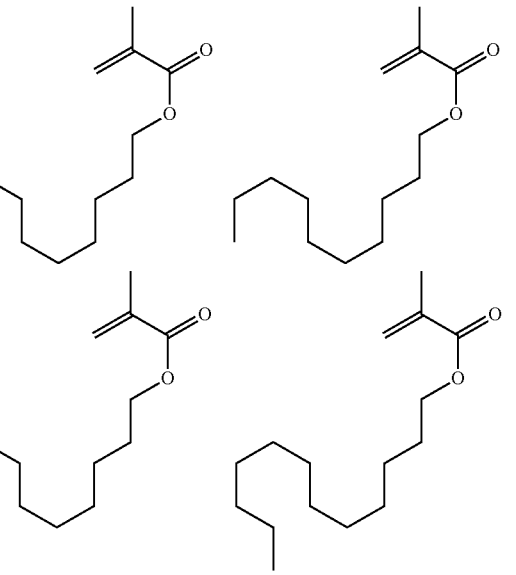

93
94
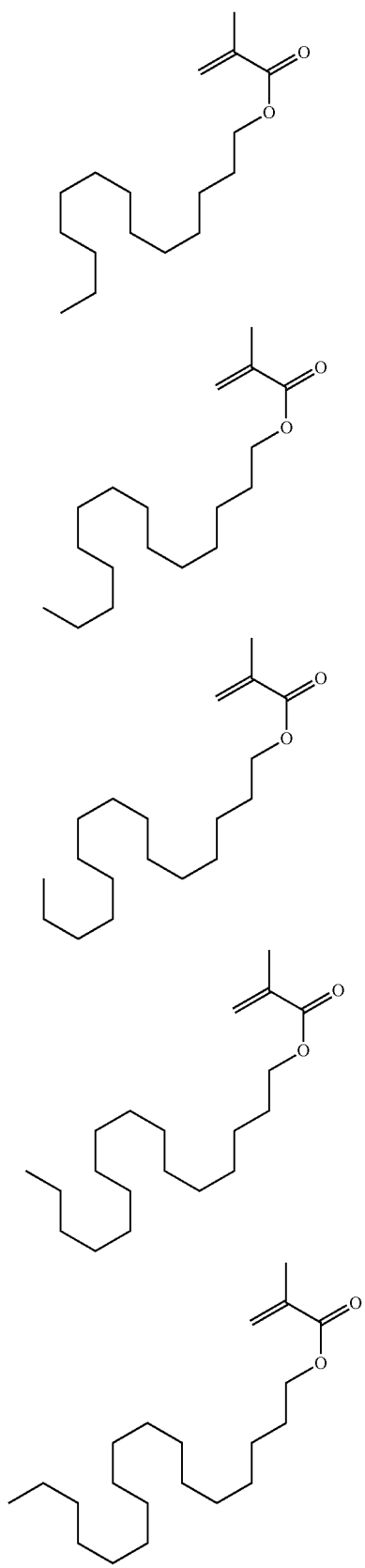
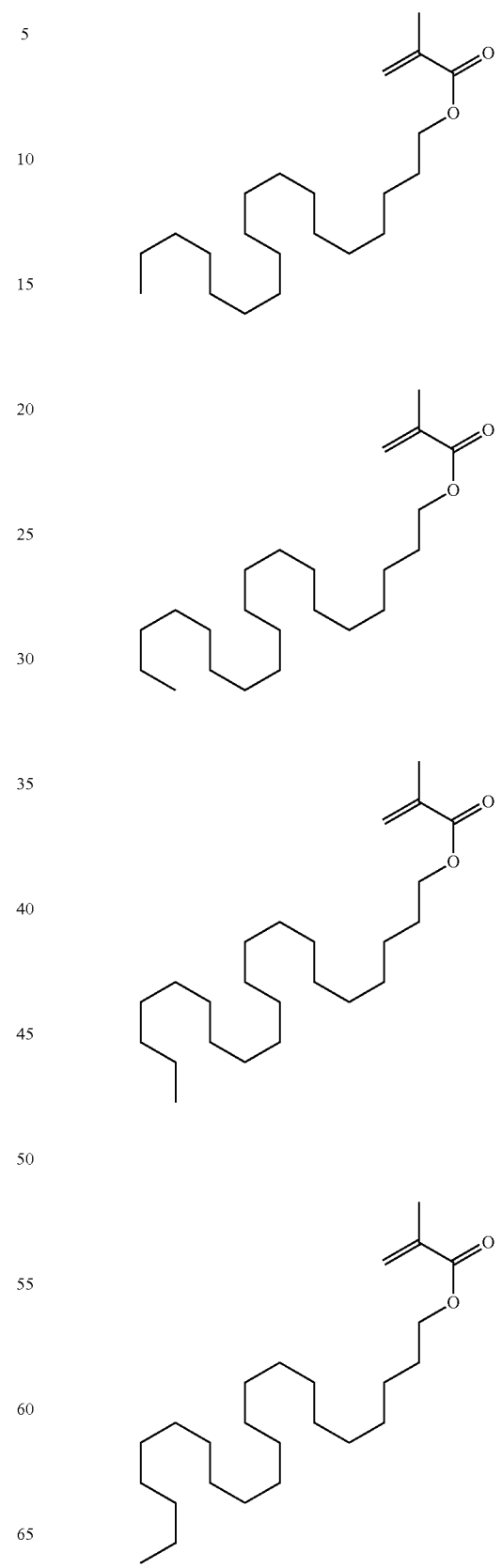

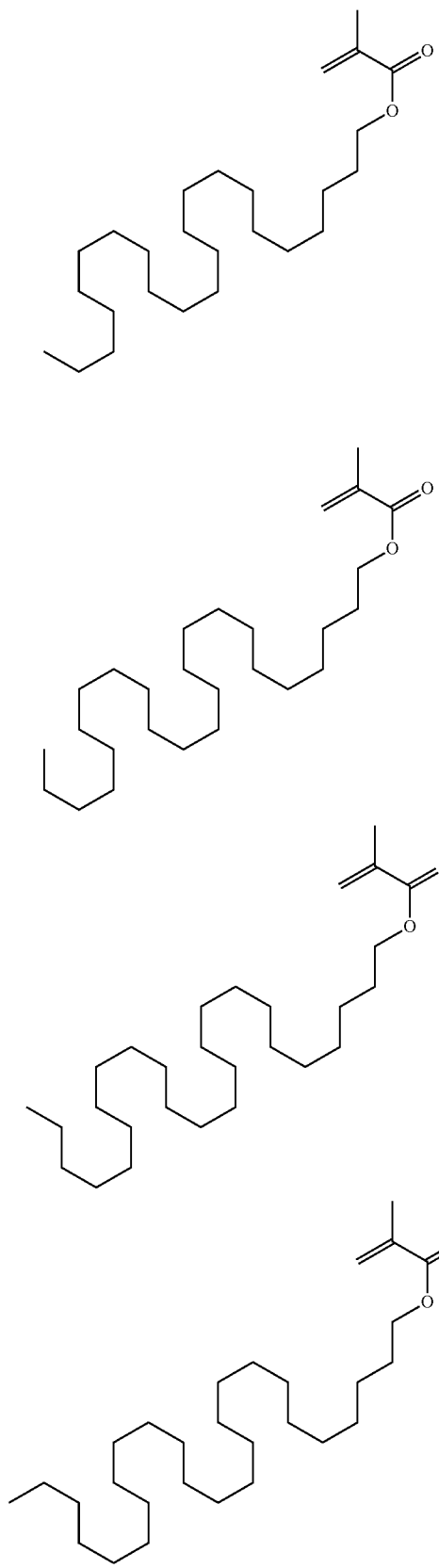
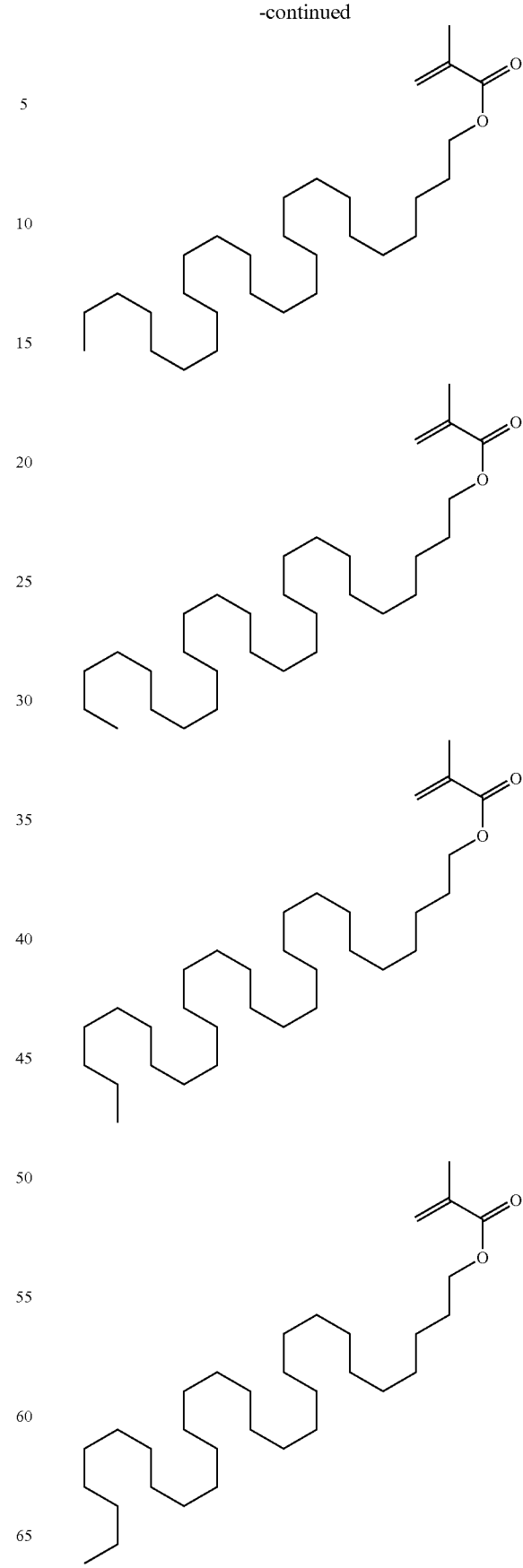

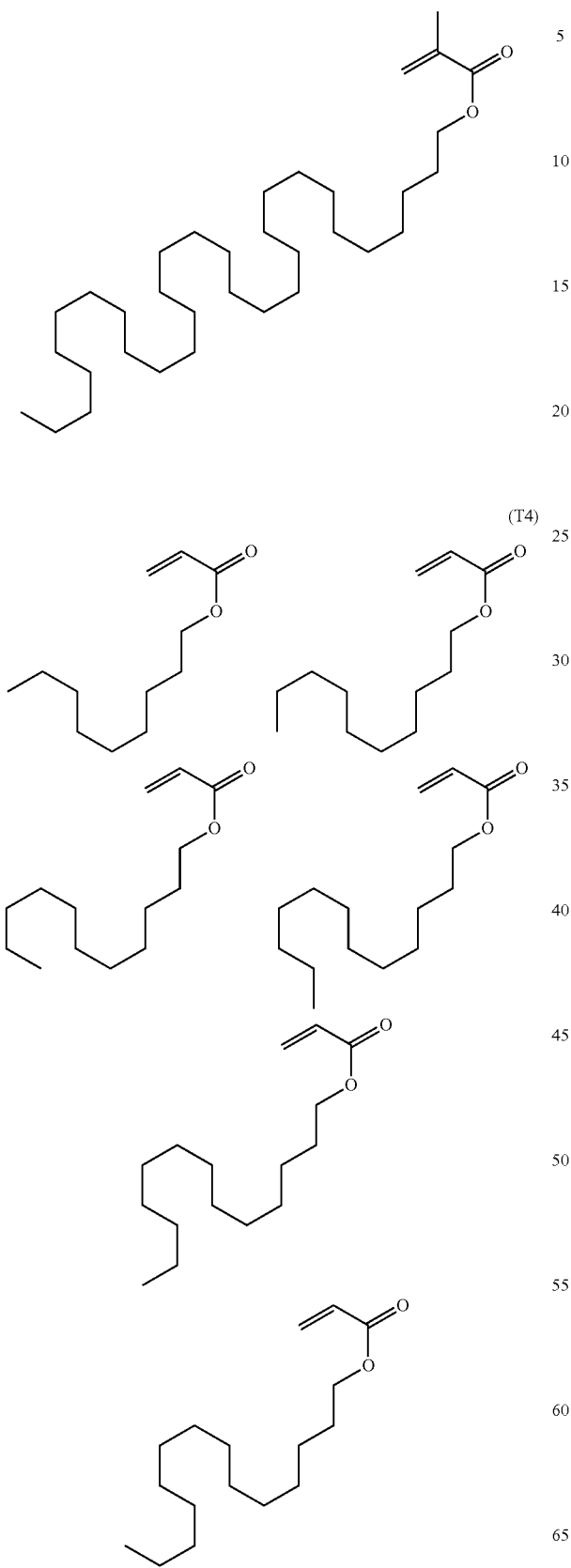
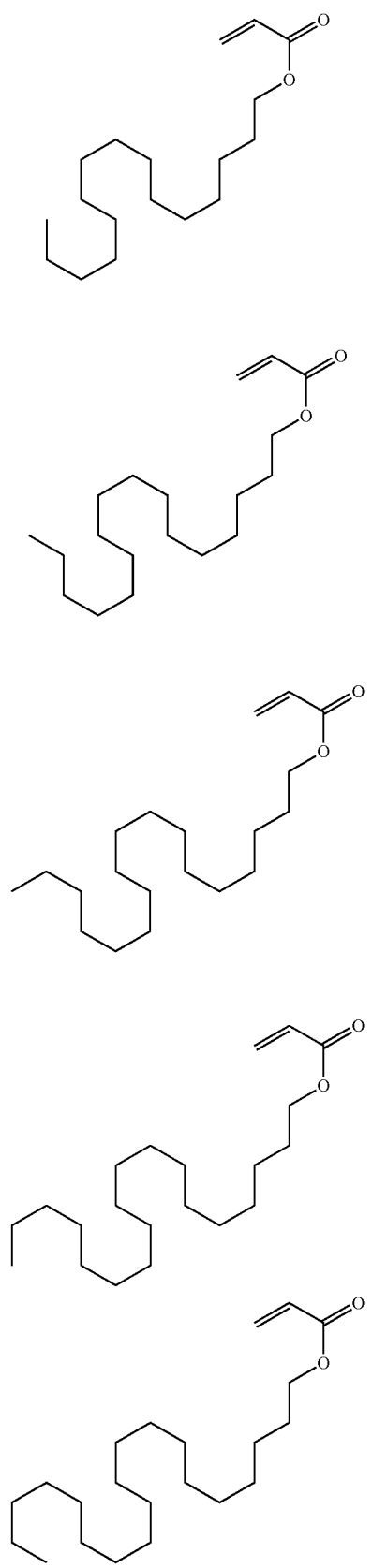

99
-continued
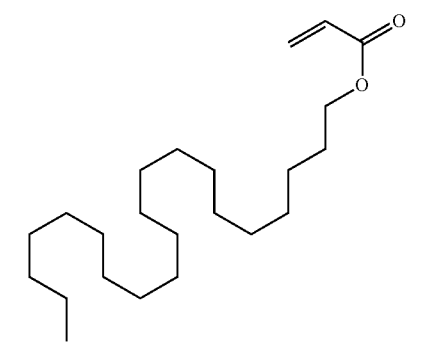
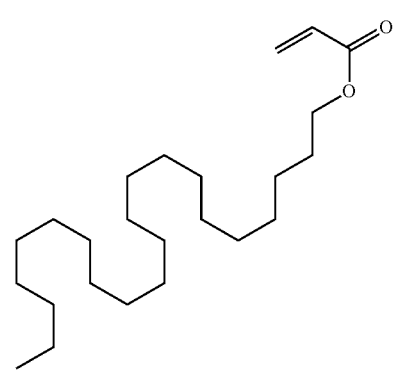
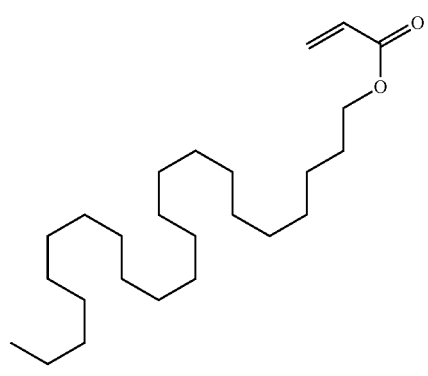
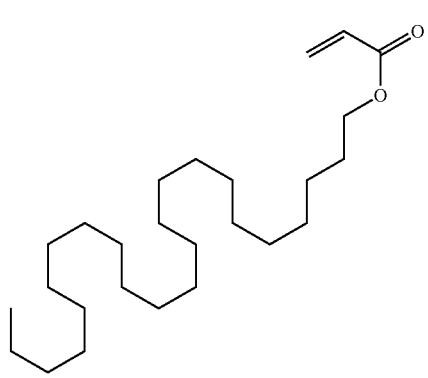
100
-continued
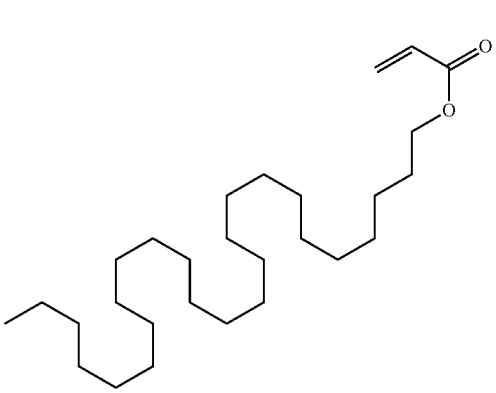
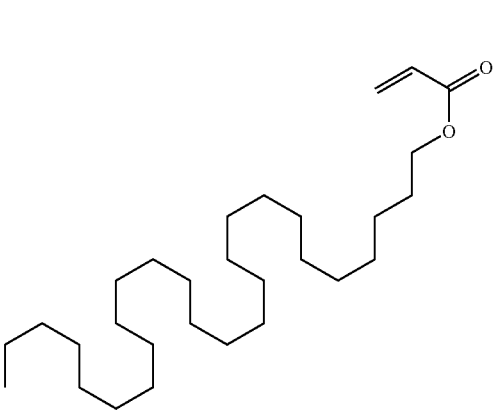
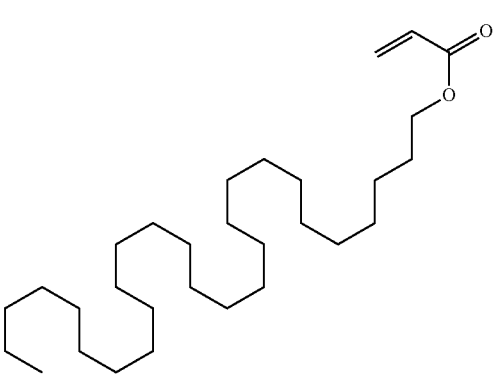

101
-continued
102
-continued
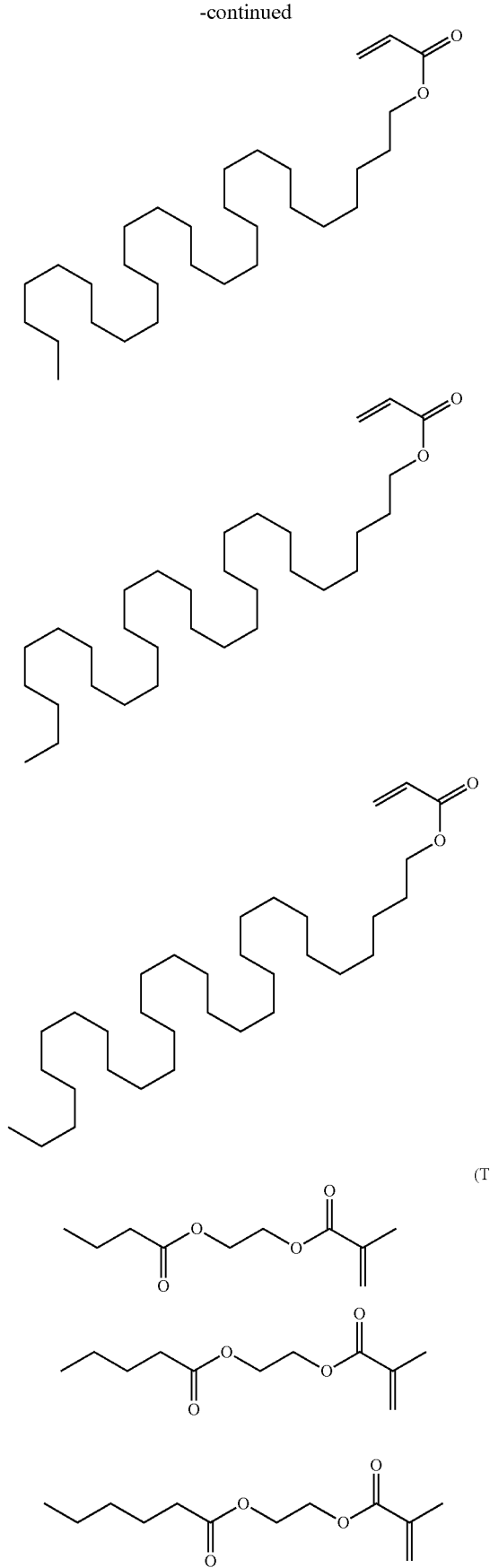
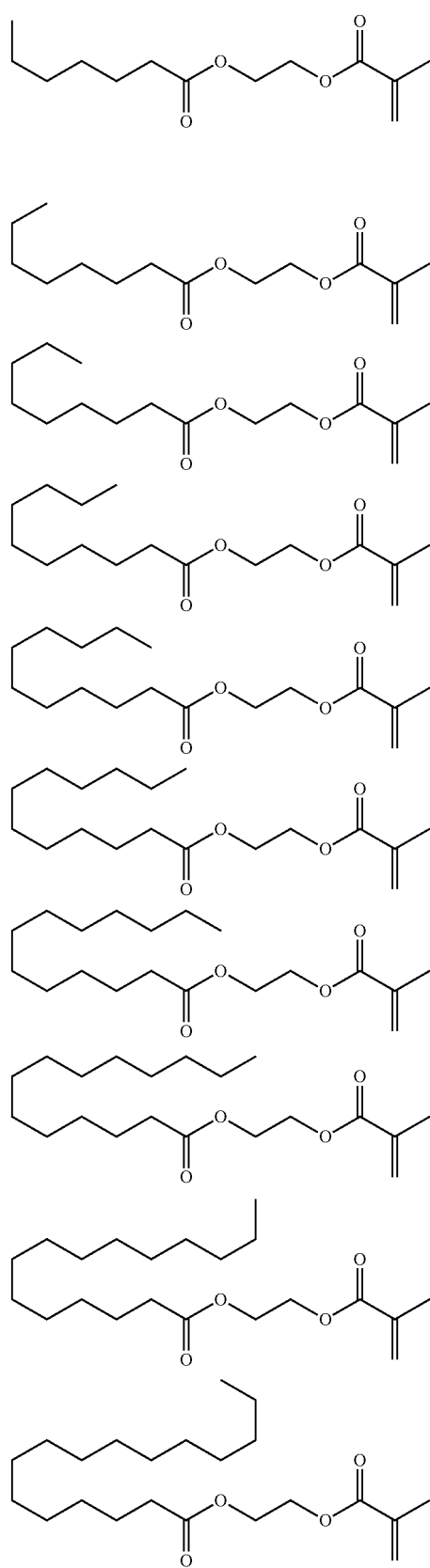
(T5)

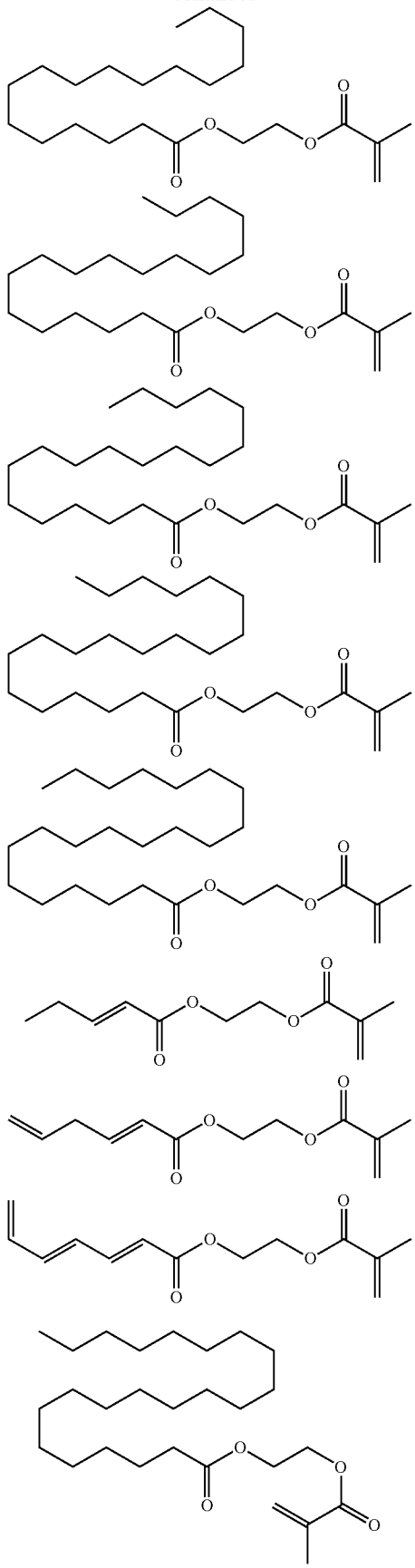
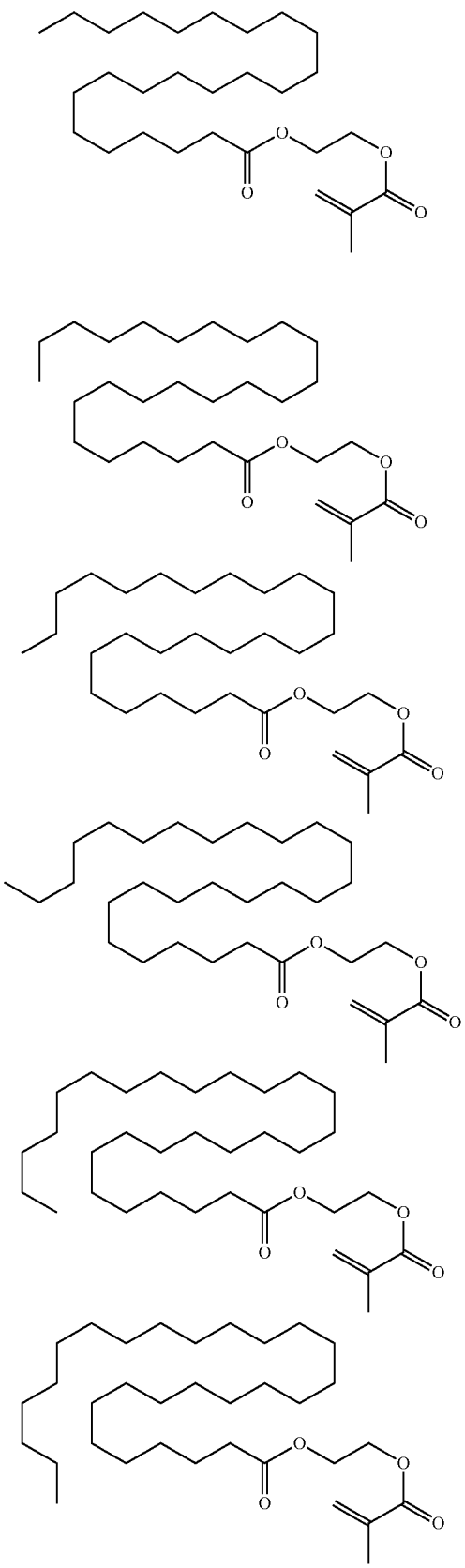

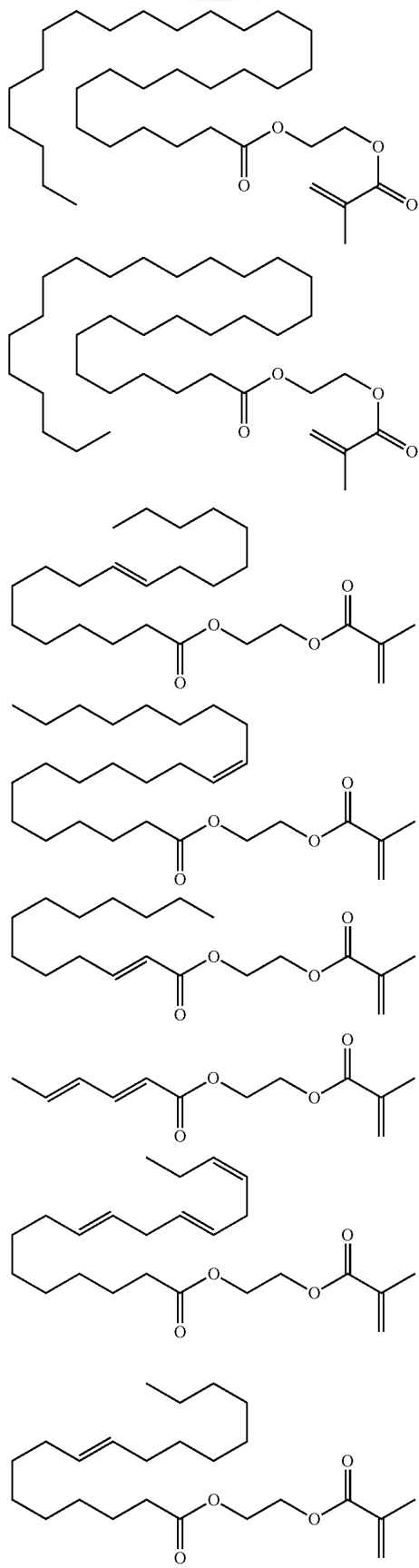
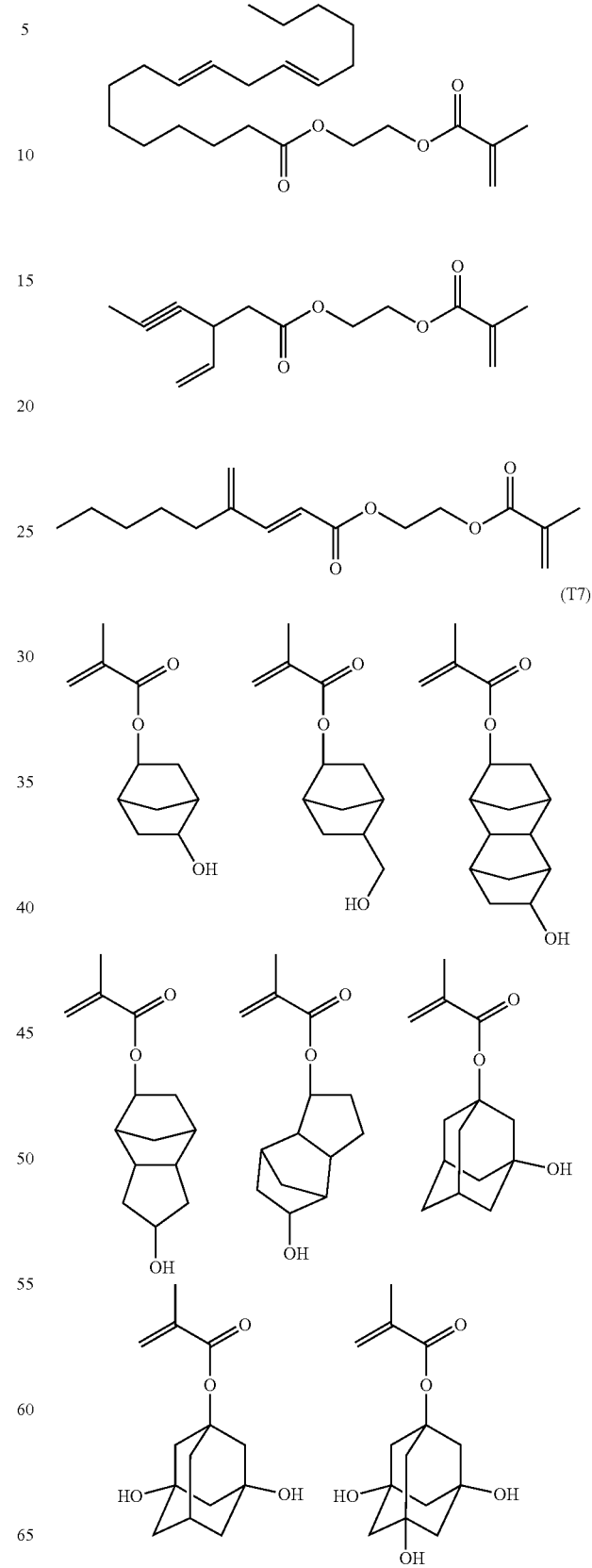

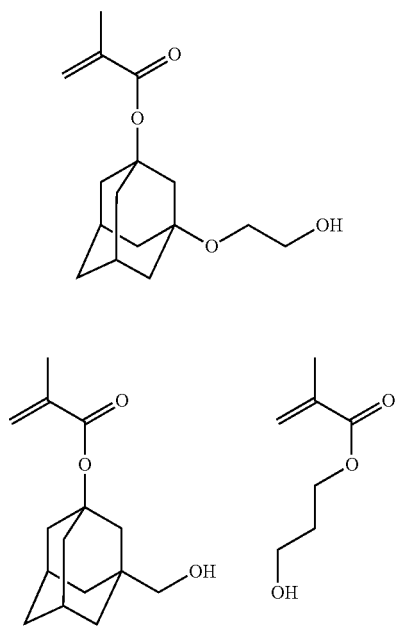
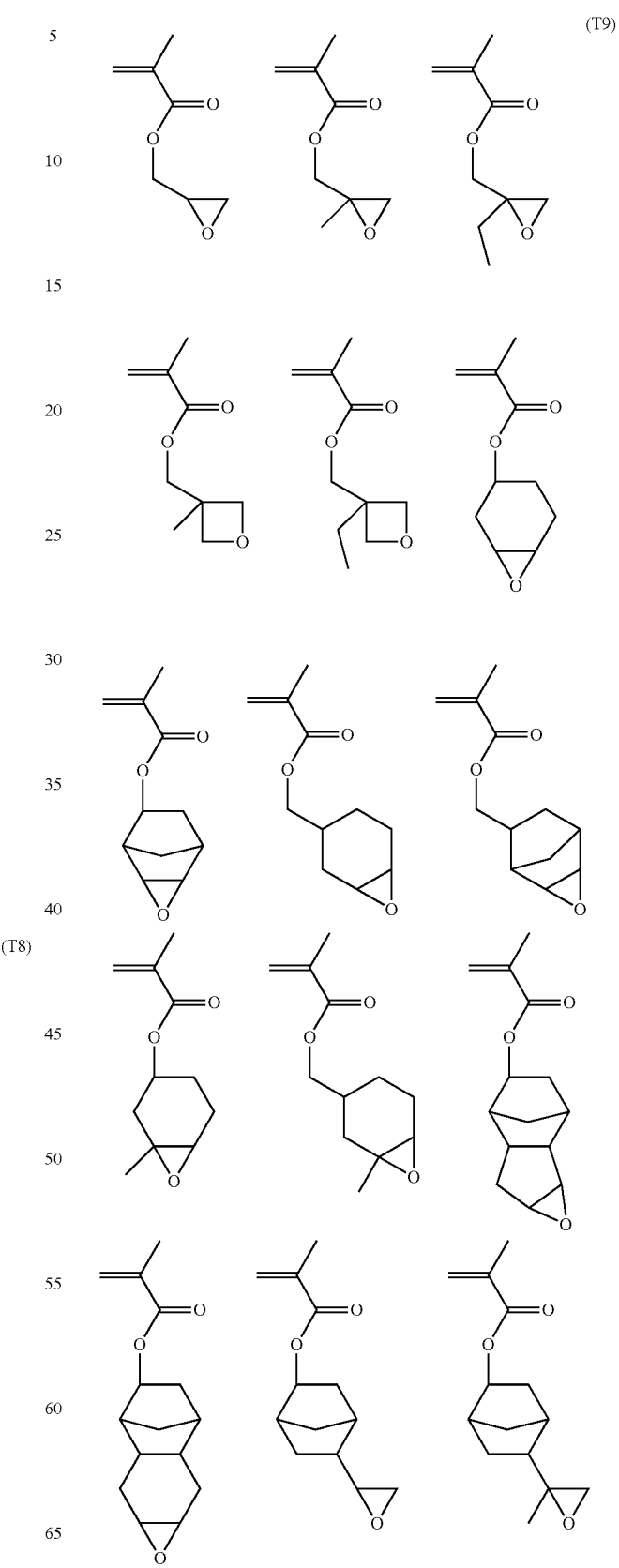
(T8)
(T9)

109
-continued
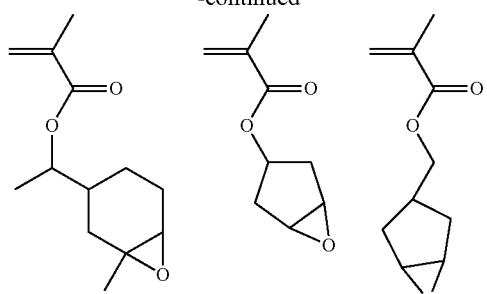
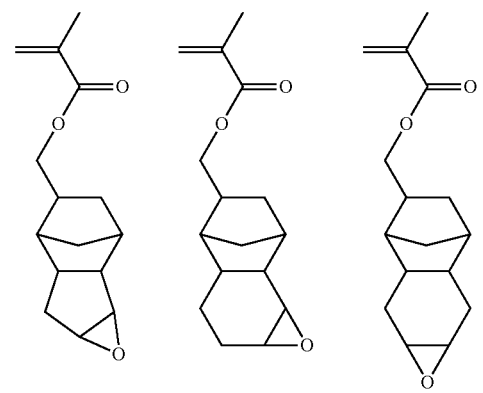
110
-continued
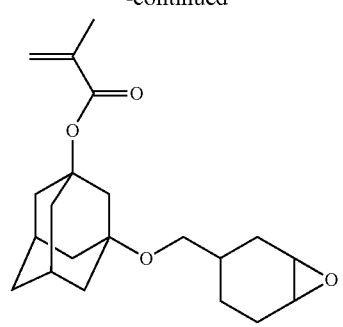
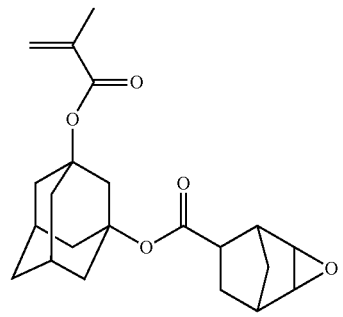
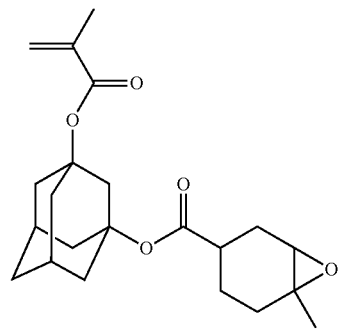
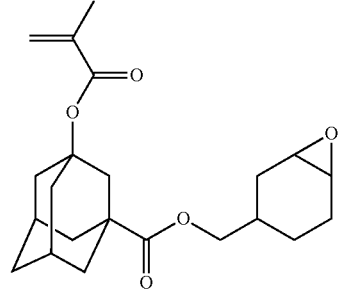
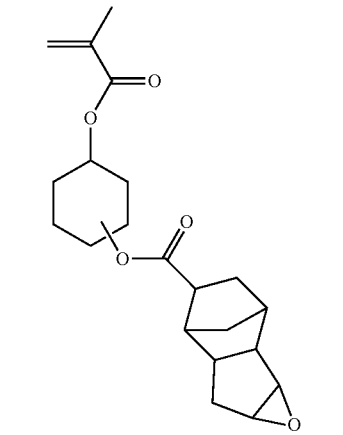
(T10)

111
-continued
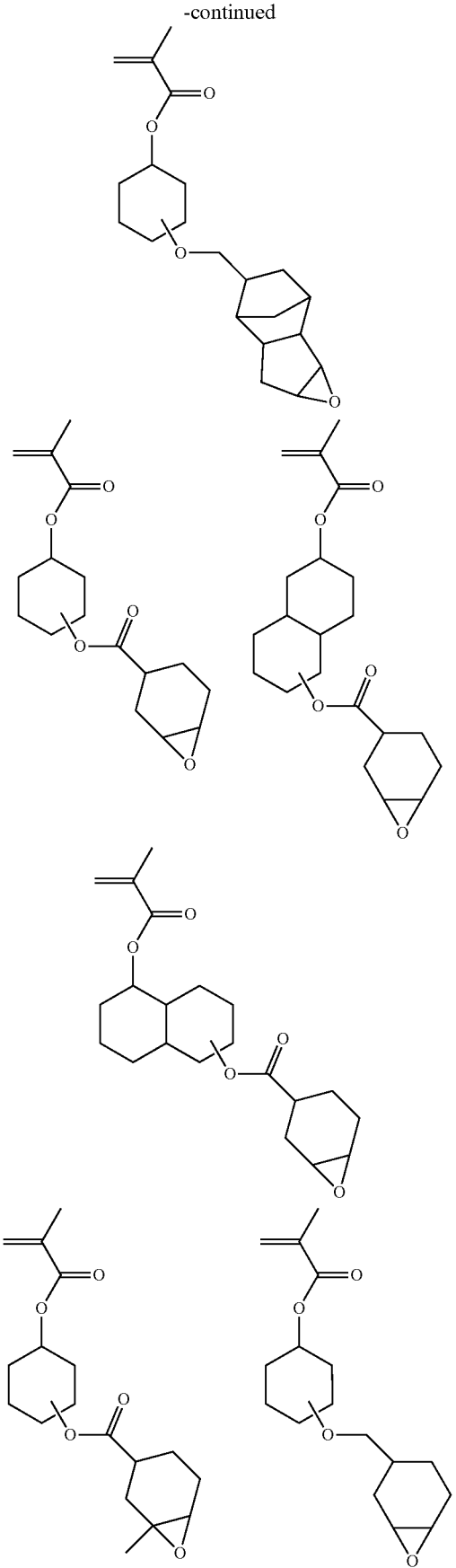
112
-continued
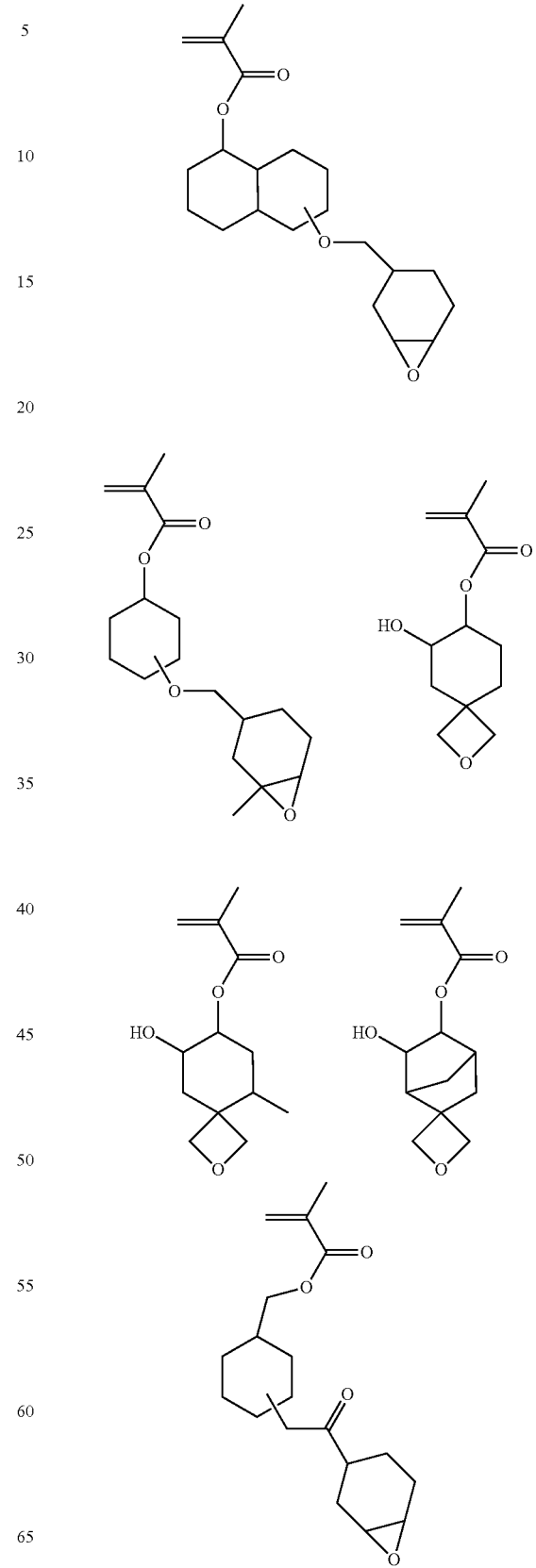

-continued
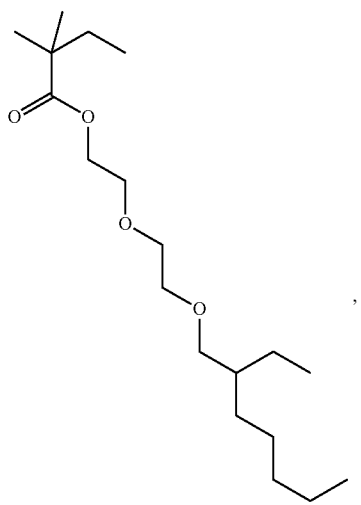
and
formulae (C1) to (C7) are
(C1)
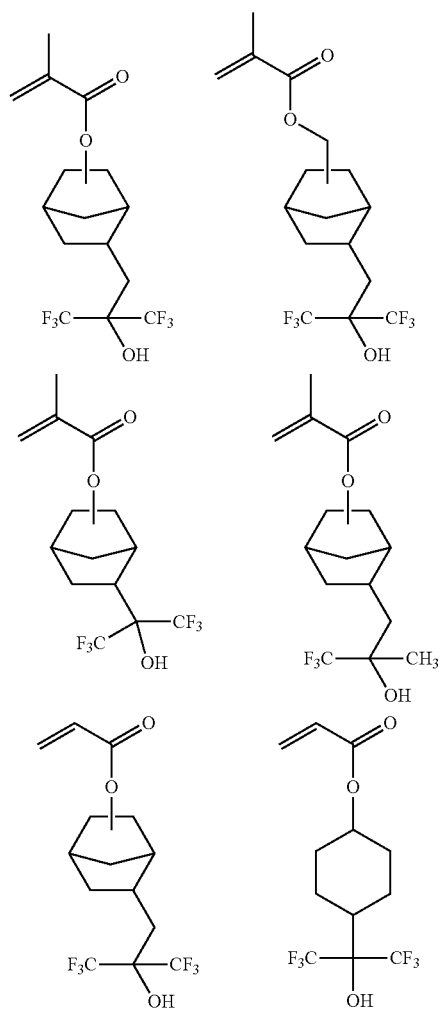
-continued
(T11)
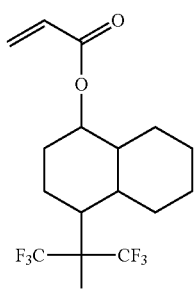 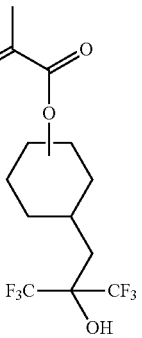
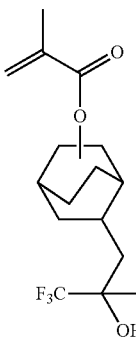 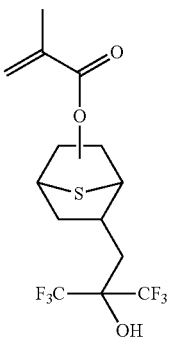
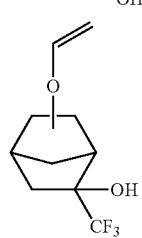 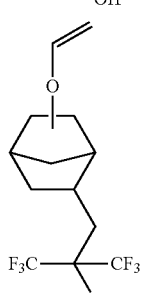
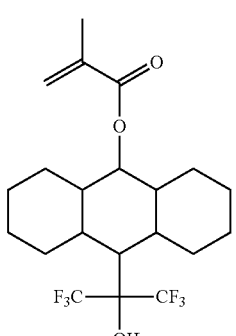 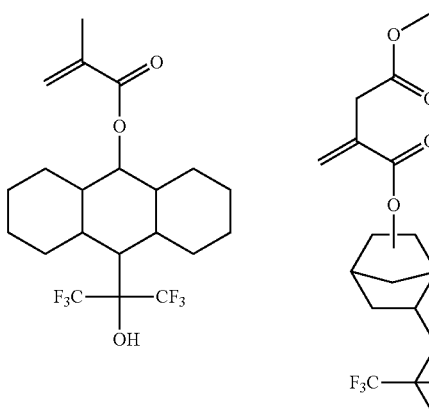
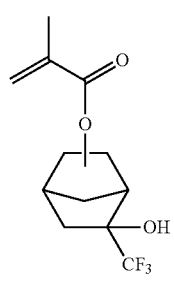 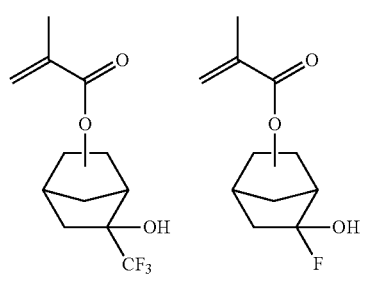 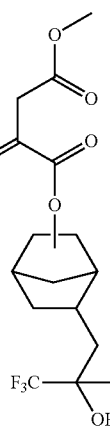

115
-continued
116
-continued
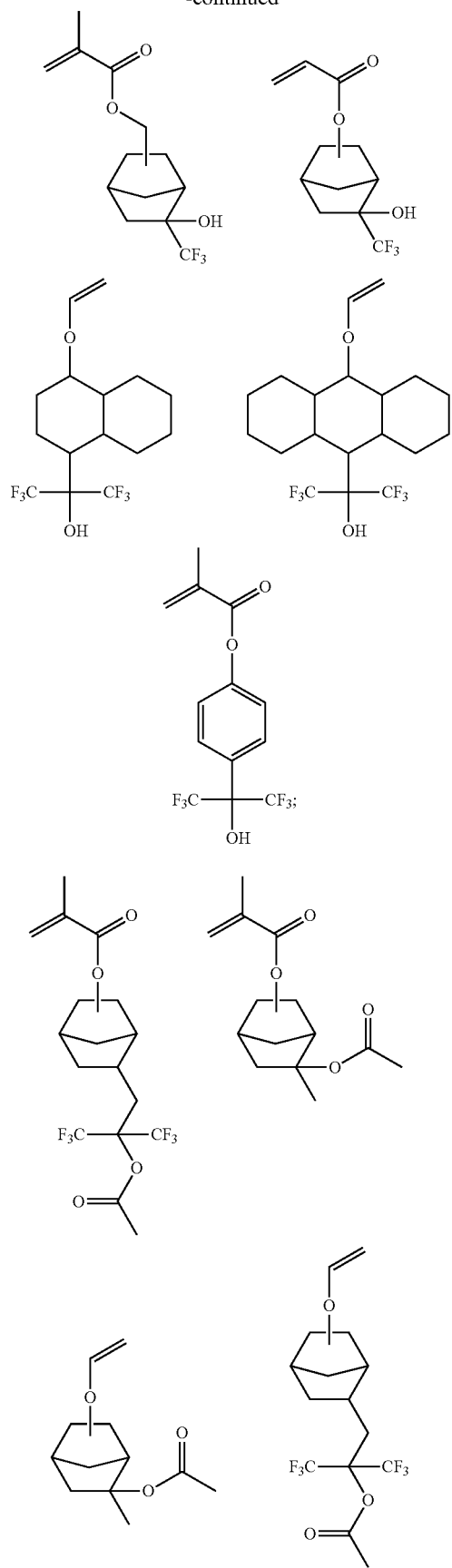
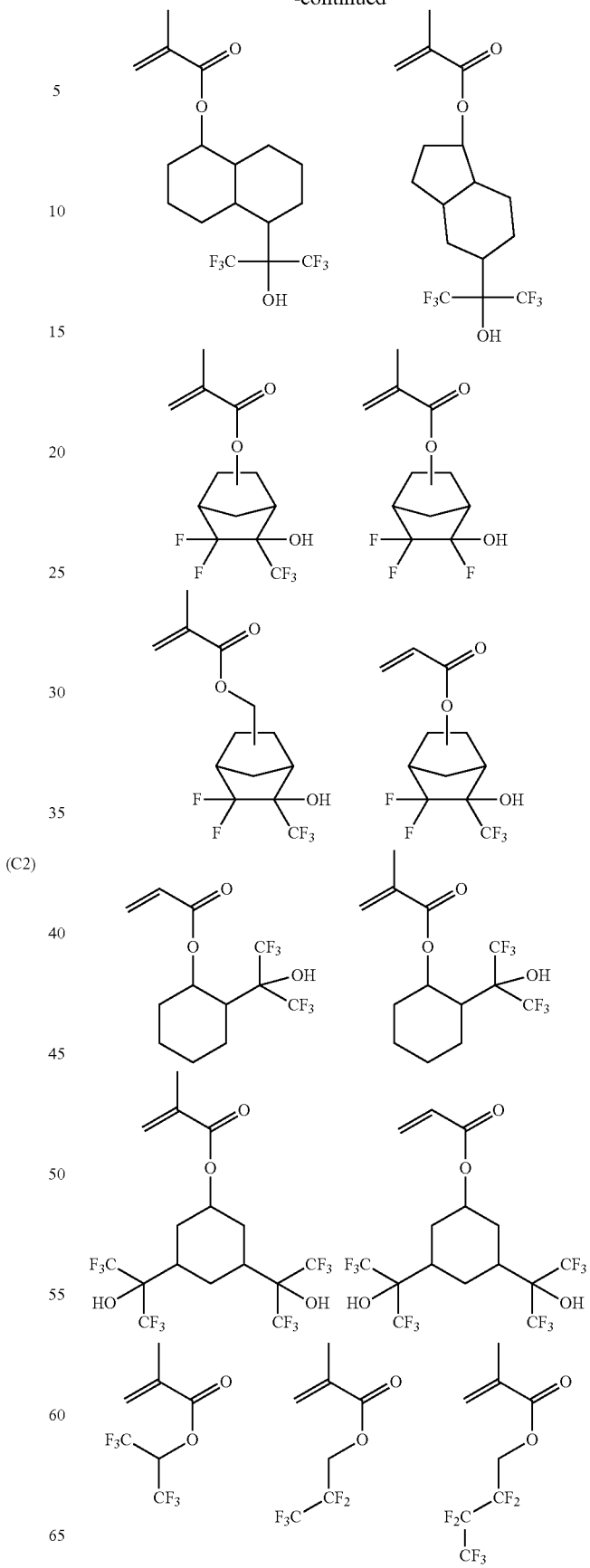
(C2)

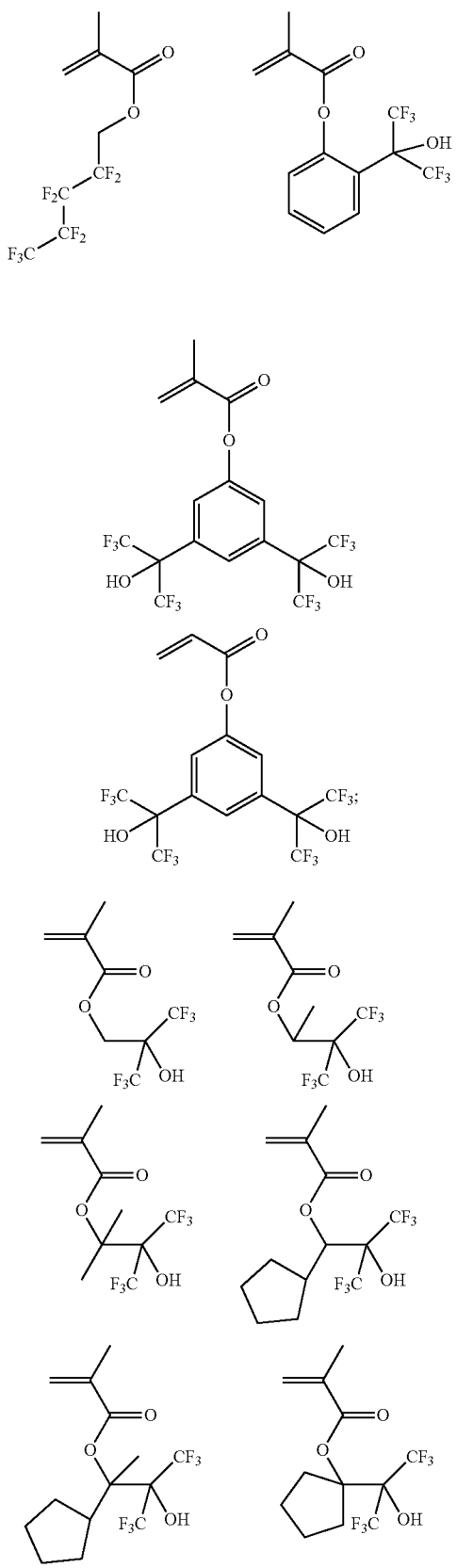
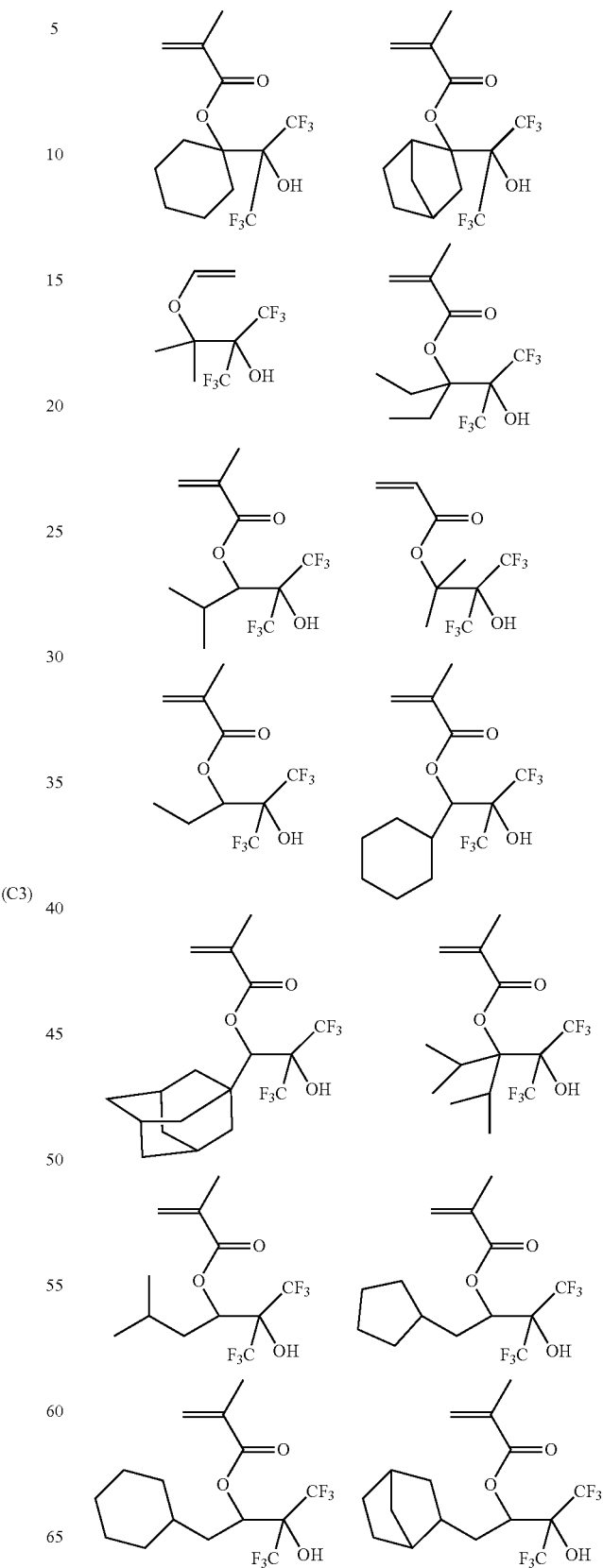

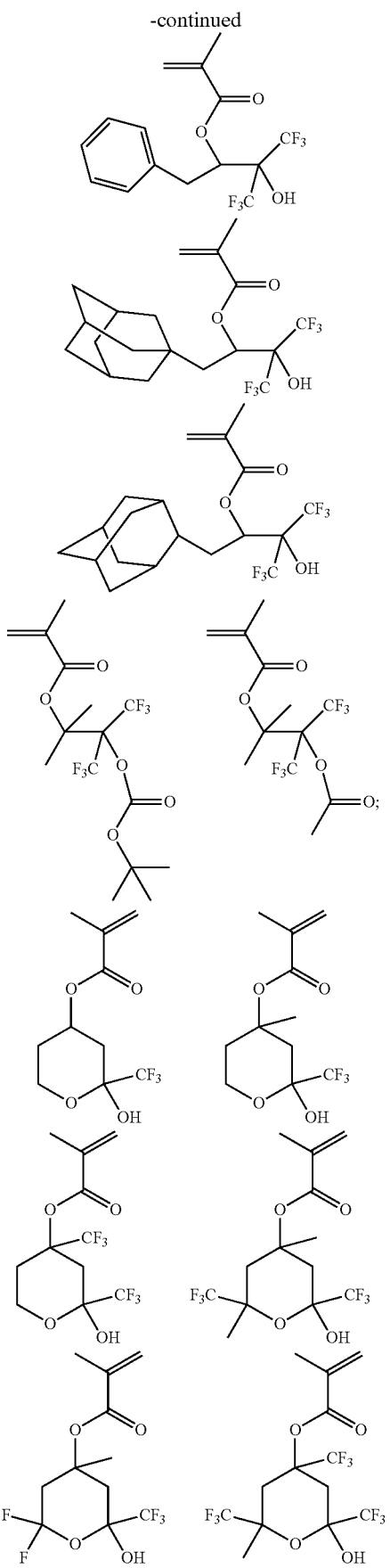
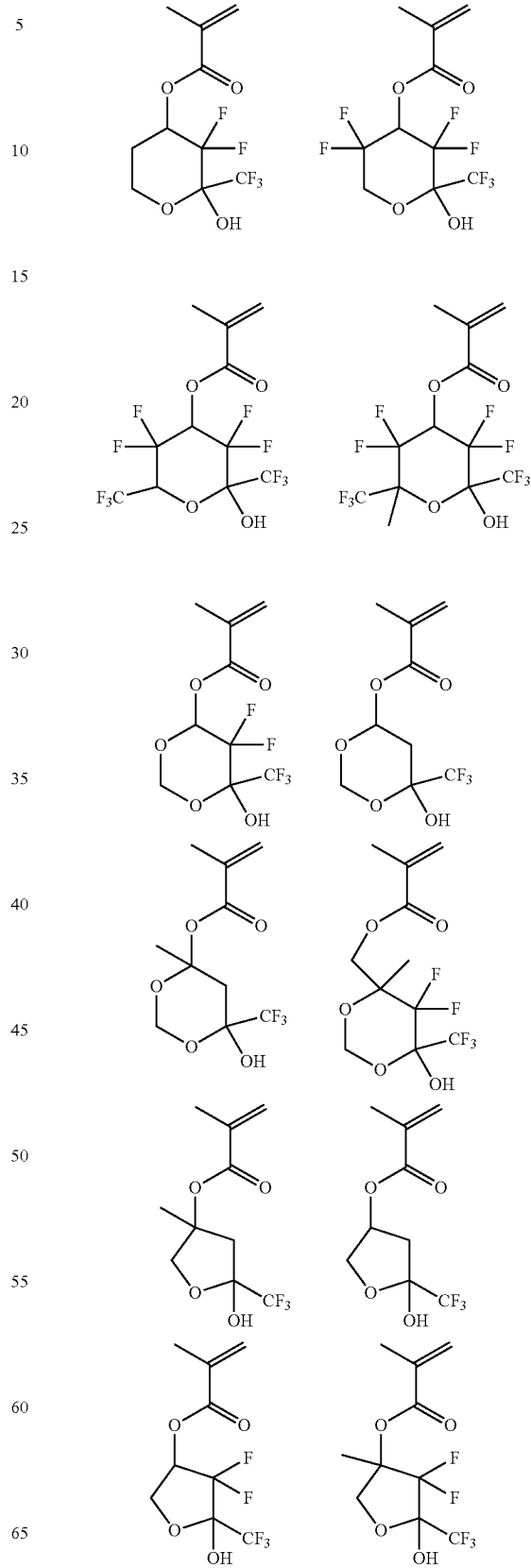

121
-continued
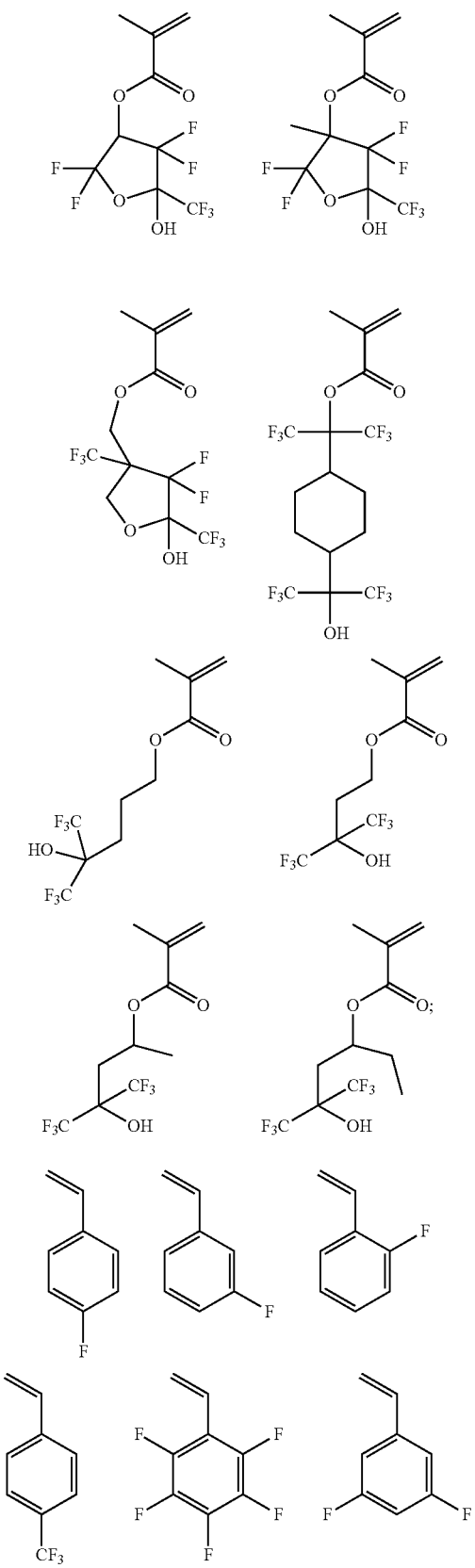
122
-continued
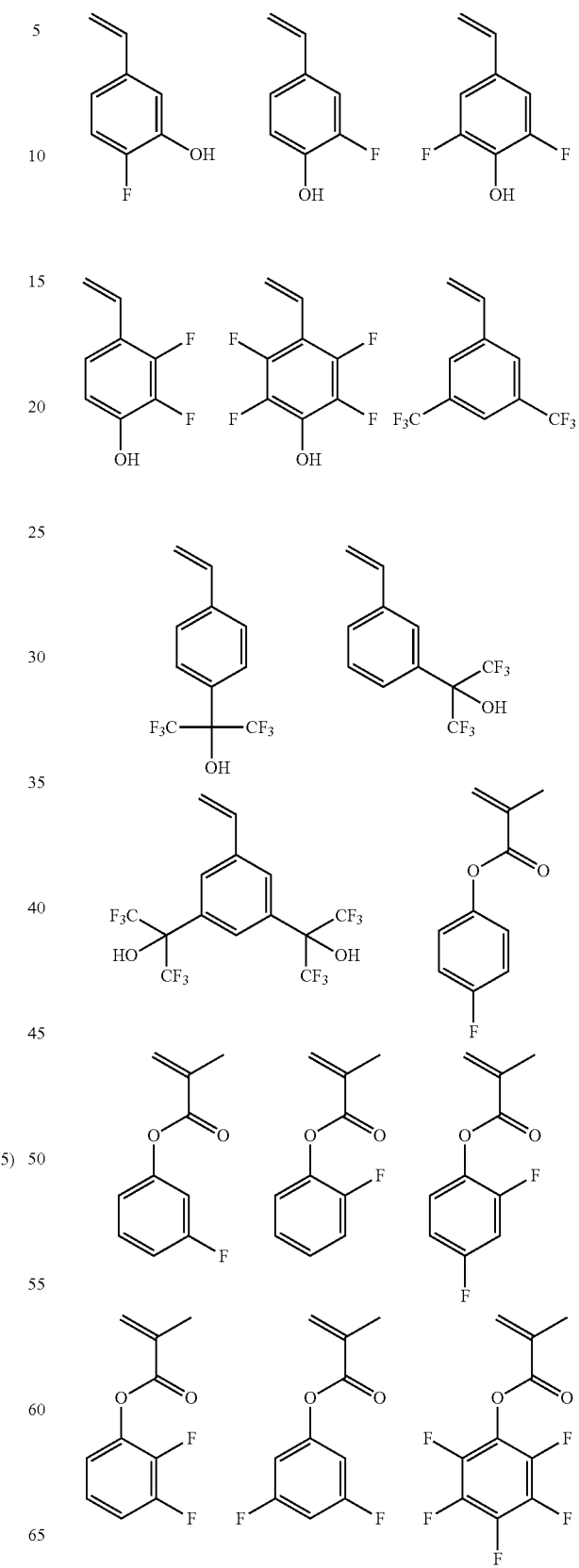
(C5)

123
-continued
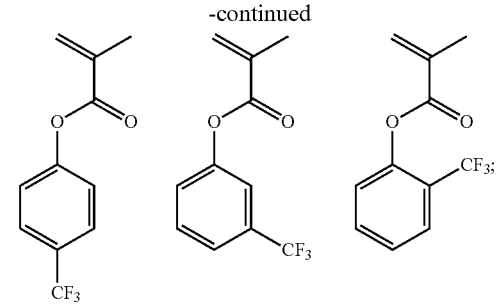
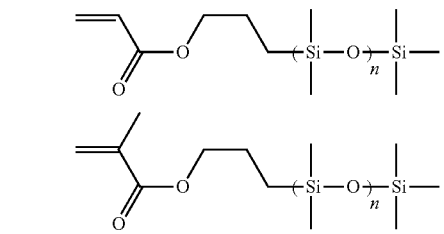
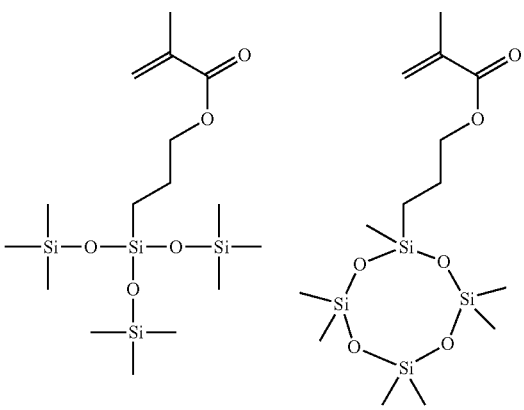
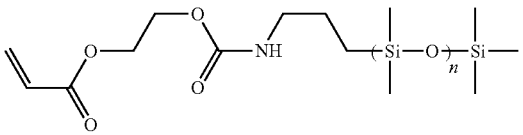
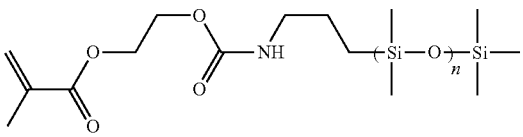
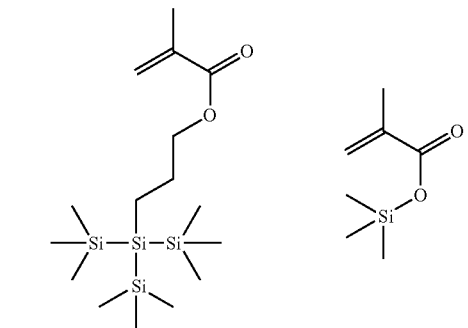
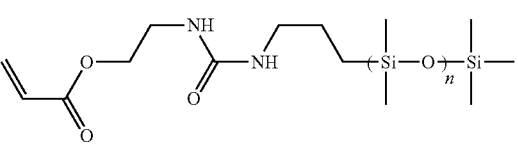
124
-continued
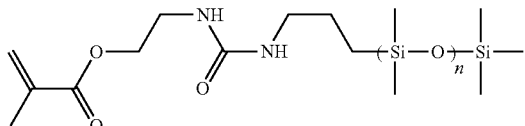
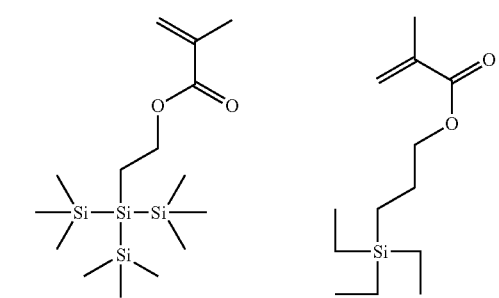
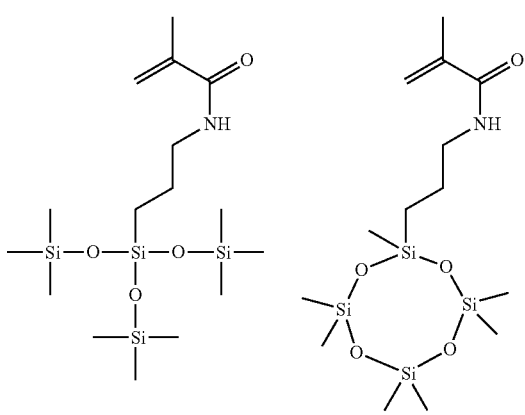
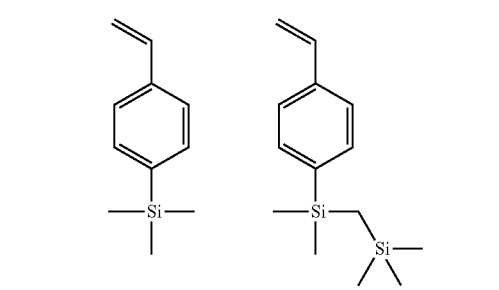
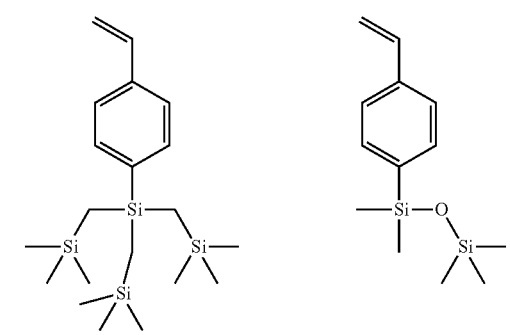

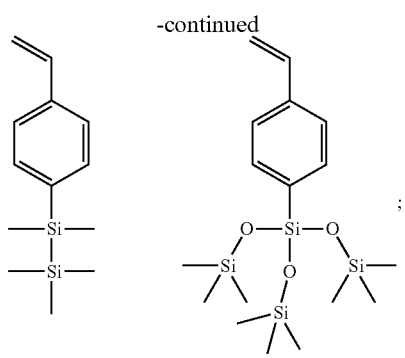
wherein n is an integer from 0 to 100
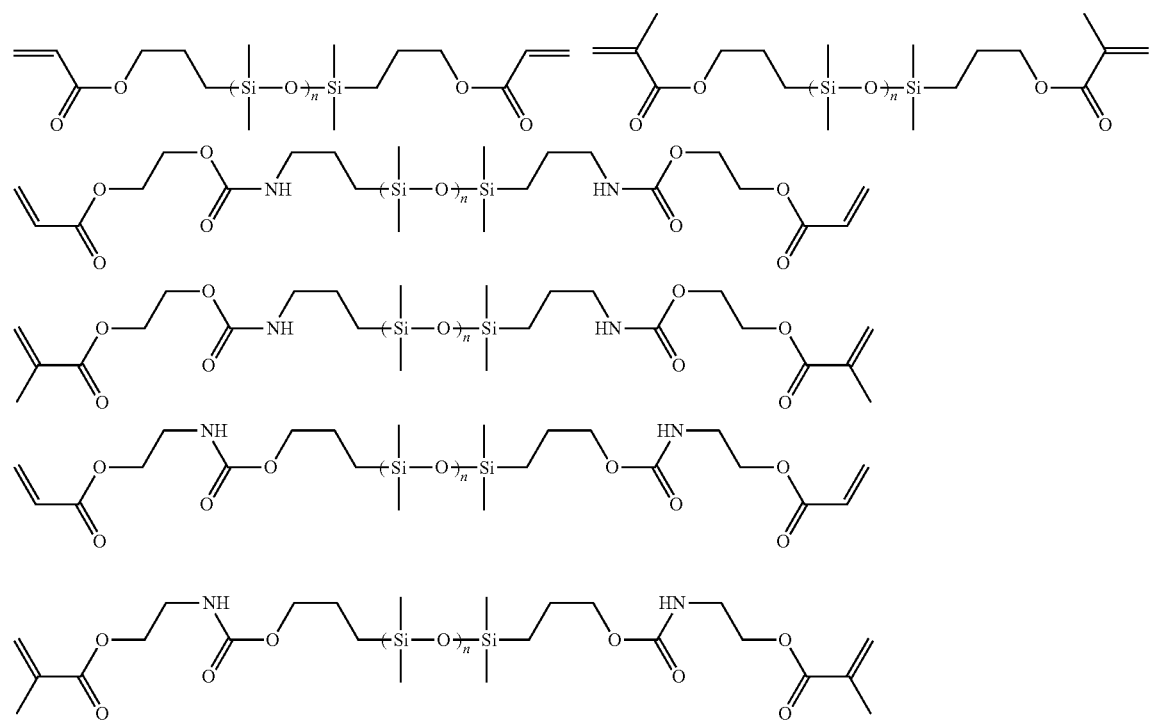
(C7)
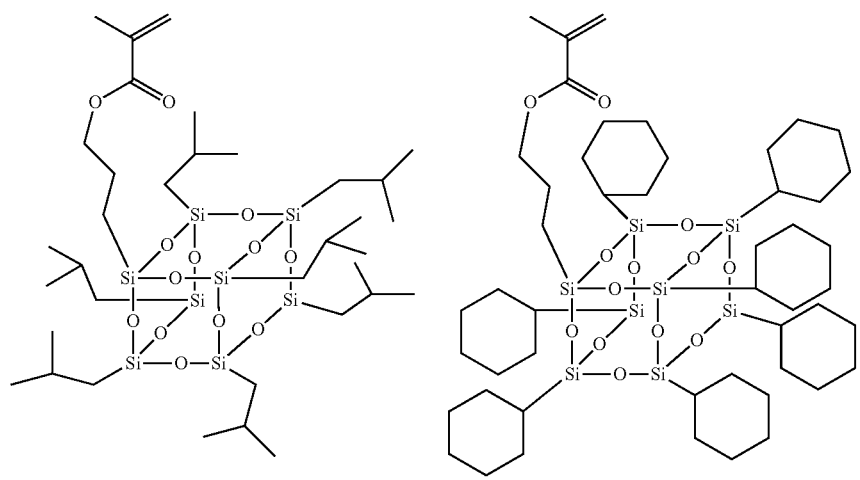

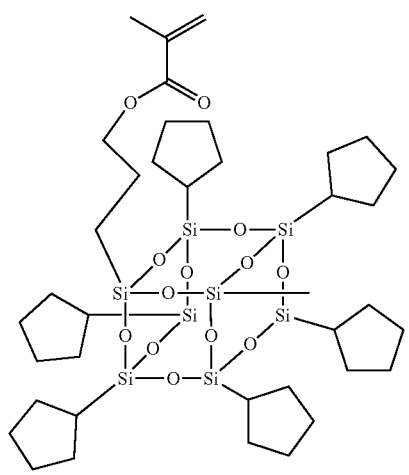

wherein n is an integer from 0 to 100.

2. The biomedical electrode composition according to claim 1, wherein the biomedical electrode composition further includes a carbon material, an indium tin oxide particle, or a particle coated with a metal selected from silver, gold, platinum, copper, and nickel.

3. The biomedical electrode composition according to claim 2, wherein the carbon material is carbon black and/or carbon nanotube.

4. The biomedical electrode composition according to claim 1, wherein the polymer compound is a copolymerized polymer compound that not only has the repeating unit "a", the repeating unit "b" and the repeating unit "c", but also includes a repeating unit "d" having one or more groups selected from a hydroxy group, carboxyl group, oxirane group, and oxetane group.

5. The biomedical electrode composition according to claim 4, wherein the biomedical electrode composition further includes a carbon material, an indium tin oxide particle, or a particle coated with a metal selected from silver, gold, platinum, copper, and nickel.

6. The biomedical electrode composition according to claim 5, wherein the carbon material is carbon black and/or carbon nanotube.

7. The biomedical electrode composition according to claim 1, wherein the ionic repeating unit "a" is a repeating unit "a1" represented by the following general formula (3),

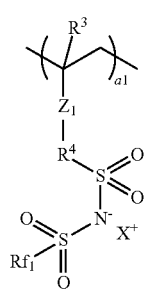

(3)

wherein,
$R^3$ represents a hydrogen atom or a methyl group;
$R^4$ represents any of a single bond, an ester group, or a linear, a branched, or a cyclic hydrocarbon group having 1 to 13 carbon atoms that may include an ether group;
$Z_1$ represents any of a single bond, a phenylene group, a naphthylene group, an ether group, an ester group, or an amide group;
"a1" satisfies the equation $0<a1<1.0$; and
$Rf_1$ and $X^+$ represent the same meanings as before.

8. The biomedical electrode composition according to claim 7, wherein the biomedical electrode composition further includes a carbon material, an indium tin oxide particle, or a particle coated with a metal selected from silver, gold, platinum, copper, and nickel.

9. The biomedical electrode composition according to claim 8, wherein the carbon material is carbon black and/or carbon nanotube.

10. The biomedical electrode composition according to claim 7, wherein the polymer compound is a copolymerized polymer compound that not only has the repeating unit "a", the repeating unit "b" and the repeating unit "c", but also includes a repeating unit "d" having one or more groups selected from a hydroxy group, carboxyl group, oxirane group, and oxetane group.

11. The biomedical electrode composition according to claim 10, wherein the biomedical electrode composition further includes a carbon material, an indium tin oxide particle, or a particle coated with a metal selected from silver, gold, platinum, copper, and nickel.

12. The biomedical electrode composition according to claim 11, wherein the carbon material is carbon black and/or carbon nanotube.

13. A biomedical electrode comprising
a conductive substrate and
a living body contact layer formed on the conductive substrate, wherein the living body contact layer is a cured product of the biomedical electrode composition according to claim 1.

14. The biomedical electrode according to claim 13, wherein the conductive substrate contains one or more substances selected from gold, silver, silver chloride, platinum, aluminum, magnesium, tin, tungsten, iron, copper, nickel, stainless steel, chromium, titanium, and carbon.

15. A biomedical electrode comprising
a conductive substrate and
a living body contact layer formed on the conductive substrate, wherein the living body contact layer is a cured product of the biomedical electrode composition according to claim 7.

16. The biomedical electrode according to claim 14, wherein the conductive substrate contains one or more substances selected from gold, silver, silver chloride, platinum, aluminum, magnesium, tin, tungsten, iron, copper, nickel, stainless steel, chromium, titanium, and carbon.

17. A method for manufacturing a biomedical electrode comprising a conductive substrate and a living body contact layer formed on the conductive substrate, the method comprising:
applying the biomedical electrode composition according to claim 1 to the conductive substrate, and
curing the applied biomedical electrode composition to form the living body contact layer.

18. The method for manufacturing a biomedical electrode according to claim 17, wherein the conductive substrate contains one or more substances selected from gold, silver, silver chloride, platinum, aluminum, magnesium, tin, tungsten, iron, copper, nickel, stainless steel, chromium, titanium, and carbon.

19. A method for manufacturing a biomedical electrode comprising a conductive substrate and a living body contact layer formed on the conductive substrate, the method comprising:
applying the biomedical electrode composition according to claim 7 to the conductive substrate, and
curing the applied biomedical electrode composition to form the living body contact layer.

20. The method for manufacturing a biomedical electrode according to claim 19, wherein the conductive substrate contains one or more substances selected from gold, silver, silver chloride, platinum, aluminum, magnesium, tin, tungsten, iron, copper, nickel, stainless steel, chromium, titanium, and carbon.

* * * * *